(12) United States Patent
Shekdar et al.

(10) Patent No.: US 8,916,503 B2
(45) Date of Patent: *Dec. 23, 2014

(54) METHODS AND MATERIALS USING SIGNALING PROBES

(75) Inventors: Kambiz Shekdar, New York, NY (US); Dennis J. Sawchuk, Hoboken, NJ (US); Jason M. Montez, Rumson, NJ (US)

(73) Assignee: Chromocell Corporation, North Brunswick, NJ (US)

( * ) Notice: Subject to any disclaimer, the term of this patent is extended or adjusted under 35 U.S.C. 154(b) by 1926 days.

This patent is subject to a terminal disclaimer.

(21) Appl. No.: 10/589,052

(22) PCT Filed: Feb. 17, 2005

(86) PCT No.: PCT/US2005/005080
§ 371 (c)(1),
(2), (4) Date: Sep. 8, 2008

(87) PCT Pub. No.: WO2005/079462
PCT Pub. Date: Sep. 1, 2005

(65) Prior Publication Data
US 2009/0106853 A1    Apr. 23, 2009

Related U.S. Application Data

(60) Provisional application No. 60/546,075, filed on Feb. 18, 2004.

(51) Int. Cl.
*C40B 20/00* (2006.01)
*C12Q 1/68* (2006.01)
*C12N 15/00* (2006.01)

(52) U.S. Cl.
CPC ..................... *C12Q 1/6841* (2013.01)
USPC ............................................................ 506/2

(58) Field of Classification Search
CPC ................. C12Q 2525/207; C12Q 2525/301; A01K 2217/05; C12N 1/02
USPC ............................................................ 506/2
See application file for complete search history.

(56) References Cited

U.S. PATENT DOCUMENTS

| | | | |
|---|---|---|---|
| 5,641,675 A | 6/1997 | Singer et al. | |
| 5,783,683 A | 7/1998 | Morrison | |
| 5,858,649 A | 1/1999 | Asgari et al. | |
| 5,866,336 A | 2/1999 | Nazarenko et al. | |
| 5,925,517 A | 7/1999 | Tyagi et al. | |
| 5,942,435 A | 8/1999 | Wheeler | |
| 6,037,130 A | 3/2000 | Tyagi et al. | |
| 6,203,986 B1 | 3/2001 | Singer et al. | |
| 6,291,162 B1 | 9/2001 | Tsien | |
| 6,361,944 B1 | 3/2002 | Mirkin et al. | |
| 6,391,593 B1 | 5/2002 | Weston et al. | |
| 6,461,864 B1 | 10/2002 | Soriano et al. | |
| 6,485,901 B1 | 11/2002 | Gildea et al. | |
| 6,534,274 B2 | 3/2003 | Becker et al. | |
| 6,589,743 B2 | 7/2003 | Sorge | |
| 6,692,965 B1 * | 2/2004 | Shekdar et al. | 435/455 |
| 6,743,581 B1 | 6/2004 | Vo-Dinh | |
| 6,750,052 B1 | 6/2004 | Shinohara et al. | |
| 6,872,525 B2 | 3/2005 | Ishibashi et al. | |
| 7,070,933 B2 | 7/2006 | Browne | |
| 7,098,320 B1 | 8/2006 | Mirkin et al. | |
| 7,132,241 B2 | 11/2006 | Ishibashi et al. | |
| 2001/0009760 A1 | 7/2001 | Horn et al. | |
| 2002/0090614 A1 | 7/2002 | Zhang et al. | |
| 2003/0032024 A1 | 2/2003 | Lizardi | |
| 2003/0059786 A1 | 3/2003 | Ward et al. | |
| 2003/0096322 A1 | 5/2003 | Giuliano et al. | |
| 2003/0215798 A1 * | 11/2003 | Short et al. | 435/6 |
| 2010/0129808 A1 | 5/2010 | Mirkin et al. | |

FOREIGN PATENT DOCUMENTS

| | | |
|---|---|---|
| CA | 2202549 | 4/1996 |
| CA | 2415731 | 1/2002 |
| EP | 0 745 690 | 12/1996 |
| EP | 1 172 445 | 1/2002 |
| EP | 1405908 | 4/2004 |
| WO | WO 91/07660 | 5/1991 |
| WO | WO 94/02646 | 2/1994 |
| WO | 9832868 | 7/1998 |
| WO | WO 98/58085 | 12/1998 |
| WO | WO 99/10539 | 3/1999 |
| WO | WO 00/01850 | 1/2000 |
| WO | WO 00/31302 | 6/2000 |
| WO | WO 00/62063 | 10/2000 |
| WO | WO 02/06524 | 1/2002 |

(Continued)

OTHER PUBLICATIONS

Tsuji et al., Biophysical Journal 78: 3260-3274, 2000.*

(Continued)

*Primary Examiner* — Larry Riggs
*Assistant Examiner* — Karla Dines
(74) *Attorney, Agent, or Firm* — Ropes & Gray LLP; Jane T. Gunnison; Wyan-Ching M. Lee

(57) ABSTRACT

Methods of isolating cells or generating cell lines comprising the step of exposing the cells to signaling probes that produce a signal upon hybridization to a target sequence, as well as methods of quantifying the level of expression of an RNA of interest, methods for identifying genetic recombinational events in living cells and methods of generating a transgenic animal using the isolated cells. Methods for isolating a plurality of cells encoding a plurality of different RNAs associated with a same nucleic acid tag sequence, comprising the step of exposing the cells to a same signaling probe that produces a detectable signal upon hybridization to the same nucleic acid tag sequence, are also provided. Signaling probes and protease probes that form stem-loop structures, three-arm junction structures, and dumbbell structures may be used in the above methods.

18 Claims, 60 Drawing Sheets

(56) References Cited

FOREIGN PATENT DOCUMENTS

| WO | WO 02/29117 | 4/2002 |
|---|---|---|
| WO | WO 02/051988 | 7/2002 |
| WO | WO 0131059 | 5/2003 |
| WO | WO 03/048346 | 6/2003 |
| WO | WO 03/054223 | 7/2003 |

OTHER PUBLICATIONS

Bratu et al., "Visualizing the distribution and transport of mRNAs in living cells," *PNAS*, 100(23):13308-13313 (2003).
Bratu, "Molecular beacons: Fluorescent probes for detection of endogenous mRNAs in living cells," *Methods in Molecular Biology*, 319:1-14 (2006).
Butler, "Cell line development and culture strategies: future prospects to improve yields," *Cell Culture and Upstream Processing*, Department of Microbiology, University of Manitoba, Manitoba, Canada, Chapter 1, pp. 3-15 (2007).
Chen et al., "Efficient cytosolic delivery of molecular beacon conjugates and flow cytometric analysis of target RNA," *Nucleic Acids Research*, 36(12):e69 (2008).
Dirks et al., "Methods for visualizing RNA processing and transport pathways in living cells," *Histochemistry and Cell Biology*, 115(1):3-11 (2001).
Gang, "Sensitive mRNA detection in single living cells," *Abstracts of Papers American Chemical Society*, 228(2):U242-U243 (2004).
Gurtu et al., "IRES bicistronic expression vectors for efficient creation of stable mammalian cell lines," *Biochemical and Biophysical Research Communication*, 229(1):295-298 (1996).
Horlick et al., "Rapid Generation of Stable Cell Lines Expressing Corticotropin-Releasing Hormone Receptor for Drug Discovery," *Protein Expression and Purification*, 9(3):301-308 (1997).
Maksimenko et al., "Real-time detection and efficacy of antisense oligonucleotides delivered by Pamam dendrimers in living cells," *Journal of Drug Delivery Science and Technology*, 15(1):75-79 (2005).
Medley et al., "Simultaneous monitoring of the expression of multiple genes inside of single breast carcinoma cells," *Analytical Chemistry*, 77 (15):4713-4718 (2005).
Molenaar et al., "Linear 2' O-Methyl RNA probes for the visualization of RNA in living cells," *Nucleic Acids Research*, 29(17):e89 (2001).
Nitin et al., "NLS peptide conjugated molecular beacons for visualizing nuclear RNA in living cells," *Bioconjugate Chemistry*, 19(100):2205-2211 (2008).
Nitin et al., "Peptide-linked molecular beacons for efficient delivery and rapid mRNA detection in living cells," *Nucleic Acids Research*, 32(6):e58 (2004).
Nitin et al., "Translation inhibition reveals interaction of 2'-deoxy and 2'-O-methyl molecular beacons with mRNA targets in living cells," *Nucleic Acids Research*, 37(15):4977-4986 (2009).
Rhee et al., "Target accessibility and signal specificity in live-cell detection of BMP-4 mRNA using molecular beacons," *Nucleic Acids Research*, 36(5):e30 (2008).
Rodriguez et al., "Imaging mRNA movement from transcription sites to translation sites," *Seminars in Cell and Developmental Biology*, 18(2):202-208 (2007).
Santangelo et al., "Direct visualization of mRNA colocalization with mitochondria in living cells using molecular beacons," *Journal of Biomedical Optics*, 10(4):44025 (2005).
Santangelo et al., "Dual FRET molecular beacons for mRNA detection in living cells," *Nucleic Acids Research*, 32(6):e57 (2004).
Santangelo et al., "Live-cell characterization and analysis of a clinical isolate of bovine respiratory syncytial virus, using molecular beacons," *Journal of Virology*, 80(2):682-688 (2006).
Santangelo et al., "Nanostructured probes for RNA detection in living cells," *Annals of Biomedical Engineering*, 34(1):39-50 (2006).
Tang et al., "Monitoring p21 mRNA expression in living cell based on molecular beacon fluorescence increasing rate," *Chinese Science Bulletin*, 53(3):357-361 (2008).
Tang et al., "mRNA detection in living cell using phosphorothioate-modified molecular beacon" *Chinese Science Bulletin*, 54(9):1507-1514 (2009).
Tyagi et al., "Imaging native beta-actin mRNA in motile fibroblasts," *Biophysical Journal*, 87(6):4153-4162 (2004).
Van Craenenbroeck et al., "Evaluation of the tetracycline- and ecdysone-inducible systems for expression of neurotransmitter receptors in mammalian cells," *European Journal Neuroscience*, 14(6):968-976 (2001).
Wang et al., "Imaging and characterizing influenza a virus mRNA transport in living cells," *Nucleic Acids Research*, 36(15):4913-4928 (2008).
Wang et al., "Molecular engineering of DNA: molecular beacons," *Angewandte Chemie*, 48(5):856-870 (2009).
Wu et al., "Nucleic acid beacons for long-term real-time intracellular monitoring," *Analytical Chemistry*, 80(8):3025-3028 (2008).
Yang et al., "Monitoring nucleic acids using molecular beacons," *Current Pharmaceutical Biotechnology*, 6(6):445-452 (2005).
Zahn-Zabal et al., "Development of stable cell lines for production or regulated expression using matrix attachment regions," *Journal of Biotechnology*, 87(1):29-42 (2001).
Davis et al., "Generation of cDNA Expression Libraries Enriched for In-Frame Sequences," *PNAS*, 94:2128-2132 (1997).
Tashiro et al., "Signal Sequence Trap: A Cloning Strategy for Secreted Proteins and Type I Membrane Proteins," *Science*, 261(5121):600-603 (1993).
Fang et al., "Molecular beacons: fluorogenic probes for living cell study," Cell Biochemistry and Biophysics, 37 (2):71-81 (2002).
Perlette et al:, "Real-time monitoring of intracellular mRNA hybridization inside single living cells," Analytical Chemistry, 73(22):5544-5550 (2001).
Sells et al., "Epitope-tag vectors for eukaryotic protein production," *Gene* 152:187-189 (1995).
Vijayanathan et al., "Direct measurement of the association constant of HER2/neu antisense oligonucleotide to its target RNA sequence using a molecular beacon," *Antisense and Nucleic Acid Drug Development* 12(4):225-233 (2002).
Geisenberger et al., "Monitoring the conjugal transfer of plasmid RP4 in activated sludge and in situ identification of the transconjugants," *FEMS Microbiology Letters* 174:9-17 (1999).
An et al., "High-Efficiency Transduction of Human Lymphoid Progenitor Cells and Expression in Differentiated T Cells," *Journal of Virology* 71(2):1397-1404 (1997).
Borth et al., "Efficient Selection of High-Producing Subclones During Gene Amplification of Recombinant Chinese Hamster Ovary Cells by Flow Cytometry and Cell Sorting," Biotechnology & Bioengineering, 71:266-273 (2000/2001).
Dell'Arciprete et al., "High-Efficiency Expression Gene Cloning by Flow Cytometry," *The Journal of Histochemistry and Cytochemistry*, 44(6):629-640 (1996).
Gaines et al., "pIRES-CD4t, a dicistronic expression vector for MACS- or FACS-based selection of transfected cells," *BioTechniques*, 26(4):683-688 (1999).
Kurokawa et al., "A Pair of Fluorescent Resonance Energy Transfer-based Probes for Tyrosine Phosphorylation of the CrkII Adaptor Protein in Vivo," *The Journal of Biological Chemistry*, 276(33):31305-31310 (2001).
Babinet et al., "Transgenic mice," Genome, vol. 31, pp. 938-949 (1989).
Gagneten et al., "Brief Expression of GFP cre Fusion Gene in Embryonic Stem Cells Allows Rapid Retrieval of Site-Specific Genomic Deletions," Nucleic Acids Research, vol. 25, pp. 3326-3331 (1997).
Kitazawa et al., "In Situ DNA-RNA Hybridization Using In Vivo Bromodeoxyuridine-Labeled DNA Probe," Histochemistry, vol. 92, pp. 195-199 (1989).
Leone et al., "Molecular Beacon Probes Combined with Amplification by NASBA Enable Homogeneous, Real-Time Detection of RNA," Nucleic Acids Research, vol. 26, No. 9, pp. 2150-2155 (1998).
Li et al., "Molecular Beacon-Based Homogeneous Fluorescence PCR Assay for the Diagnosis of Infectious Diseases," Analytical Sciences, vol. 16, pp. 245-248 (2000).
Martone et al., "Subcellular Localization of mRNA in Neuronal Cells," Molecular Neurobiology, vol. 18, pp. 227-246 (1998).

(56) References Cited

OTHER PUBLICATIONS

Matsuo, "In Situ Visualization of Messenger RNA for Basic Fibroblast Growth Factor in Living Cells," Biochimica et Biophysica Acta, 1379, pp. 178-184 (1998).
Pennline et al., "Detection of In Vivo-Induced IL-1 mRNA in Murine Cells by Flow Cytometry (FC) and Fluorescent In Situ Hybridization (FISH)," Lymphokine and Cytokine Research, vol. 11, No. 1, pp. 65-71 (1992).
Phillips et al., "Antisense RNA Amplification: A Linear Amplification Method for Analyzing the mRNA Population from Single Living Cells," METHODS: A Companion to Methods in Enzymology, vol. 10, No. 3, pp. 283-288 (1996).
Sixou et al., "Intracellular Oligonucleotide Hybridization Detected by Fluorescence Resonance Energy Transfer (FRET)", Nucleic Acids Research, vol. 22, No. 4, pp. 662-668 (1994).
Sokol et al., "Real Time Detection of DNA-RNA Hybridization in Living Cells," Proc. Natl. Acad. Sci. USA, vol. 95, pp. 11538-11543 (1998).
Tan et al., "Molecular Beacons: A Novel DNA Prode for Nucleic Acid and Protein Studies" Chem. Eur., vol. 6, pp. 1107-1111 (2000).
Tsuji et al., "Direct Observation of Specific Messenger RNA in a Single Living Cell under a Fluorescence Microscope," Biophysical Journal, vol. 78, pp. 3260-3274 (Jun. 2000).
Tyagi et al., "Multicolor Molecular Beacons for Allele Discrimination," Nature Biotechnology, vol. 16, pp. 49-53 (1998).
Tyagi et al., "Molecular Beacons: Probes that Fluoresce Upon Hybridization," Nature Biotechnology, vol. 14, pp. 303-308 (1996).
Campbell et al., "Totipotency or Multipotentiality of Cultured Cells: Applications and Progress," *Theriogenology*, 47:63-72 (1997).
Rayner et al., "A Simple and Efficient Procedure for Generating Stable Expression Libraries by cDNA Cloning in a Retroviral Vector," *Molecular and Cellular Biology* 14(2):880-887 (1994).
Kovala et al., "High-Efficiency Transfection of Endothelial Cells," *FASEB* 14:2486-2494 (2000).
Conlon et al., "Pyrene excimer signaling molecular beacons for probing nucleic acids," *Journal of the American Chemical Society* 130(1):336-342 (2008).
Hatzakis et al., "Cellular HIV-1 DNA load predicts HIV-RNA rebound and the outcome of highly active antiretroviral therapy," *AIDS* 18(17):2261-2267 (2004).
Herdewijn, P., Ed., "Oligonucleotide Synthesis: Methods and Applications," *Methods in Molecular Biology* 288, Humana Press Inc. (2005) (Table of Contents).
Krawczynski et al., "Experimental infectivity studies of genetically engineered monoclonal hepatitis B virus (HBV) polymerase gene mutants in chimpanzees," *Hepatology* 38(4):S1 251A (2003).
Morandi et al., "Monitoring HCV RNA viral load by locked nucleic acid molecular beacons real time PCR," *Journal of Virological Methods* 140(1-2):148-154 (2007).
Mukewar et al., "Segmentation of bionano images for understanding cell dynamics," *IEEE Engineering in Medicine and Biology Society* 3:1759-1762 (2004).
Vicens et al., "Investigation of molecular beacon aptamer-based bioassay for platelet-derived growth factor detection," *Chembiochem* 6(5):900-907 (2005).
Zuo et al., "A novel sandwich assay with molecular beacon as report probe for nucleic acids detection on one-dimensional microfluidic beads array," *Analytica Chimica Acta* 587(1):9-13 (2007).
Braasch et al., "Antisense inhibition of gene expression in cells by oligonucleotides incorporating locked nucleic acids: effect of mRNA target sequence and chimera design", Nucleic Acids Research, 30(23): 5160-5167 (2002).
Gait, "Peptide-mediated cellular delivery of antisense oligonucleotides and their analogues", CMLS, Cell. Mol. Life Sci. 60:844-853 (2003).
Gopalakrishnan et al., "siRNA and DNA Transfer to Cultured Cells", Methods in Molecular Biology, 480: 31-52 (2009).
Hoffmann et al., "Expression screening of factors binding to the osteocalcin bone-specific promoter element OC Box I: isolation of a novel osteoblast differentiation-specific factor," J. Cell. Biochem. 80:156-168 (2000).
Kurreck, "Antisense technologies: Improvement through novel chemical modifications", Eur. J. Biochem. 270:1628-1644 (2003).
Mitchell, "Turning the spotlight on cellular imaging", Nature Biotechnology, 19(11): 1013-1017 (2001).
Nesterova et al., "Killing the Messenger: Antisense DNA and siRNA", Current Drug Targets, 5: 683-689 (2004).
Pestov et al., "Genetic selection of growth-inhibitory sequences in mammalian cells," Proc. Natl. Acad. Sci. USA 91:12549-12553 (1994).
Rose, "Optimization of Transfection", Current Protocols in Neuroscience (1997) A.1B.1-A.1B.3.
Stark et al., "Forward genetics in mammalian cells: function approaches to gene discovery," Human Molecular Genetics 8(10):1925-1938 (1999).
Zambrowicz et al., "Disruption and sequence identification of 2,000 genes in mouse embryonic stem cells," Nature 392:608-611 (1998).
Ziieng et al., "A system for rapid generation of coat color-tagged knockouts and defined chromosomal rearrangements in mice," Nucl. Acids Res. 27(11):2354-2360 (1999).
Robbins et al., "Increased Probability of Expression from Modified Retroviral Vectors in Embryonal Stem Cells and Embryonal Carcinoma Cells," Journal of Virology 71(12):9466-9474 (1997).
Amit et al., "Derivation and spontaneous differentiation of human embryonic stem cells," *J. Anat.* 200:225-232 (2002).
Andrews et al., "Transcriptional modulation of viral reporter gene constructs following induction of the cellular stress response," *Nucleic Acids Research* 25(5):1082-1084 (1997).
Bonetta et al., "Flow cytometry smaller and better," *Nature Methods* 2(10):785-795 (2005).
Brielmeier et al., "Improving stable transfection efficiency: antioxidants dramatically improve the outgrowth of clones under dominant marker selection," *Nucleic Acids Research* 26(9):2082-2085 (1998).
Imoto et al., "Identification and functional characterization of a novel human protein highly related to the yeast dynamin-like GTPase Vps1p," *Journal of Cell Science* 111:1341-1349 (1998).
Kawai et al., "Analysis of cytoplasmic antigens in acute leukemia by flow cytometry," Rinsho Ketsueki 34(1):13-20, 1993 (abstract only).
Lerner et al., "Antibodies to small nuclear RNAs complexed with proteins are produced by patients with systemic lupus erythematosus," Proc. Natl. Acad. Sci. USA 76(11):5495-5499 (1979).
Seferos et al., "Nano-flares: Probes for Transfection and mRNA Detection in Living Cells," *J Am Chem Soc.* 129(50):15477-15479 (2007).
Seidl et al., "Evaluation of Membrane Physiology Following Fluorescence Activated or Magnetic Cell Separation," *Cytometry* 36:102-111 (1999).
Terpe, "Overview of tag protein fusions: from molecular and biochemical fundamentals to commercial systems," *Appl Microbiol Biotechnol* 60:523-533 (2003).
Watanabe et al., "Gene Transfection of Mouse Primordial Germ Cells in Vitro and Analysis of Their Survival and Growth Control," *Exp Cell Res* 230:76-83 (1997).
Dubertret et al., "Single-mismatch detection using gold-quenched fluorescent oligonucleotides," *Nature Biotechnology* 19(4):366-370 (2001).
Xi et al., "Use of DNA and peptide nucleic acid molecular beacons for detection and quantification of rRNA in solution and in whole cells," *Applied And Environmental Microbiology* 69(9):5673-5678 (2003).

\* cited by examiner

C 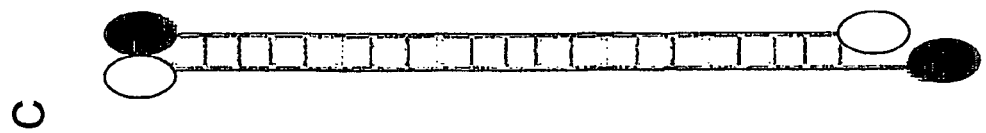
B 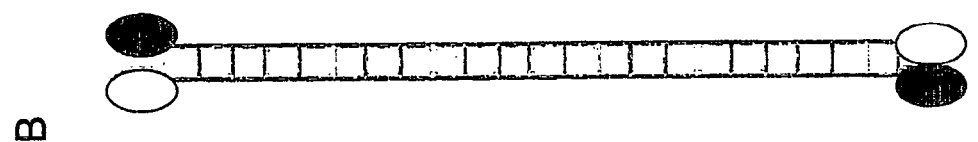
A 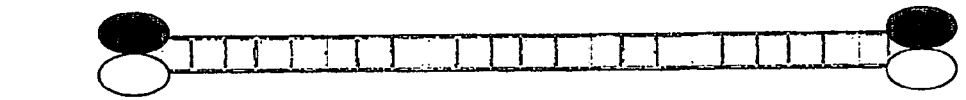
FIG. 2

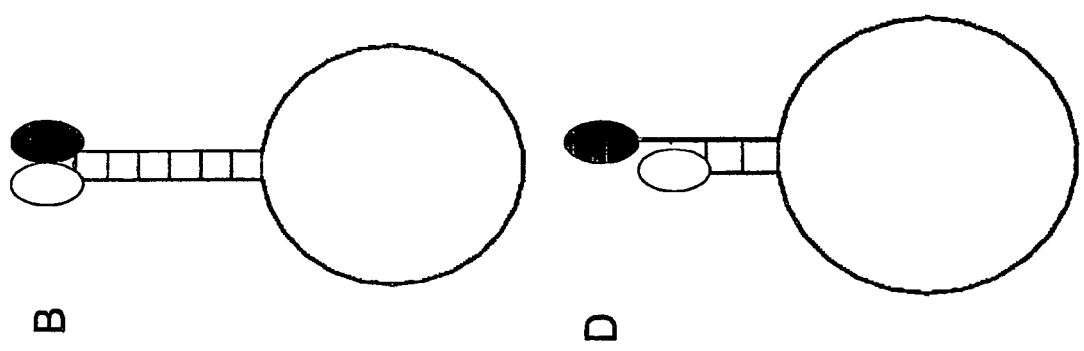
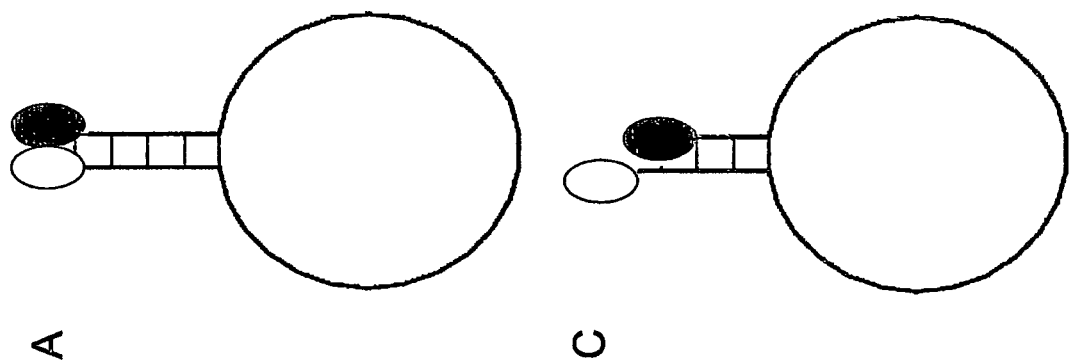
FIG. 5

5' GCGAG AGCGACAAGCAGACCCTATAGAAC CTCGC 3'

FP3

FP4   5' CTGC AGCGACAAGCAGACCCTATAGAAC GGG 3'

FP5    5' ggaa TCCCAGTTCCTGTGCCTTAAGAAC ttcc 3'

FIG. 12

FP6   5' ggaa TCGCAGAACGACAGGGTTAACTTC ttcc 3'

FIG. 13

FP7    5' ggaa AGCGACAAGCAGACCCTATAGAAC ttcc 3'

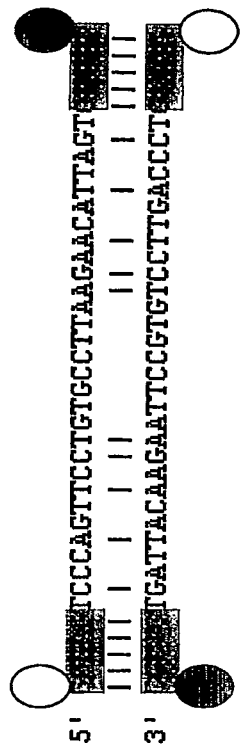
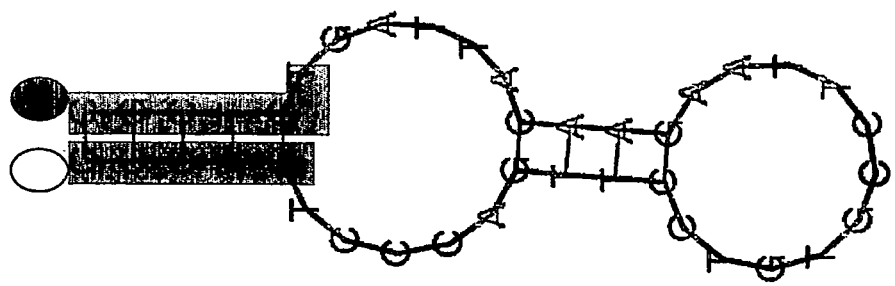
FP8    5' GCGAG TCCCAGTTCCTGTGCCTTAAGAACattagtCTCGC 3'
FIG. 15

FP9    5' ggaa TCCCAGTTCCTGTGCCTTAAGAACattagtttcc 3'

FIG. 16

FP10    5' gtgat TCCCAGTTCCTGTGCCTTAAGAAC atcac 3'

FIG. 17

FP11    5' ggac TCCCAGTTCCTGTGCCTTAAGAAC gtcc 3'

FIG. 18

FP12    5' ggg    TCCCAGTTCCTGTGCCTTAAGAAC ccc 3'

FIG. 19

FP13    5' gcg    TCCCAGTTCCTGCCCTTAAGAAC cgc 3'

FIG. 20

FP14  5' gcgag ATCGATCTAGCTTATGGATCTTAGC CTCGC 3'

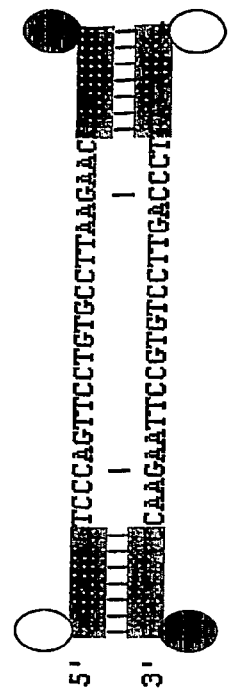
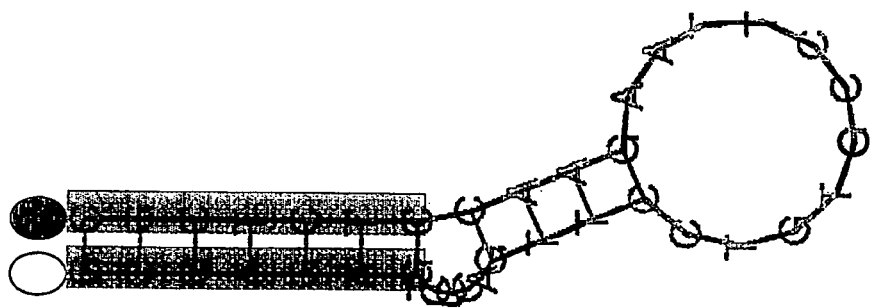
FP17  5' GCGAGAG TCCCAGTTCCTGTGCCTTAAGAAC CTCTCGC 3'
FIG. 24

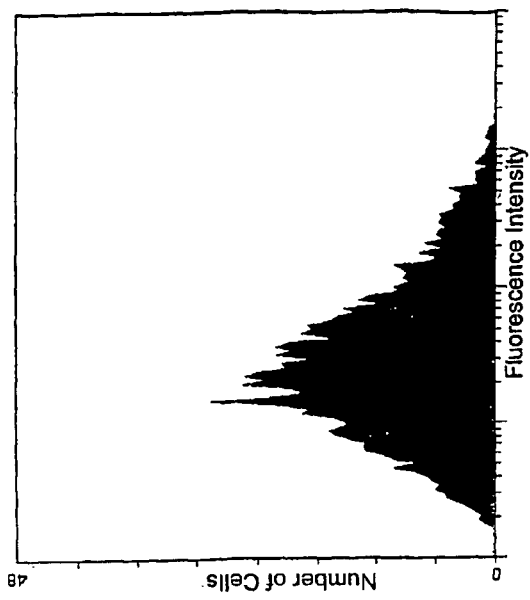
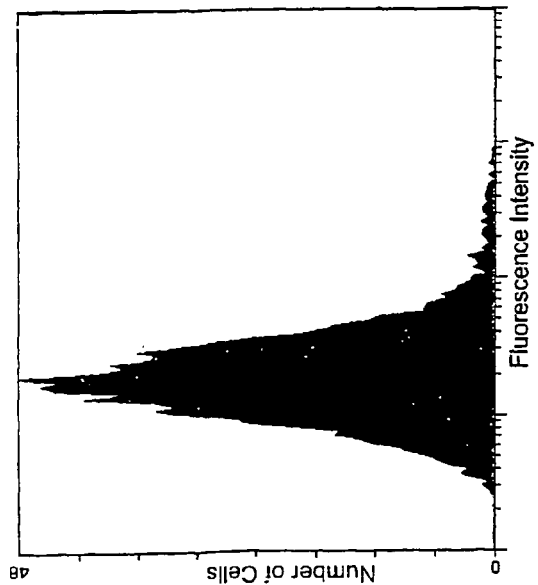
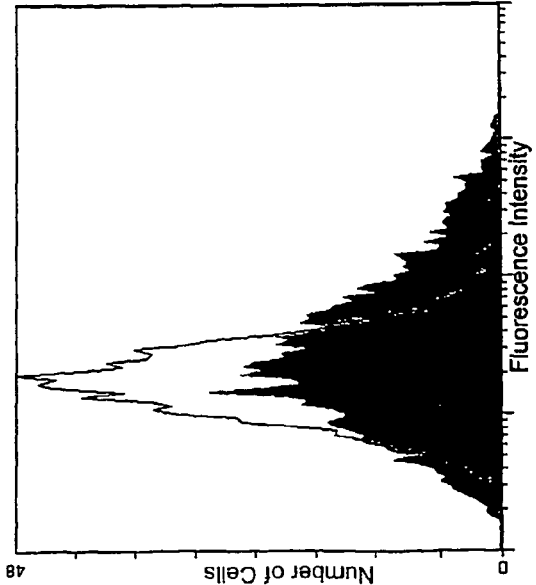
FIG. 28

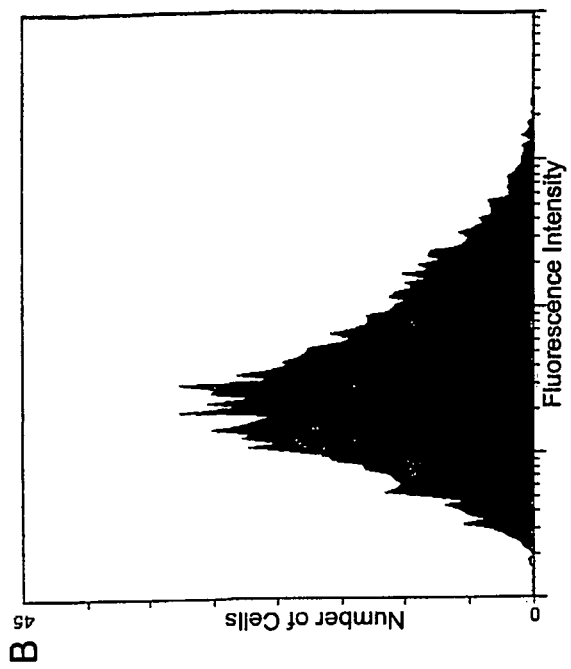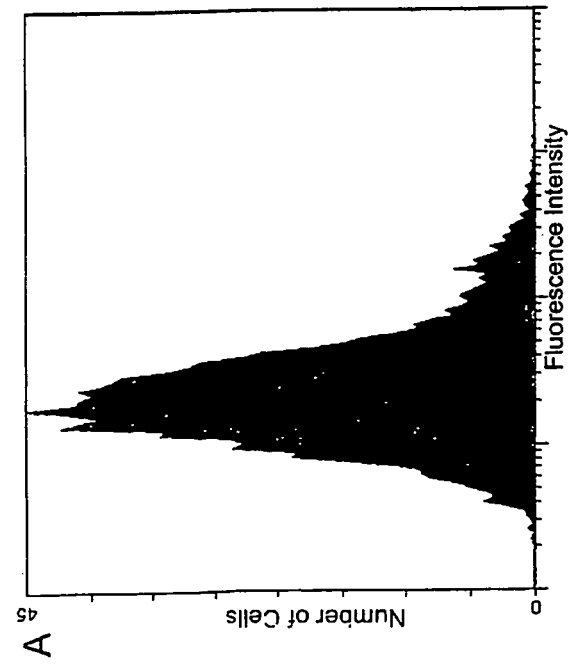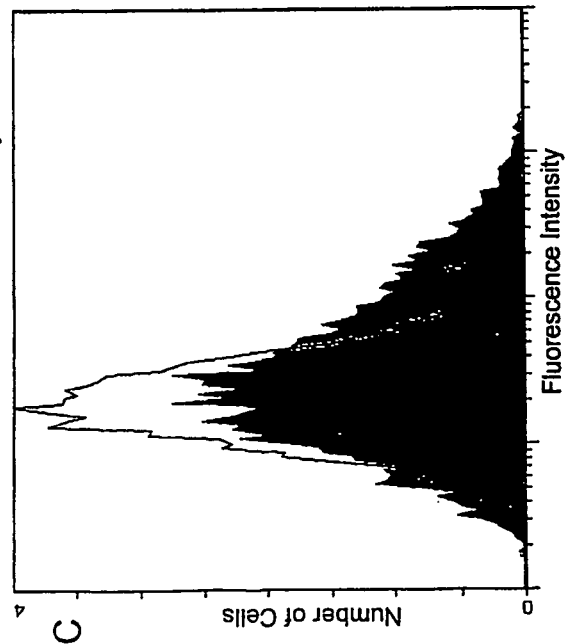
FIG. 29

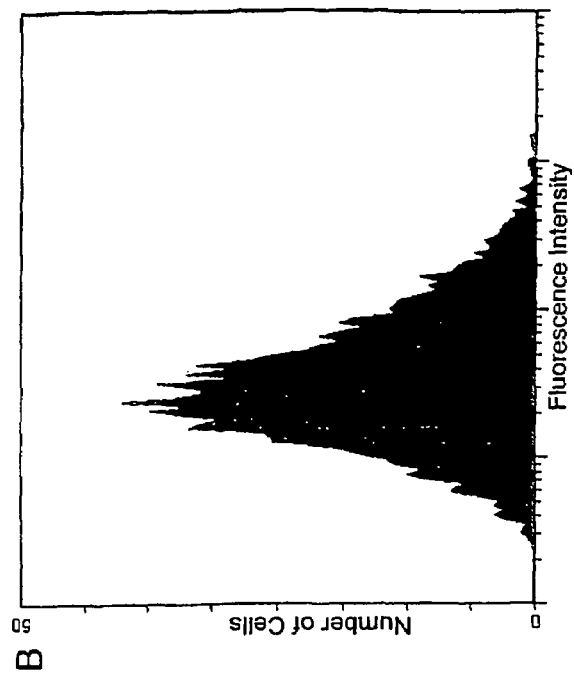
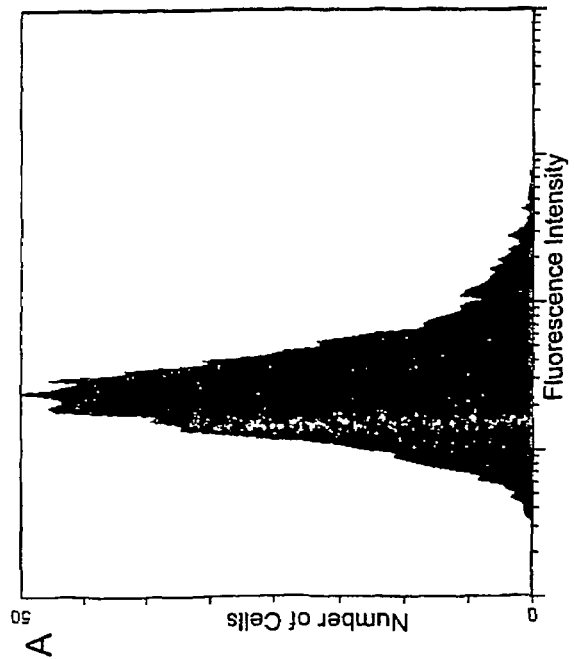
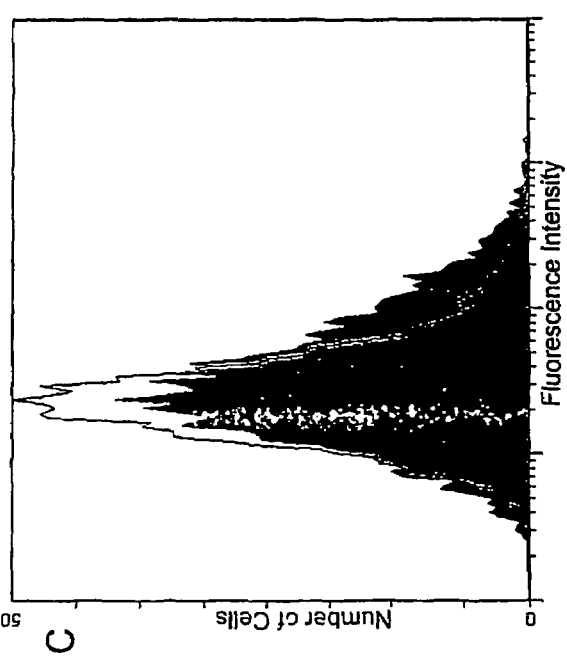
FIG. 31

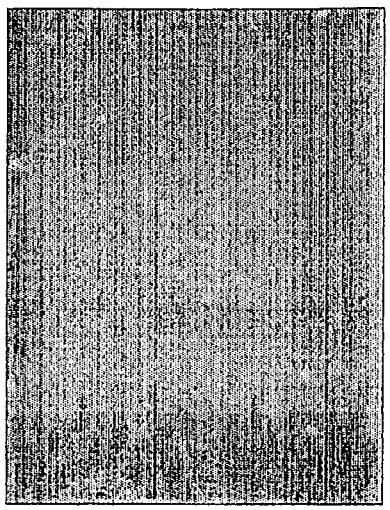
FIG. 34

A

```
ACCTTGCCAAATCCTGCACATCGAACATCGAAGAGGTTCAAAGGCTTCGAAGAGCTCGCTCCGCTTGAGGGCGAACTTCTCACA
GCAGGTGGACAGGAAGGTTCTAATGTTCTTAAGGCACAGGAACTGGGACATCTGGGCGCCCAGTTGACCTCACGCA
GGTTGATGGCATGGGGTAGCAGGTTGTTAAGCACTTGACACAGAAGGACACCATCCCGAGGGCCTGAGCCAGTTCA
CACACCTGAGCCCATCCAGTCACGCGGTGCTGGGCGCAGCCCGGACTCGATGAGCCAGGTTGCAACCAGTGGTCATTG
CGCCCACAGTCCATGCGAACATGCTCTTCACCGTGGGAAGGCCATGAAGGCCACTGGGTCGCAGGACAGA
GCAGACAGGGTGTAGATGCCTCATGAGGTCGATCTGGTCGGCGCCTCATTCTCCACTGTAGATGTCTTCATCACCTACA
CTCTCCTCCGCAGCAGCCTTGTGTACTTCTGTGCTCACAGTCATACGCGTCTCCAGCGGCTCCAGCGCGGCAG
GGGCTTCAAGAAATGTCTGCTGATGGAGCCCAGCTGTCAGTGCTACTTCTGCCTCTGCTGATGTATGAACACGA
AGCAGGTCCTCGCCAGGGCTGCCCCATAGCCAAGAACGATCTTCCTTCATGTCTCCTTGTATTTCGTTGCTCAGGTTGATGAGAACCGTTGATGAAGACCTGGTGACTTCTCCAGCTTC
GCTCAGTAGCCGCCATAGGAACGCTGTGCCCGCACACGTCAGCAGGTGTTCTTGAGAACATTCCTGCGACCACC
ATCTGCACGTCTCCCGGAGTCTCCCGCAGGTGAACCTGTGATATTTGAGAAGCTGCTGTGTGATAGGCACC
ATCACAGTCTCCCGGAGGTGAACCTCAGCGCAGCCTGTCTCGCTTCTCCTTGACTTCGTTCTCA
TGCGTGTGTTCACCAGCTCAGTGAATTTGGTGATCCCCTGCAGGTCTGTTGTTGACCTTGTTGACCTCTGACCTGAGTTCAA
ACTGAGCCAGGTGATCTTGAGTTGAGCACCATCCGCCCATAGTGAGCCAGAGACTGTCAGTTCTCAA
TGGACTACAGATGAGTAGAGCTGGAAGGCCATACCCGTCCATCTTGGAGCCGCCCATCCGCTCACCGAGGTGA
GTCATCCCGAACCTGGAACCTGGATCAGGAGGAACATGTGCCCCACTTCTCTGTCTTGAAGAACACAGTCATAGATGTGGTCTCAAATGGCCATCTCA
AACTCCTCATCCACTTCTCTCGCCCGTTGCCGATATAGTCCGTTGGGCAGCTGATGGGCTCTCAAAGGAGAACA
TCTGGAAGTCATGCCCGCCTTCTTCCGGATAGCTTGACACAGCTCCTTGCCCCATGTCCGGATAGCCGCGGAGCCCCTGATGTCTAGCGCCTCCAT
AGAAGGTACCCTCCCAGACACTCCTTGTGTGCAGATCCATTGGGCAGATCCAATTGGCTGTTCAGCCATGGAAG
GGACCCCTTGCCTTCCTTCTTGCAAGGTTGTCCTTCTTGAGCCGTTGAGCCGTAGAAGGTCCAACCGTGAGCTTCGTGAGCTCAGA
GCCATGGAGTAGTTCTGAAACACCTAGTAGATGTCCTGAGGAGGCCATGAAGAGCTCCACCGAAGGCTCCACAGCA
GTATTCCTGAAACACCTGAGTAGATGTAGGCTGTTACCCTCCAGCACTGTGACACCCACCTGCACCCACCGCCGTA
ATGTCTTCCACAGACAGTCCTGAGAGCCGCTGGTGGTCCATGAGACATAGGCCCGGTCTCGCATCCTGCCTCCACA
TCCCCTTCGCCAGCAGGTTGGCAGCTGATGCGGAAATTTCTCTGTCGTGCCGCATCTCTGATCATGGATTACACTTCA
CGTATATTTAATGCTGATCGGTATCGGTACAGTTCTGCTGGTAACTCCACAGCTCGTGATTTAATGCTTACACAAAATACTTTGTCTTCCAACTTGA
AGCAATCCTTTAGAGAGTTCTCTTTTCAGCCTCTTGGCGTCCTGAAGGGACTCCAGCCGAATGTCACCCTCCTGAGCGACAGCTTCAGCCT
GCTGATGGTTCTCTTTTTCAGCGCCTTTTGATGCGGGTCAGGATCCATAGCCGGGCACCGCCAGCGACAGCTCGATGGTCTCGG
CCCTTTCTGTTAAGGATCTTGGATGCAGCGGAAACCCCCCAGCCCAACCCGCCACCAGGGCTCGCCAGTATTCAGAATAATCTTCCTCCA
CGTAGTTCTTGTTAAGGATCTTGGATCCTGTGCCACCAGGATGGCCGGGCTCCGCTGCCTGGCGCTCGCCAGTATTCAGAGATAATCTTCCTCCA
GGAGTTTCTCATGTCACCTGAAGAGCCACATCCCCGGGGACCTCGACCGTGCGCTGCCCTTCCTCAGTCCCGAGCCT
CCCCTTCAGCCCGTCTGTGCTGAGGGCTTGAGGAGGACCAGCAGGAGAATCGGGTTGCGCGGTGTATAAATTAAC
```

B

```
GCAGCTGGACAGGAAGGTTCTAATGTTCTTAAGGCACAGGAACTGGGACATCTGGGCCCCGAAAGCCTTTTTCTCTGT
GATCCGGTACAGTCCTTCTGC
```

FIG. 35

FIG. 39

FIG. 40

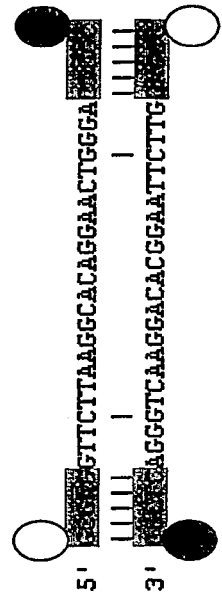
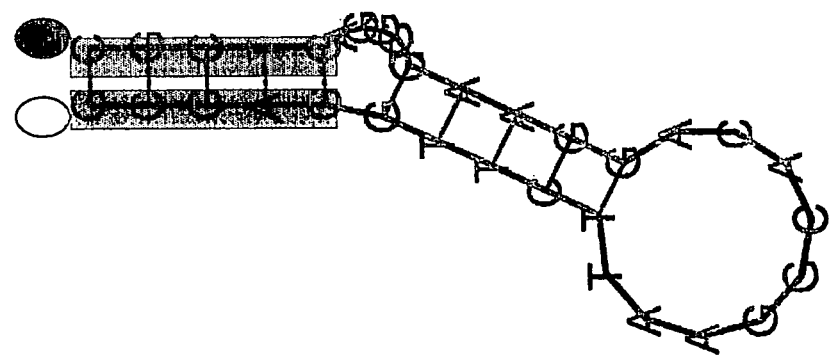
FP18  5' GCGAG GTTCTT AAGGCACAGGAACTGGGA CTCGC 3'
FIG. 41

A  GCAGGTGGACAGGAAGGTTCTAATGTTCTTAAGGCACA
GGAACTGGGAGACATCTGGGCCCGGAAAGCCTTTTCTCT
GTGATCCGGTACAGTCCCTTCTGC

B  GCAGGTGGACAGCTTGGTTCTAATGAAGTTAACCCTGT
CGTTGTCGCGACATCTGGGCCCGGAAAGCCGTTTAACUGA
TGGAUGGAACAGTCCCTTCTGC

C  GCAGGTGGACAGGAAGGTTCTAATGTTCTATAGGGTCT
GCTTGTCGCTCATCTGGGCCCGGAGATGCGT
AAAGTCAGACATCCGGTACAGTCCCTTCTGC

D  1  GTTCTTAAGGCACACAGGAACTGGGA
   2  GAAGTTAACCCTGTGTTCTGCGA    50% different from target 1;

A  start
GCAGGTGGACAGGAAGGTTCTAATGTTCTTAAGGCACAGGAACTGGGACATCTGGGCCCCGAAAGCCTTTTCTCTGTGATCCGGTACAGTCCTTC
TGC B  1
GCAGGTGGACAGCTTGGTTCTAATGAAGTTAACCCTGTCGTTCTGCGACATCTGGGCCCCGAAAGCGTTAACTGACAGATGGGTACAGTCCTTC
TGC C  2
GCAGGTGGACAGCTTGGTTCTAATGAAGTTAACCCTGTCGTTCTGCGACATCTGGGCCCCGAAAGCGTTAAC[TGACA]GATGGGTACAGTCCT
TCTGC D  3
GCAGGTGGACAGCTTGGTTCTAATGAAGTTAACCCTGTCGTTCTGCGACATCTGGGCCCCGAAAGCGTTAAC[[T]]GATGGGTACAGTCCTTC
TGC E  4
GCAGGTGGACAGCTTGGTTCTAATGAAGTTAACCCTGTCGTTCTGCGACATCTGGGCCCCGAAAGCGTTAACTGATGG[[AT]]GGTACAGTCCT
TCTGC F  5
GCAGGTGGACAGCTTGGTTCTAATGAAGTTAACCCTGTGTCTGCGACATCTGGGCCCCGAAAGCGTTAACTGATGATGGAACAGTCCTTCTG
C G  modifications of sequence compared to previous sequence:
1 <u>underlined</u> = change in bases
2 [single bracket] = bases cut out
3 [[double bracket]] = bases added
4 [[double bracket]] = bases added
5 <u>underlined</u> = change in bases

FIG. 43

A start
GCAGGTGGACAGGAAGGTTCTAATGTTCTTAAGGCACAGGAACTGGACAGATCTGGGACAGATCTGGGACCCGGAAAGCCTTTTCTCTGTGATCCGGTACAGTCCTTCTGC B 1
GCAGGTGGACAGGAAGGTTCTAATGTTCTATAGGGTCTGCTTGTCGCTCATCTGGGCCGGAAAGCCTTAAGTCAGACATCCGGTACAGTCCTTCTGC C 2
GCAGGTGGACAGGAAGGTTCTAATGTTCTATAGGGTCTGCTTGTCGCTCATCTGGGCCCGGAAAGCCTTAAAGTCAGACATCCGGTACAGTCCTTCTGC D 3
GCAGGTGGACAGGAAGGTTCTATGTTCTATAGGGTCTGCTTGTCGCTCATCTGGGCCCGGAAAGCCTTAAAGTCAGACATCCGGTACAGTCCTTCTGC E 4
GCAGGTGGACAGGAAGGTTCTAATGTTCTATAGGGTCTGCTTGTCGCTCATCTGGGCCCGGAAAGCGTTAAAGTCAGACATCCGGTACAGTCCTTCTGC F 5
GCAGGTGGACAGGAAGGTTCTAATGTTCTATAGGGTCTGCTTGTCGCTCATCTGGGCCCGGAATGCGTTAAAGTCAGACATCCGGTACAGTCCTTCTGC
AAAGTCAGACATCCGGTACAGTCCTTCTGC[T]

G 6
GCAGGTGGACAGGAAGGTTCTAATGTTCTATAGGGTCTGCTTGTCGCCTCATCTGGGCCCGGA[[G]]ATGCGT
AAAGTCAGACATCCGGTACAGTCCTTCTGC

H  1  underlined = change in bases
   2  underlined = change in bases
   3  underlined = change in bases
   4  underlined = change in bases
   5  [single bracket] = bases cut out
   6  [[double bracket]] = bases added

FIG. 44

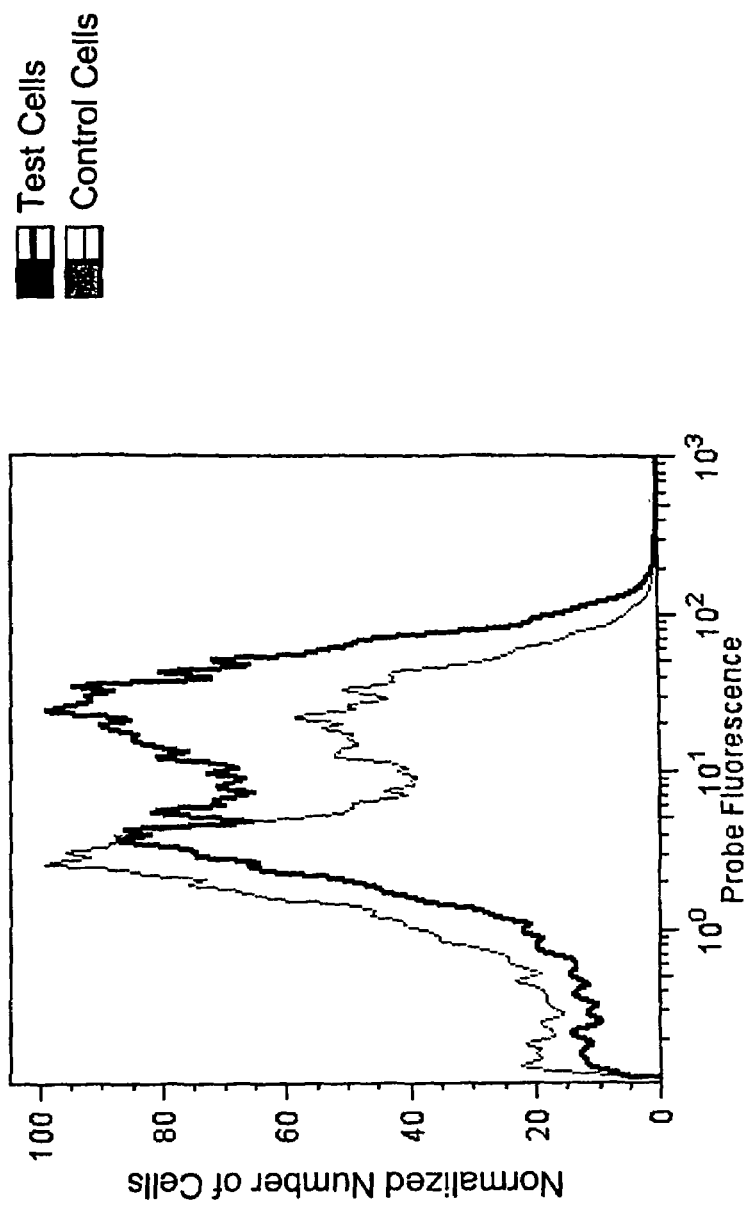
FIG. 46    mcon1

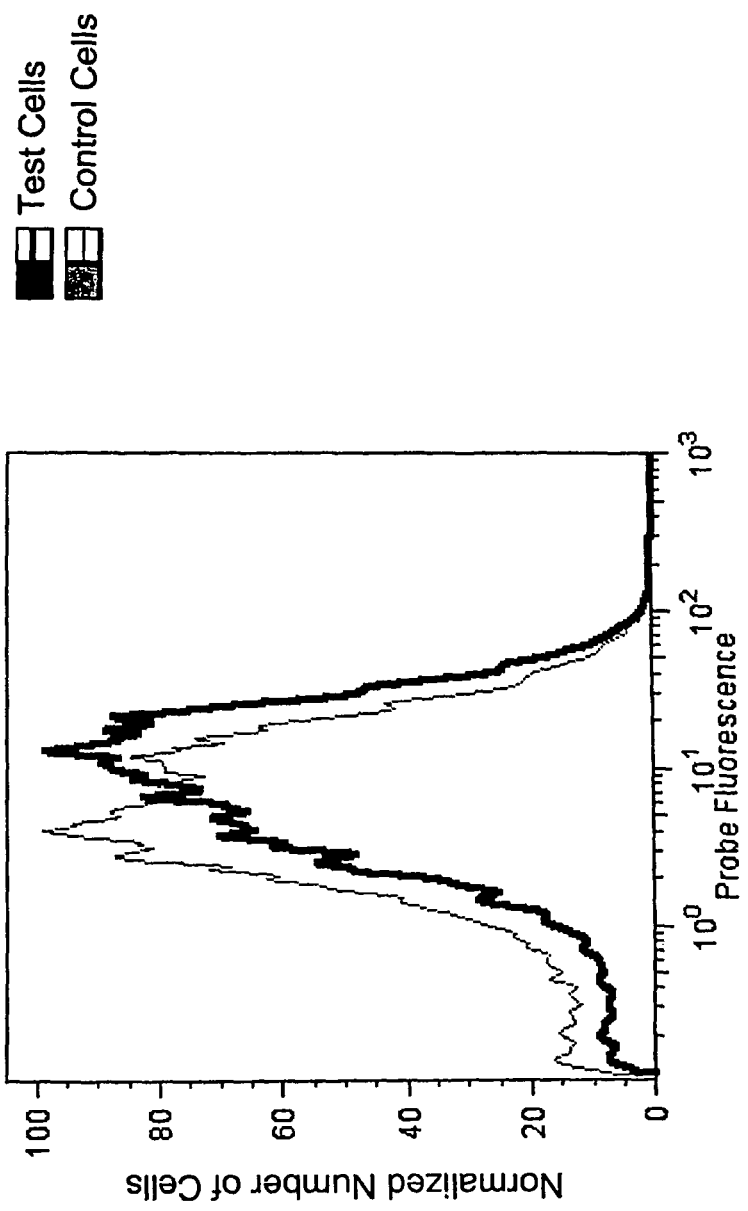
FIG. 47  mcon2

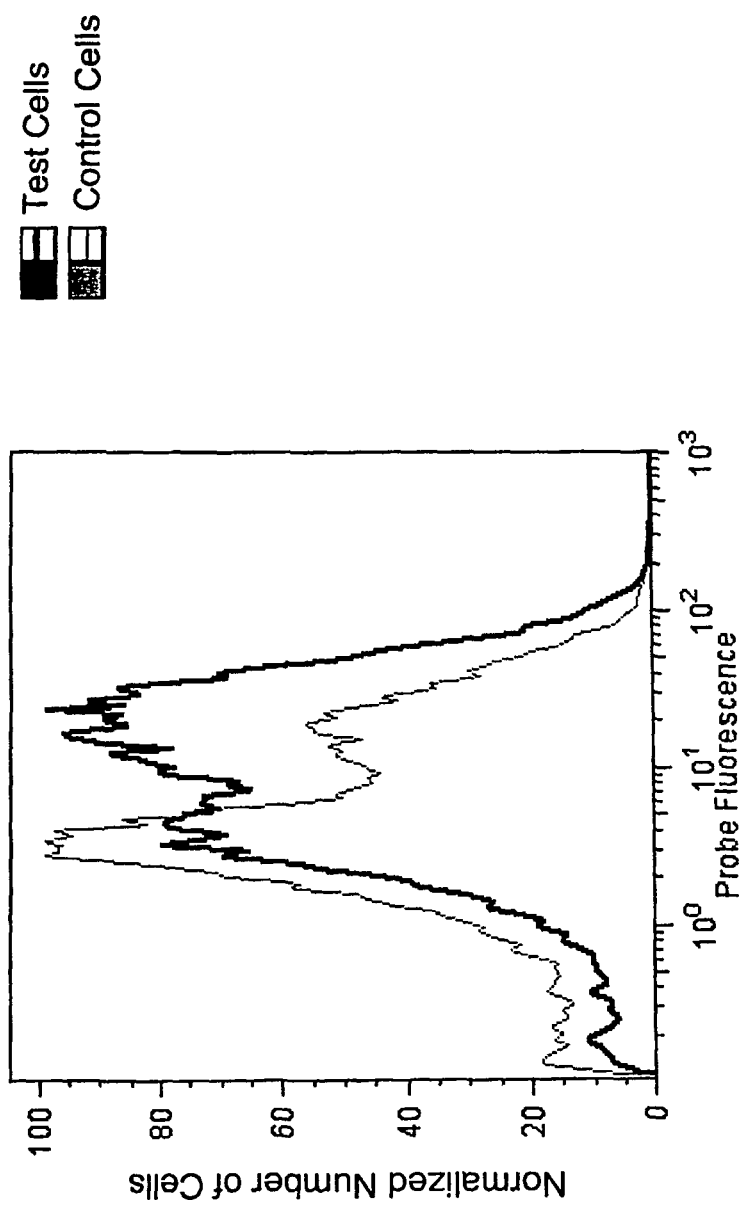
FIG. 48  mcon3

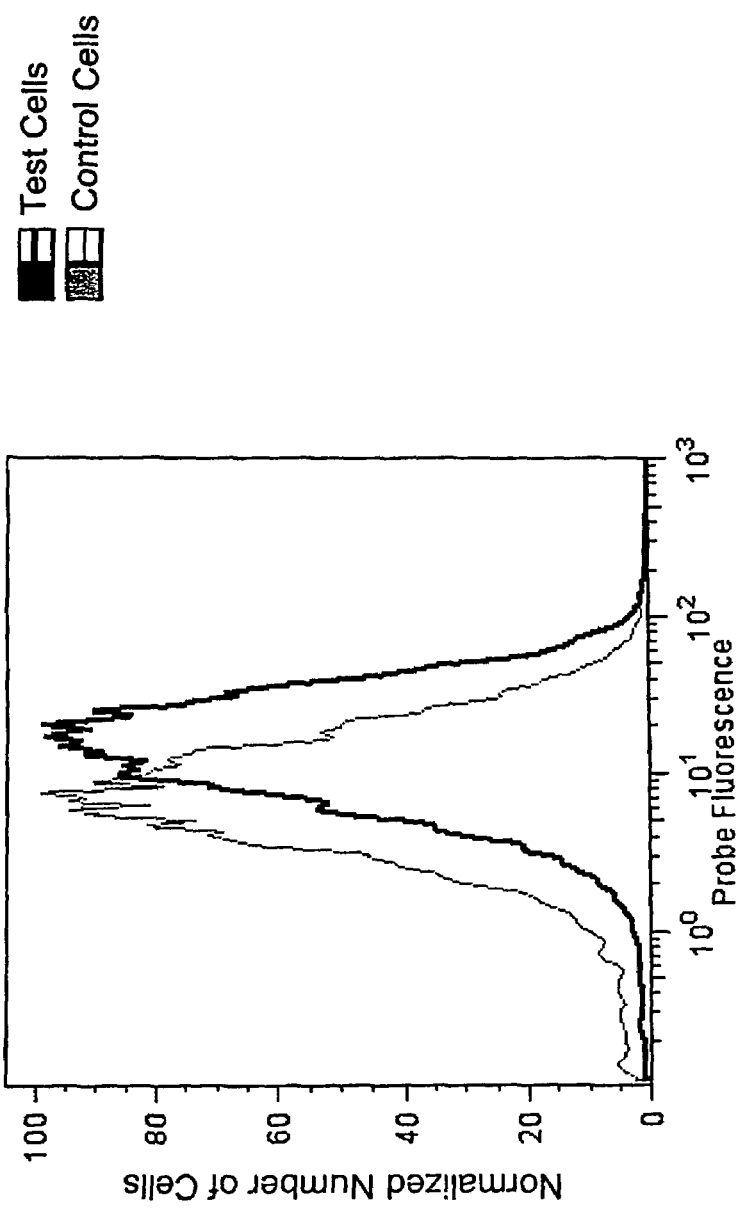
FIG. 49    mcon4

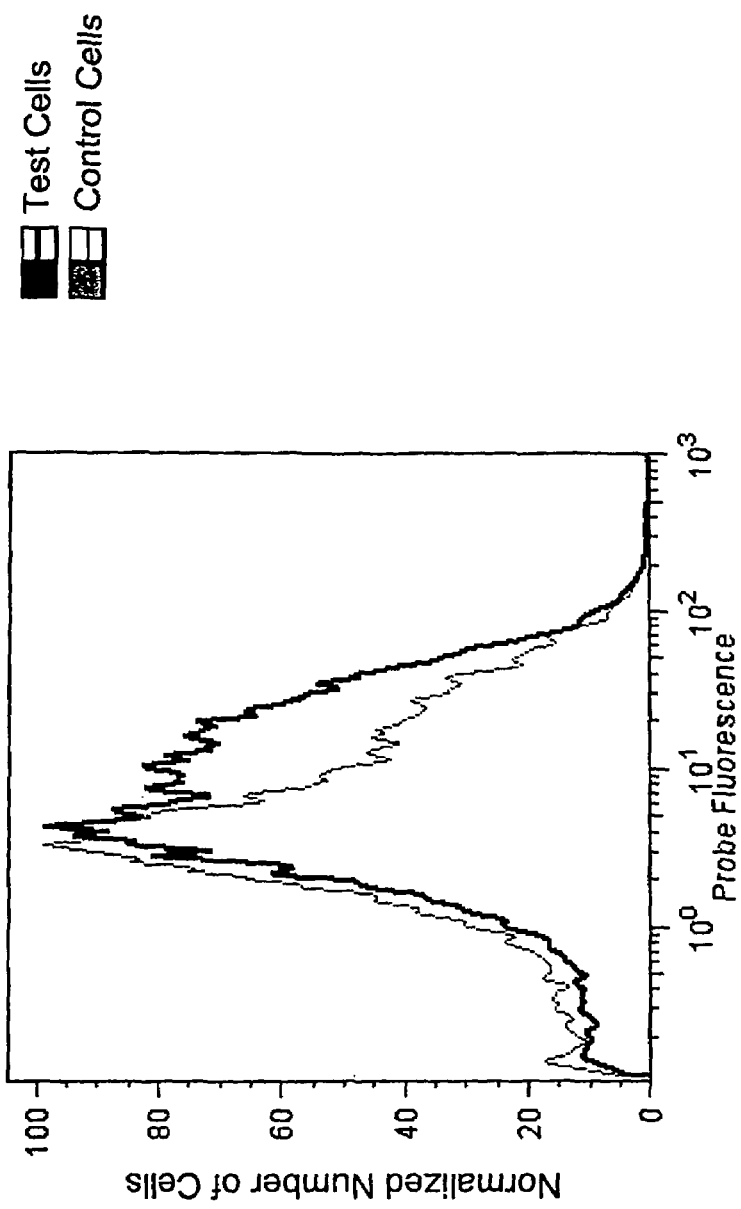
FIG. 50   mcon5

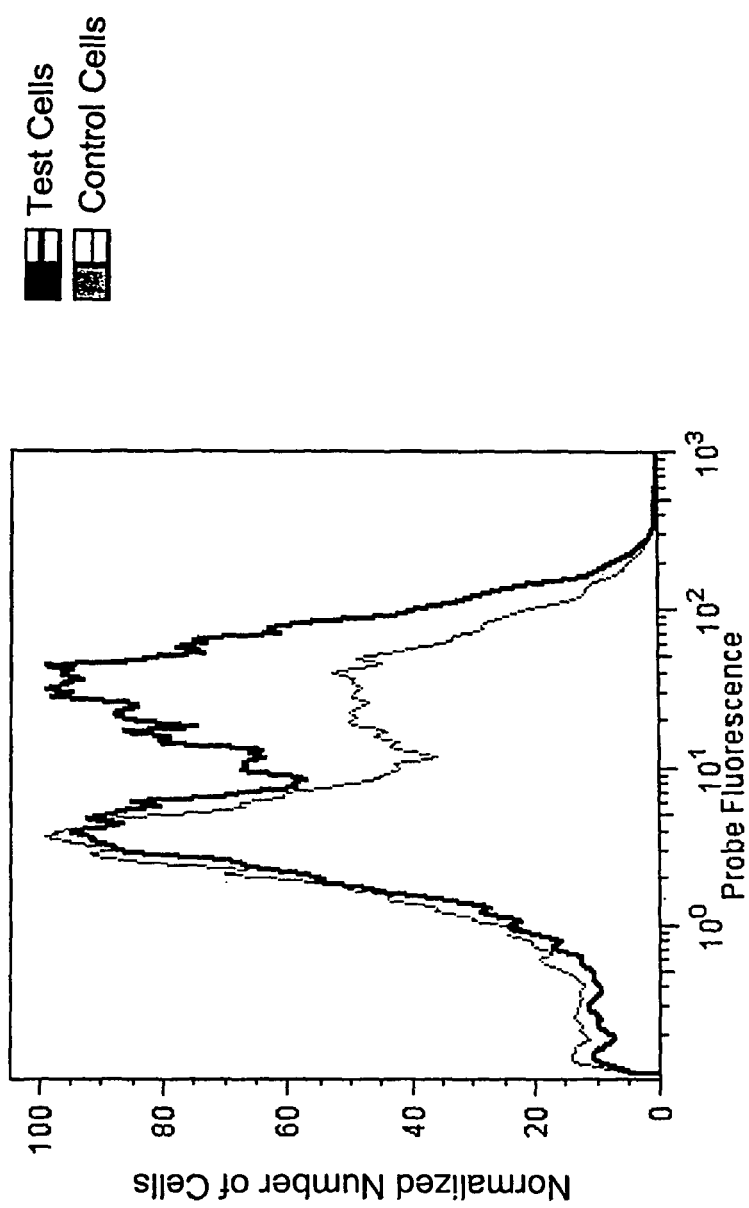
FIG. 51    mcon6

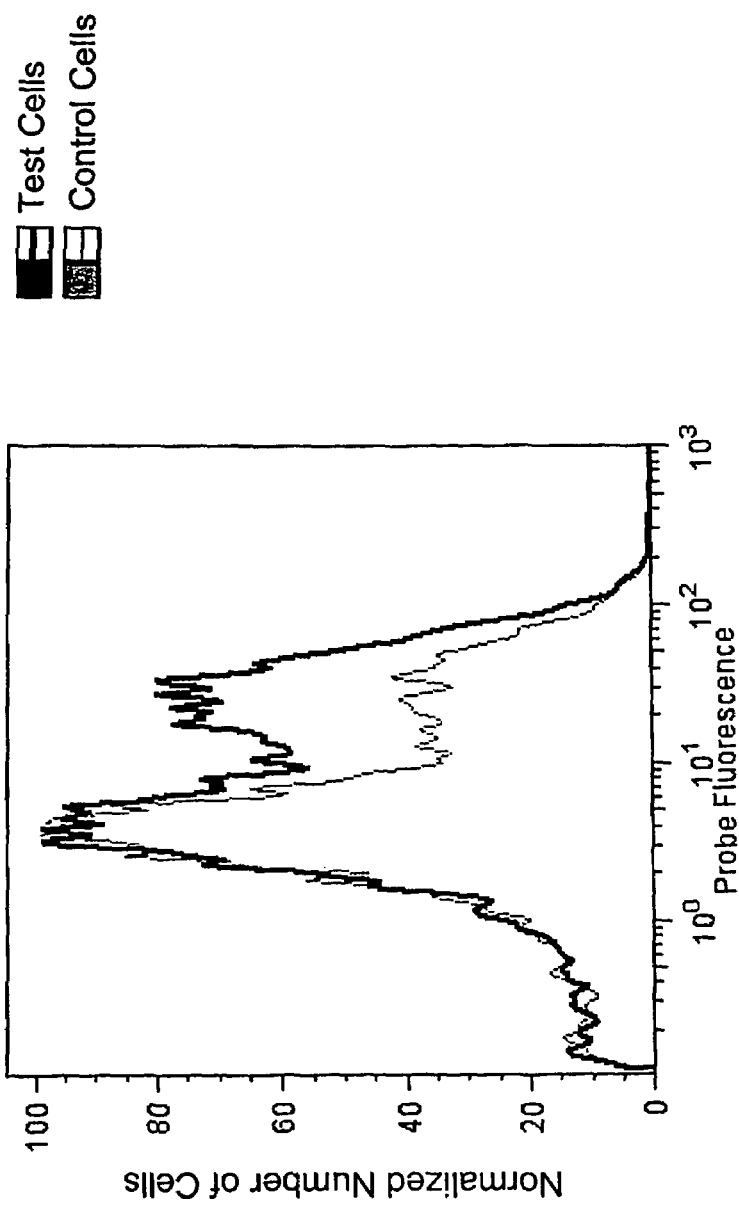
FIG. 52    mcon7

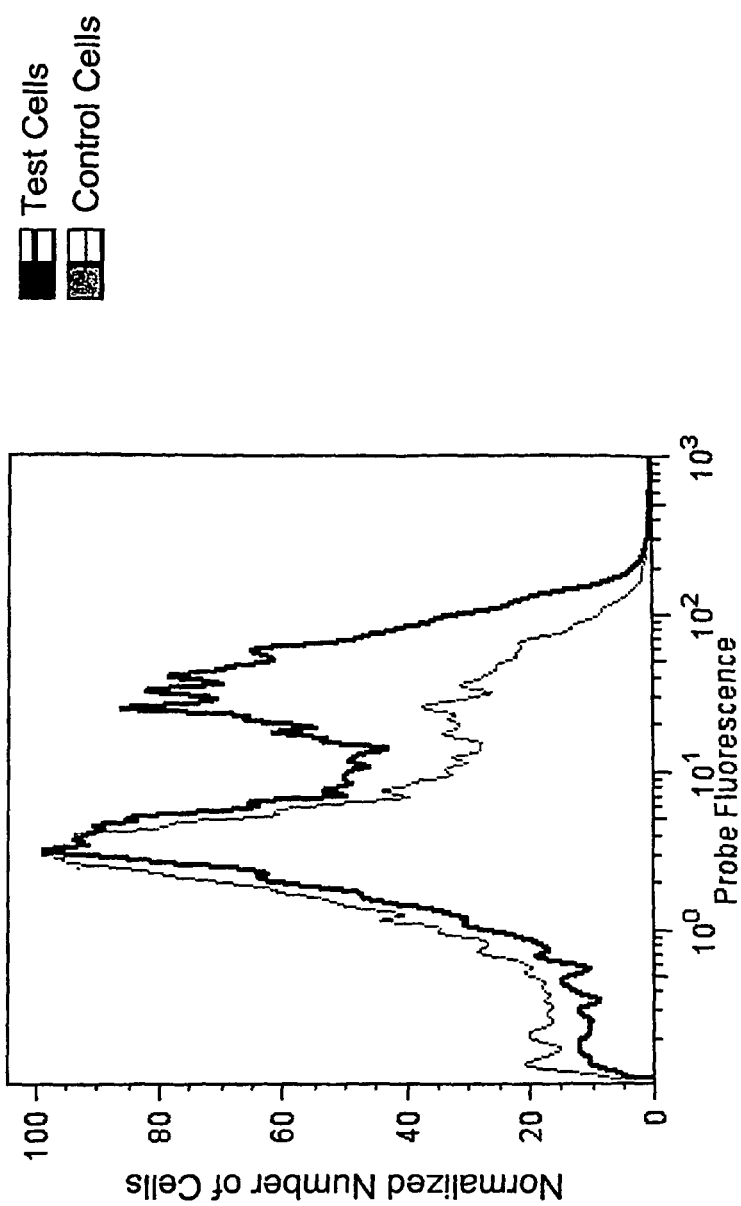
FIG. 53  mcon8

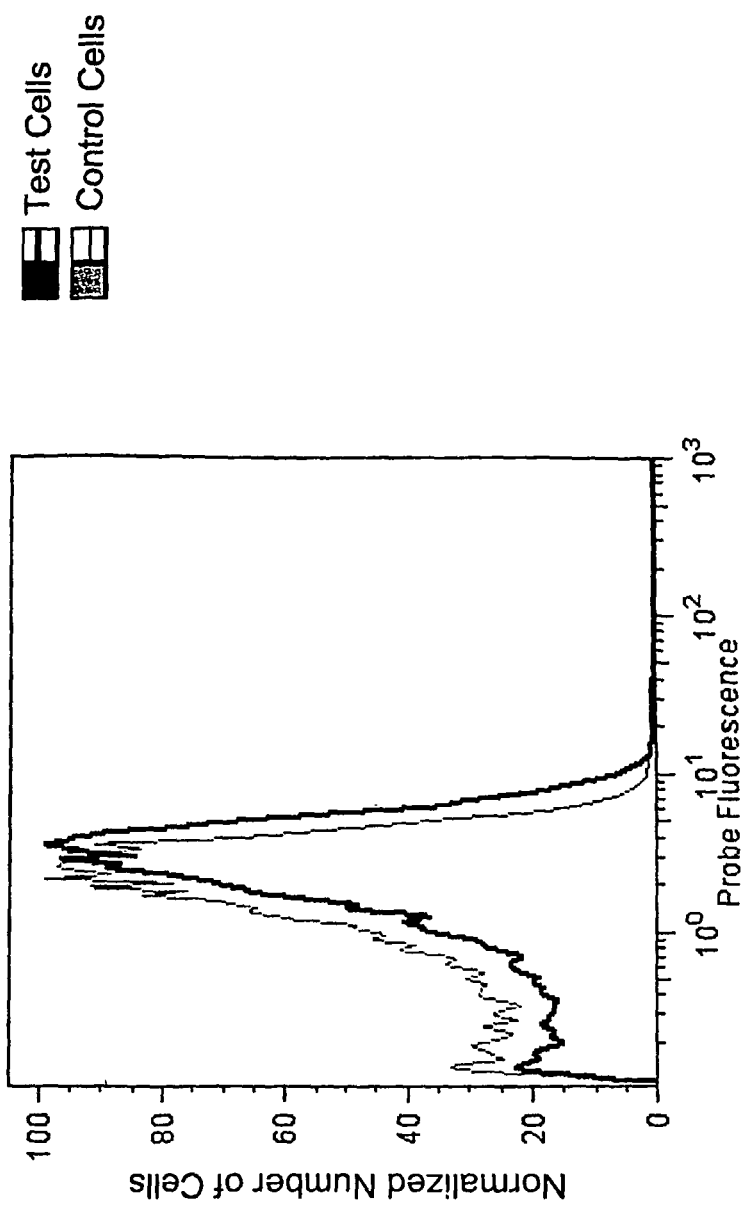
FIG. 54  mcon9

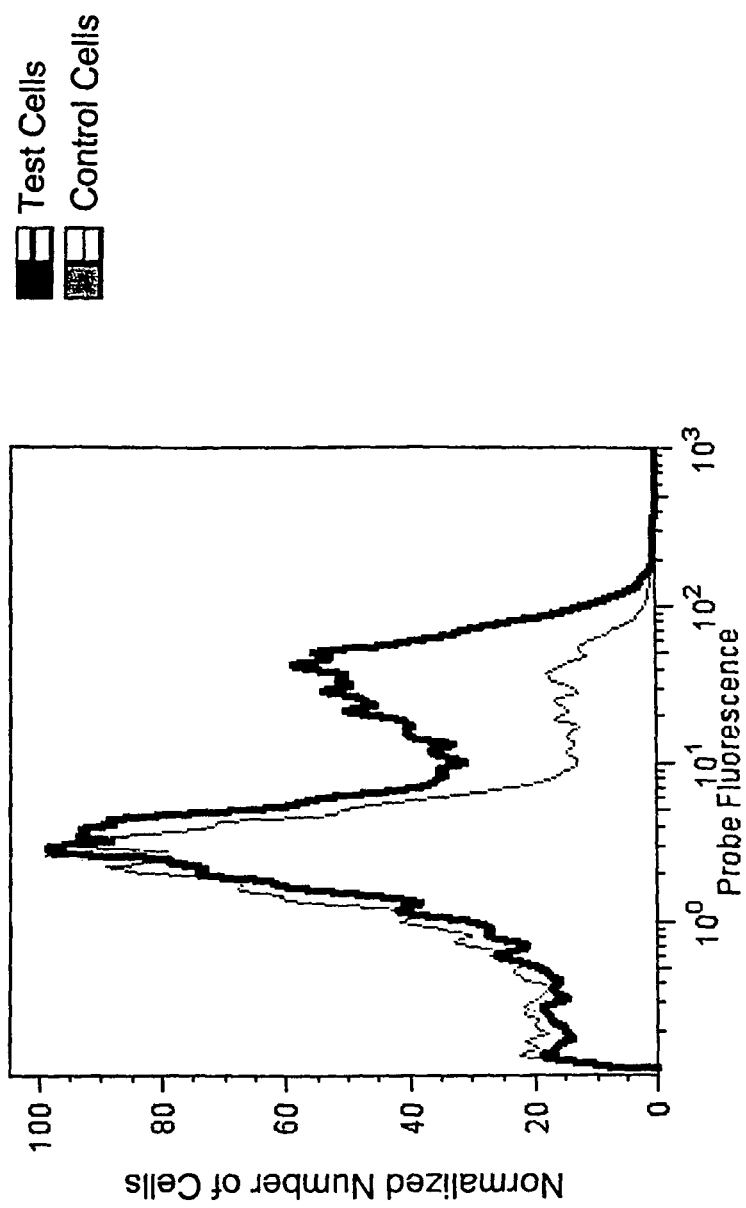
FIG. 55   mcon10

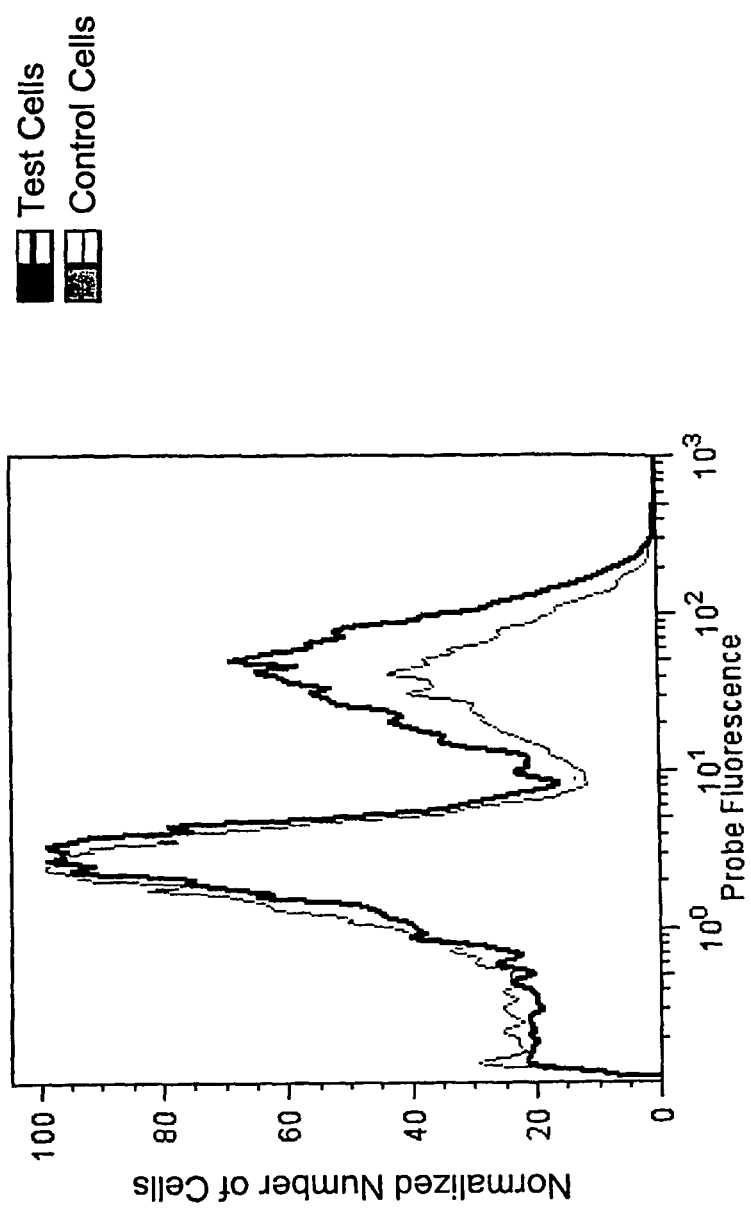
FIG. 56   mcon11

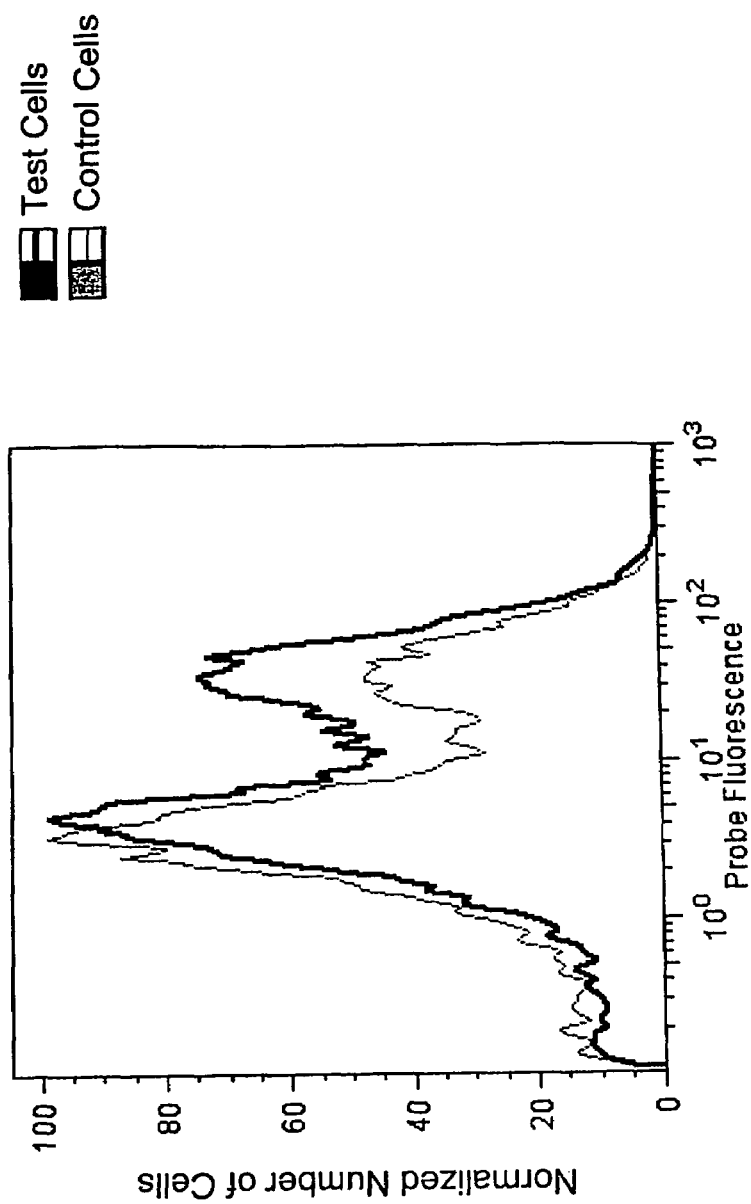
FIG. 57    mcon12

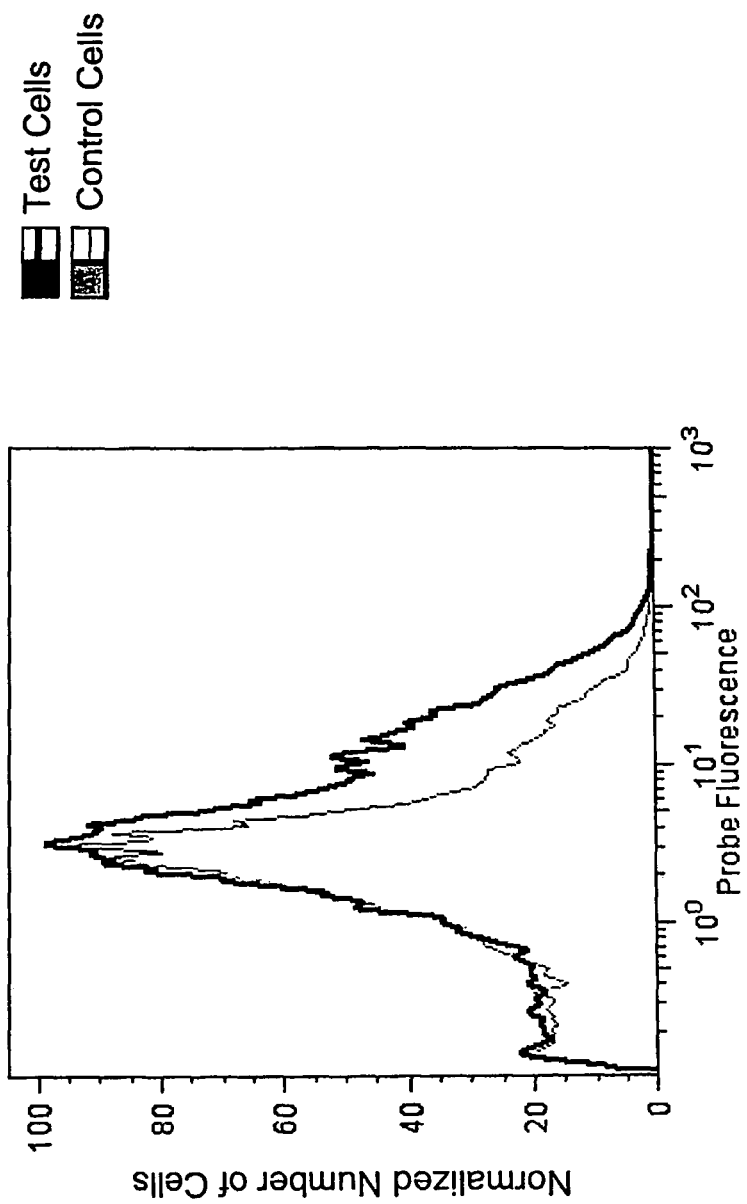
FIG. 58    mcon13

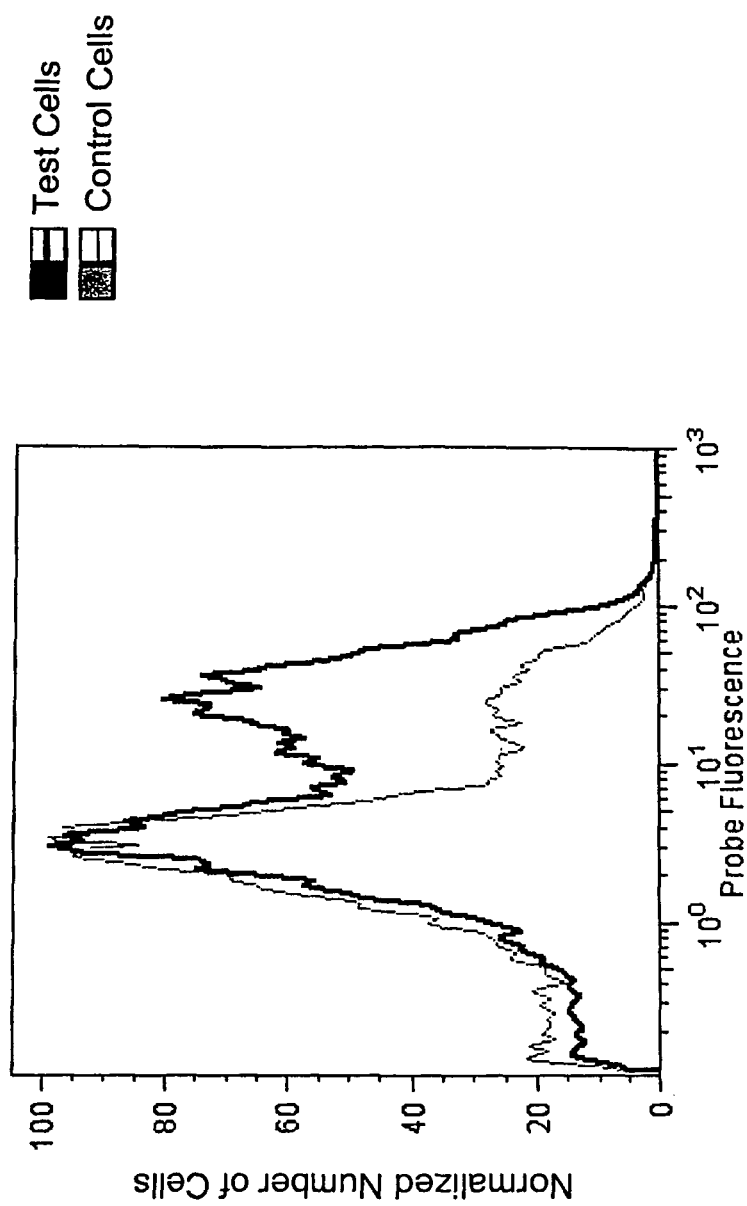
FIG. 59   mcon14

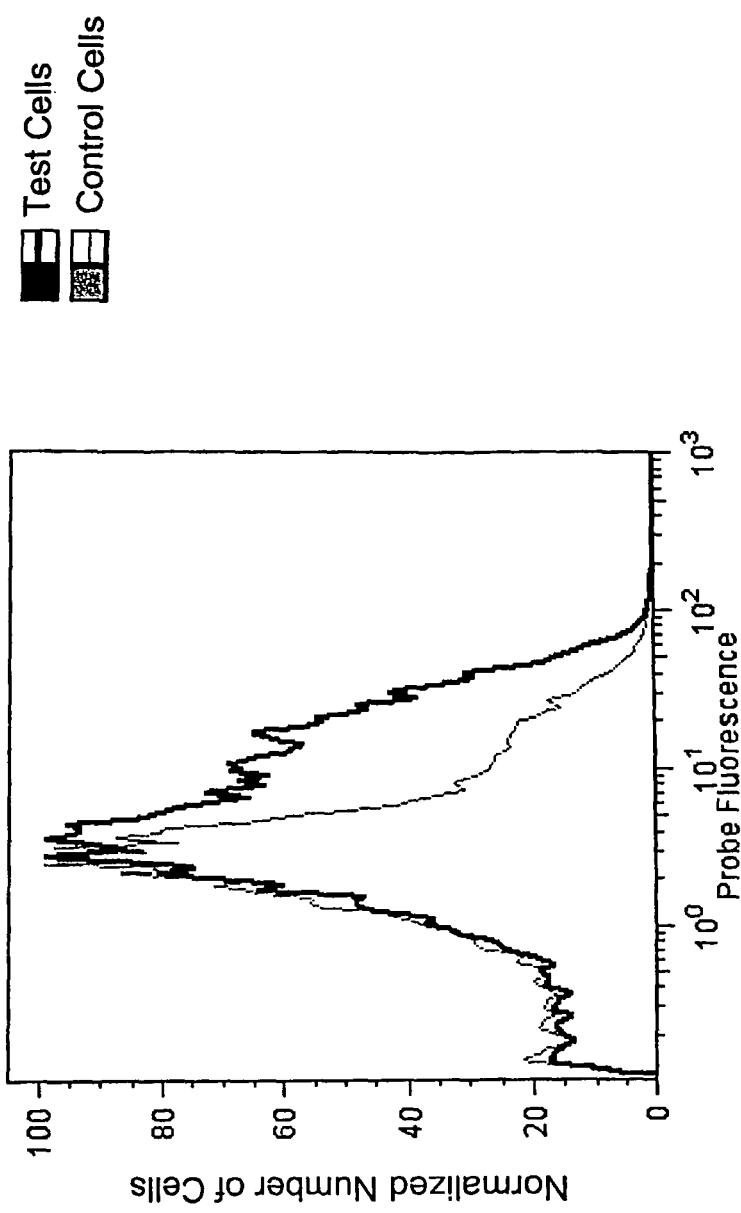
FIG. 60   mcon15

METHODS AND MATERIALS USING SIGNALING PROBES

This application is a national stage entry of International Application No. PCT/US2005/005080, filed Feb. 17, 2005, which claims priority from U.S. Provisional Application No. 60/546,075, filed Feb. 18, 2004. The disclosures of all of the aforementioned priority applications are incorporated by reference in their entirety herein.

BACKGROUND OF THE INVENTION

Nucleic acid probes that recognize and report the presence of a specific nucleic acid sequence have been used to detect specific nucleic acids primarily in in vitro reactions. See, for example, U.S. Pat. No. 5,925,517, incorporated herein by reference. One type of probe is designed to have a hairpin-shaped structure, with a central stretch of nucleotides complementary to the target sequence, and termini comprising short mutually complementary sequences. See, for example, Tyagi and Kramer, *Nature Biotechnology*, 14, 303-308 (1996), incorporated herein by reference. One terminus of the stem-loop shaped probe is covalently bound to a fluorophore and the other to a quenching moiety. When in their native state with hybridized termini, the proximity of the fluorophore and the quencher is such that relatively little or essentially no fluorescence is produced. The stem-loop probe undergoes a conformational change when hybridized to its target nucleic acid that results in the detectable change in the production of fluorescence from the fluorophore. Researchers have used the hairpin-shaped probe to perform in-situ visualization of messenger RNA (Matsuo, 1998, *Biochim. Biophys. Acta* 1379: 178-184) in living cells.

SUMMARY OF THE INVENTION

The present invention provides methods and compositions comprising novel signaling probes for analyzing or isolating cells or generating cell lines expressing one or more RNA. The method is based on the detection of signal produced by the probes upon their hybridization with target sequence. The RNA may be introduced into the cells via a DNA construct, or the cells may be suspected of expressing the RNA endogenously. The DNA construct may further encode a tag sequence, and the signaling probe is complementary to the tag sequence. In one embodiment, the isolated cells, or generated cell lines are functionally null for expression or have reduced expression of one or more preselected proteins or RNAs. The invention also provides a method of generating transgenic animals using cells that are isolated according to the methods described.

The invention provides signaling probes used in a method for quantifying the expression level of one or more RNA transcripts. In addition, the signaling probes are used in a method for identifying a compound or RNA sequence that modulates transcription of at least one preselected RNA. In another embodiment, the signaling probes are used in a method for identifying genetic recombinational events in living cells. The signaling probe comprises one or more strands of nucleotides, wherein the signaling probe comprises nucleotides that are complementary to a target nucleic acid (e.g., RNA) of interest and wherein the signaling probe further comprises an interacting pair comprising two moieties. The structure of the signaling probe is such that when the signaling probe is not hybridized to the target sequence, the two moieties of the interacting pair are physically located such that no or background signal is produced. When the signaling probe is hybridized to the target sequence, the two moieties are such that a signal is produced. Alternatively, the moieties of the signaling probe may be such that when the probe is not hybridized to the target, there is particular signal produced and a different signal is produced upon hybridization of the probe to the target sequence. The two moieties of the interacting pair may be attached to one or more terminus of one or more strands of the signaling probe. Alternatively, the moieties may be internally incorporated into one or more strands of the signaling probe. The nucleotides of the signaling probe may also be modified.

The present invention also provides protease probes. In one embodiment, the signaling or protease probe comprises two separate strands of nucleic acid or modified nucleic acid one or more portions of which anneal to each other, and at least one terminus of one strand is adjacent to a terminus of the other strand. The nucleic acid may be DNA or RNA. For the signaling probe with two separate strands, in one embodiment, one strand has at least a quencher moiety on one terminus, and the other strand has at least a fluorophore on the adjacent terminus. For the protease probe, in one embodiment, one strand has at least a proteolytic enzyme on one terminus, and the other strand has at least an inhibitor of the proteolytic enzyme on the adjacent terminus.

In another embodiment, the signaling or protease probe is designed to comprise at least a mutually complementary region and at least a non-complementary region. In one embodiment, at least one non-complementary region may be designed to form a loop region. In one embodiment, the probe is designed to form at least a stem-loop structure. In another embodiment, the probe forms a dumbbell structure or a three-arm junction structure. In one embodiment, the signaling probe has at least a fluorophore and at least a quencher moiety at each terminus of the strand. In one embodiment, the protease probe has a proteolytic enzyme and an inhibitor of the proteolytic enzyme at each terminus of the strand.

In another embodiment, the signaling or protease probe is chemically modified. One or more of the sugar-phosphodiester type backbone, 2'OH and purine or pyrimidine base is modified. In one embodiment, the deoxyribose backbone is replaced by peptide nucleic acid In one embodiment, the tag sequence is a structural RNA, i.e., the RNA has secondary structure, preferably a three-arm junction structure. In one embodiment, the tag sequence comprises the structure or sequence according to FIG. 42 A, B or C. The present invention also provides a DNA construct comprising at least one DNA encoding at least one RNA of interest and the tag sequence. The invention also provides vectors and cells comprising the DNA construct.

In other embodiments is provided:

1. A method for isolating cells expressing at least one RNA, comprising the steps of:
   a) introducing into cells at least a DNA encoding at least one RNA;
   b) exposing said cells to at least one signaling probe that produces a detectable signal upon hybridization to said at least one RNA; and
   c) isolating said cells that produce the signal.

2. The method of paragraph 1, further comprising the step of generating a cell line or a plurality of cell lines that express said at least one RNA by growing said isolated cells.

3. A method for isolating cells that express at least one of two or more RNAs, comprising the steps of:
   a) introducing into cells a first DNA encoding a first RNA;
   b) introducing into said cells at least a second DNA encoding at least a second RNA;

c) exposing said cells to at least a first signaling probe that produces a detectable signal upon hybridization to said first RNA;
d) exposing said cells to at least a second signaling probe that produces a detectable signal upon hybridization to said at least second RNA; and
e) isolating cells that produce at least one of said signals upon hybridization of said signaling probes to their respective RNAs.

4. The method of paragraph 3 further comprising the step of generating a cell line or a plurality of cell lines that express at least one of said two or more RNAs by growing said isolated cells.

5. A method for isolating a plurality of cells, wherein at least a portion of the cells express at least a different RNA, comprising the steps of:
a) introducing into cells a plurality of DNA encoding a plurality of RNA, wherein at least a portion of the cells are introduced at least a different DNA that encodes at least a different RNA;
b) exposing said cells to a plurality of signaling probes sequentially or simultaneously, wherein the signaling probes produce a detectable signal upon hybridization to said plurality of RNA; and
c) isolating said cells that produce the signal.

6. The method of paragraph 5 further comprising the step of generating a plurality of cell lines expressing at least a different RNA by growing said isolated cells.

7. A method for isolating cells expressing at least one RNA, comprising the steps of:
a) introducing into cells at least a DNA encoding said at least one RNA and at least one tag sequence;
b) exposing said cells to at least one signaling probe that produces a detectable signal upon hybridization with the tag sequence; and
c) isolating said cells that produce the signal.

8. The method of paragraph 7, further comprising the step of generating a cell line or a plurality of cell lines that express said at least one RNA by growing said isolated cells.

9. A method for isolating cells expressing at least one of two or more RNAs, comprising the steps of:
a) introducing into cells a first DNA encoding a first RNA and at least a first tag sequence;
b) introducing into said cells at least a second DNA encoding at least an additional RNA and at least a second tag sequence, wherein the second tag sequence is the same or different from the first tag sequence;
c) exposing said cells to at least a first signaling probe that produces a detectable signal upon hybridization with the first tag sequence;
d) exposing said cells to at least a second signaling probe that produces a detectable signal upon hybridization with the second tag sequence; and
e) isolating cells that produce at least one of said signals upon hybridization of said signaling probes to their respective RNAs.

10. The method of paragraph 9 further comprising the step of generating a cell line or a plurality of cell lines that express at least one of said two or more RNAs by growing said isolated cells.

11. The method of paragraph 3 or 9, wherein said steps of said first RNA are performed either simultaneously or sequentially with the corresponding steps of said at least one additional RNA.

12. The method of paragraph 3 or 9, wherein the two or more RNAs or proteins encoded by the two or more RNAs are selected from the group consisting of RNAs or proteins in the same or related biological pathway, RNAs or proteins that act upstream or downstream of each other, RNAs or proteins that have a modulating, activating or repressing function to each other, RNAs or proteins that are dependent on each other for function or activity, RNAs or proteins that form a complex, proteins from a protein family.

13. A method of isolating cells that overexpress at least one RNA comprising the steps of:
a) introducing into cells at least a first DNA encoding said at least one RNA and at least a first tag sequence; and at least a second DNA encoding said at least one RNA and at least a second tag sequence, wherein the introduction of the first and second DNA construct is performed sequentially or simultaneously, wherein the first and second tag sequences are the same or different;
b) exposing said cells to at least a first signaling probe that produces a detectable signal upon hybridization with said at least first tag sequence, and to at least a second signaling probe that produces a detectable signal upon hybridization with said at least second tag sequence; and
c) isolating cells that produce at least one of said signals upon hybridization of said signaling probes to their respective RNAs.

14. The method of paragraph 13 further comprising the step of generating a cell line or a plurality of cell lines that overexpress said RNA by growing said isolated cells.

15. The method of any one of paragraphs 3, 9 and 13, wherein the first signaling probe produces a different signal than the signal produced by the second signaling probe.

16. The method of paragraph 13, wherein said steps of said first signaling probe are performed either simultaneously or sequentially with the corresponding steps of said second signaling probe.

17. The method of any one of paragraphs 3, 9 and 13, wherein said first DNA and said second DNA are on the same construct or different constructs.

18. A method for isolating a plurality of cells, wherein at least a portion of the cells express at least a different RNA, comprising the steps of:
a) introducing into cells a plurality of DNA encoding a plurality of RNA and at least one tag sequence, wherein at least a portion of the cells are introduced at least a different DNA that encodes at least a different RNA;
b) exposing said cells to at least one signaling probe that produces a detectable signal upon hybridization to said tag sequence; and
c) isolating said cells that produce the signal.

19. The method of paragraph 18, wherein the plurality of RNA form at least an expression library.

20. The method of paragraph 18, further comprising the step of generating a plurality of cell lines expressing at least a different RNA by growing said isolated cells.

21. A method of isolating at least one of two or more RNA expression libraries of cells, comprising the steps of:
a) introducing into cells DNA encoding at least a first RNA expression library and at least a first tag sequence;
b) introducing into cells DNA encoding at least a second RNA expression library and at least a second tag sequence, wherein the second tag sequence is the same or different from the first tag sequence;
c) exposing said cells to at least a first signaling probe that produces a detectable signal upon hybridization to said at least first tag sequence;
d) exposing said cells to at least a second signaling probe that produces a detectable signal upon hybridization to said at least second tag sequence, wherein the detectable signal from the first signaling probe is the same or different from the detectable signal from the second signaling probe; and
e) isolating said cells that produce at least one of said signal.

22. The method of paragraph 21, further comprising the step of generating at least one of said two or more RNA expression libraries by growing said isolated cells.

23. The method of paragraph 5 or 18, wherein the plurality of RNA or proteins encoded by the plurality of RNAs are selected from the group consisting of RNAs or proteins in the same or related biological pathway, RNAs or proteins that act upstream or downstream of each other, RNAs or proteins that have a modulating, activating or repressing function to each other, RNAs or proteins that are dependent on each other for function or activity, RNAs or proteins that form a complex, proteins from a protein family.

24. The method of paragraph 18, wherein at least a portion of the plurality of DNA encode the same tag sequence.

25. The method of paragraph 7, 9, 13, 18 or 21, wherein the tag sequence comprises multiple target sequences to be recognized by at least a signaling probe.

26. The method of any one of paragraphs 7, 9, 13, 18 and 21, wherein the tag sequence is a structural RNA.

27. The method of paragraph 25, wherein the tag sequence forms a three-arm junction structure.

28. The method of paragraph 27, wherein the stem region comprises 8-9 basepairs, the first stem-loop region comprises 4-6 basepairs and the second stem-loop region comprises 13-17 basepairs.

29. The method of paragraph 27, wherein the stem regions of the three arms further comprise non-complementary regions.

30. The method of paragraph 27, wherein the stem region and the first stem-loop region both further comprise one mismatch region, and the second stem-loop region further comprises 2-7 mismatch or bulge regions.

31. The method of paragraph 27, wherein the linkage between the stem regions has a total of 8-12 nucleotides.

32. The method of paragraph 26, wherein the tag sequence is selected from the group consisting of the sequences shown in FIGS. 42A, B and C.

33. The method of paragraph 32, wherein the tag sequence forms the more energetically favorable structures predicted by the sequences shown in FIG. 42A, B or C.

34. The method of paragraph 27, wherein the target sequence is the region from all or part of the 3' side of the stem of the first stem-loop region, to the linkage between the first and second stem-loop region, to all or part of the 5' side of the stem of the second stem-loop region.

35. The method of any one of paragraphs 7, 9, 13, 18 and 21, wherein at least a portion of the DNA encode multiple identical tag sequences.

36. The method of paragraph 35, wherein at least a portion of the DNA encode up to 50 identical tag sequences.

37. The method of any one of paragraphs 7, 9, 13, 18 and 21, wherein the DNA encoding said tag sequence is in frame with the DNA encoding said RNA.

38. The method of any one of paragraphs 7, 9, 13, 18 and 21, wherein the DNA encoding said tag sequence is out of frame with the DNA encoding said RNA.

39. A method for isolating cells expressing at least one RNA comprising the steps of:
a) providing cells potentially expressing said at least one RNA;
b) exposing said cells to at least one signaling probe that produces a detectable signal upon hybridization with said at least one RNA;
c) isolating said cells that produce the signal.

40. The method of paragraph 39, further comprising the step of generating a cell line or a plurality of cell lines that express said at least one RNA by growing said isolated cells.

41. The method of paragraph 39, wherein said cells further potentially express one or more additional RNA, further comprising the steps of:
a) exposing said cells to at least one additional signaling probe that produces a detectable signal upon hybridization with said at least one additional RNA; and
b) isolating cells that produce the signal.

42. The method of paragraph 41, further comprising the step of generating a cell line or a plurality of cell lines that express said at least one RNA and additional RNA by growing said isolated cells.

43. The method of any one of paragraphs 1, 3, 5, 7, 9, 13, 18, and 21 further comprising the step of adding to the cells a compound that modulates or regulates the expression of said RNA, additional RNA or plurality of RNA prior to step a).

44. The method of paragraph 43, wherein the compound induces the expression of said RNA, additional RNA or plurality of RNA.

45. The method of paragraph 5 or 18, wherein said steps of said plurality of RNA are performed either simultaneously or sequentially.

46. A method for isolating cells expressing at least one exogenous RNA and at least one endogenous RNA, comprising the steps of:
a) introducing into cells DNA encoding said at least one exogenous RNA, wherein said cells potentially express at least one endogenous RNA;
b) exposing said cells to at least a first signaling probe that produces a detectable signal upon hybridization to said at least one exogenous RNA;
c) exposing said cells to at least a second signaling probe that produces a detectable signal upon hybridization to said at least one endogenous RNA; and
d) isolating said cells that produce at least one of said signals upon hybridization of said signaling probes to their respective RNAs.

47. The method of paragraph 46, further comprising the step of generating a cell line or a plurality of cell lines expressing said at least one exogenous RNA, or said at least one endogenous RNA, or both, by growing said isolated cells.

48. The method of paragraph 46, wherein said steps of said exogenous RNA are performed either simultaneously or sequentially with the corresponding steps of said endogenous RNA.

49. The method of paragraph 46, wherein said second signaling probe produces a different signal than the signal produced by the first signaling probe.

50. The method of paragraph 46, wherein the endogenous RNA and the exogenous RNA or proteins encoded by the endogenous and exogenous RNAs are selected from the group consisting of RNAs or proteins in the same or related biological pathway, RNAs or proteins that act upstream or downstream of each other, RNAs or proteins that have a modulating, activating or repressing function to each other, RNAs or proteins that are dependent on each other for function or activity, RNAs or proteins that form a complex, proteins from a protein family.

51. The method of any one of paragraphs 1, 3, 5, 7, 9, 13, 18, 21 and 39, wherein the RNA comprises one or more of a messenger RNA that encodes a protein, an RNA that encodes a peptide, an antisense RNA, a siRNA, a tRNA, a structural RNA, a ribosomal RNA, an hnRNA and an snRNA.

52. The method of paragraph 51, wherein said protein is selected from the group consisting of a cell surface-localized protein, secreted protein and an intracellular protein.

53. A method for isolating cells that overexpress at least a first protein and which are functionally null expressing or reduced in expression for at least a second protein, comprising the steps of:
   a) introducing into cells at least a first DNA encoding at least one RNA that encodes said at least first protein, and at least a first tag sequence; and at least a second DNA encoding said at least one RNA and at least a second tag sequence, wherein said first and second tag sequences are different;
   b) introducing into cells at least one DNA encoding at least one antisense RNA or siRNA that binds to or interferes with the mRNA transcript of said at least second protein;
   c) exposing said cells to at least a first signaling probe that produces a detectable signal upon hybridization with said at least first tag sequence, and to at least a second signaling probe that produces a detectable signal upon hybridization with said at least second tag sequence;
   d) exposing said cells to at least one signaling probe that produces a detectable signal upon hybridization to said at least one antisense RNA or siRNA; and
   e) isolating cells that produce at least one of said signals upon hybridization of said signaling probes to their respective RNAs.

54. The method of paragraph 53, further comprising the step of generating a cell line or a plurality of cell lines overexpressing at least a first protein and which are functionally null expressing or reduced in expression for at least a second protein.

55. The method of paragraph 53, wherein said steps of said first protein are performed either simultaneously or sequentially with the corresponding steps of said second protein.

56. The method of any one of paragraphs 1, 3, 5, 7, 9, 13, 18, 21, 39 and 53, wherein said DNA is operably linked to a conditional promoter.

57. The method of paragraph 56, wherein the promoter is inducible or repressible, and prior to step (a), a minimal amount of an inducer or a sufficient amount of repressor is added to the cells.

58. The method of paragraph 57, wherein the RNA is antisense RNA or siRNA.

59. The method of paragraph 57, wherein the RNA is lethal or damaging to the cell.

60. The method of any one of paragraphs 1, 3, 5, 7, 9, 13, 18, 21, 39 and 53, further comprising the step of selecting the cells after introducing the DNA into cells but prior to exposing said cells to said signaling probe.

61. The method of any one of paragraphs 1, 3, 5, 7, 9, 13, 18, 21, 39 and 53, wherein at least one DNA further encodes at least one drug resistance marker, and said method further comprises the step of selecting cells resistant to at least one drug to which said marker confers resistance.

62. A method of isolating cells comprising a DNA construct encoding an RNA sequence that is under the control of a tissue specific promoter, comprising the steps of:
   a) introducing into cells at least one DNA construct encoding at least a first RNA sequence under the control of a constitutive promoter and encoding at least a second RNA sequence under the control of a tissue specific promoter;
   b) exposing said cells to at least one signaling probe that produces a detectable signal upon hybridization to said first RNA sequence; and
   c) isolating said cells that produce said signal.

63. The method of paragraph 62, further comprising the steps of generating a cell line or a plurality of cell lines that comprises a DNA construct encoding an RNA sequence that is under the control of a tissue specific promoter.

64. The method of paragraph 62, wherein the tissue specific promoter controls expression of a selection marker gene.

65. The method of paragraph 62, wherein the selection marker gene is a drug resistance gene or a detectable protein gene.

66. A method of identifying a compound that activates a tissue specific promoter, comprising the steps of:
   a) adding a compound to the cells isolated from paragraph 62;
   b) identifying the cells by the selection marker;
   c) identifying the compound as a compound that activates the tissue specific promoter.

67. A method of isolating cells comprising a DNA construct encoding at least a test RNA sequence and an RNA sequence that is under the control of a tissue specific promoter, comprising the steps of:
   a) introducing into cells at least one DNA construct encoding at least one test RNA sequence under the control of a constitutive promoter, at least a second RNA sequence under the control of a second constitutive promoter that is identical or different, and at least a third RNA sequence under the control of a tissue specific promoter;
   b) exposing said cells to at least one signaling probe that produces a detectable signal upon hybridization to said second RNA sequence; and
   c) isolating said cells that produce said signal.

68. The method of paragraph 67, further comprising the steps of generating a cell line or a plurality of cell lines that comprises a DNA construct encoding at least a test RNA sequence and an RNA sequence that is under the control of a tissue specific promoter.

69. The method of paragraph 67, wherein the test RNA sequence is from an expression library.

70. The method of paragraph 67, wherein the tissue specific promoter controls expression of a selection marker gene.

71. The method of paragraph 67, wherein the selection marker gene is a drug resistance gene or a detectable protein gene.

72. A method of identifying a test RNA sequence that activates a tissue specific promoter, comprising the steps of:
   a) identifying the isolated cells of paragraph 67 by the selection marker;
   b) identifying the test RNA sequence that activates the tissue specific promoter.

73. The method of any one of paragraphs 1, 3, 5, 7, 9, 13, 18, 21, 39 and 53, further comprising the steps of
   i) exposing said isolated cells to a signaling probe that produces a detectable signal upon hybridization to the respective RNA;
   ii) determining whether the isolated cells express the respective RNAs; or quantitating the level of the signal to determine the level of expression of the respective RNAs.

74. The isolated cells obtained from the method of any one of paragraphs 1, 3, 5, 7, 9, 13, 18, 21, 39 and 53, wherein the cells are applied in a cell-based assay.

75. The isolated cells obtained from any one of paragraphs 1, 3, 5, 7, 9, 13, 18, 21, 39 and 53, wherein the cells are implantable in an animal.

76. A method for generating a transgenic animal that expresses the RNA according to any one of paragraphs 1, 3, 5, 7, 9, 13, 18, 21, 39 and 53, comprising carrying out the steps of any one of paragraphs 1, 3, 5, 7, 9, 13, 18, 21, 39 and 53 utilizing embryonic stem cells or cells that can be implanted in an animal, determining the viability of said stem cells or cells, and using said viable embryonic stem cells or cells to produce said transgenic animal.

77. The method of paragraphs 1, 3, 5, 7, 9, 13, 18, 21 and 39, wherein the RNA is an antisense RNA or siRNA, and at least one preselected protein in the isolated cells is functionally null or has a reduced expression level as a result of the binding of the antisense RNA, or the interference of the siRNA to mRNA transcripts of said at least one preselected protein.

78. The method of paragraph 77, wherein said preselected protein is an alternatively spliced form of a gene product.

79. A method for generating a transgenic animal, wherein at least one preselected protein is functionally null-expressing or is reduced in expression, comprising carrying out the steps of paragraph 77, utilizing embryonic stem cells or cells that are implantable in an animal, determining the viability of said stem cells or cells, and using said viable embryonic stem cells or cells to produce said transgenic animal.

80. A method for quantifying the level of at least one RNA transcript expression in a biological sample comprising the steps of:
  a) exposing said biological sample to a first signaling probe which produces a detectable signal upon hybridization with said RNA transcript;
  b) quantitating the level of the signal in said biological sample; and
  c) correlating said level of signal with said level of said at least one mRNA transcript.

81. The method of paragraph 80, wherein said biological sample is a cellular sample, a tissue sample or preparations derived thereof.

82. The method of paragraph 80 wherein said RNA transcript is one or more of a messenger RNA that encodes a protein, an RNA that encodes a peptide, an antisense RNA, a siRNA, a tRNA, a structural RNA, a ribosomal RNA, an hnRNA and an snRNA.

83. The method of paragraph 80, wherein said biological sample is fixed.

84. The method of paragraph 80, wherein the level of at least one second RNA transcript expression is quantified in said biological sample using a second signaling probe which produces a detectable signal upon hybridization to said second RNA transcript.

85. A method of identifying a compound that modulates transcription of at least one preselected RNA, comprising the steps of:
  a) adding a compound to cells exogenously or endogenously expressing said preselected RNA;
  b) exposing said cells to at least one signaling probe which produces a detectable signal upon hybridization with said at least one preselected RNA;
  c) quantitating the level of the signal in said cells;
  d) identifying cells that have an increase or decrease in signal compared to the signal of cells with no compound added; and
  e) identifying compounds that modulate transcription of said at least one preselected RNA.

86. The method of paragraph 85, wherein cells exogenously expressing said preselected RNA were isolated according to the method of paragraph 1 or 7.

87. The method of paragraph 85, wherein the DNA construct comprises a promoter or operator and encodes a repressor, enhancer, or a sequence that modulates transcription.

88. A method of identifying an RNA sequence that modulates transcription of at least one preselected RNA, comprising the steps of:
  a) introducing into cells at least a test RNA sequence that potentially modulates transcription of at least one preselected RNA that is exogenously or endogenously expressed;
  b) exposing said cells to at least one signaling probe which produces a detectable signal upon hybridization with said at least one preselected RNA;
  c) quantitating the level of the signal in said cells;
  d) identifying cells that have an increase or decrease in signal compared to the signal of cells with no test RNA sequence; and
  e) identifying a test RNA sequence that modulates transcription of said at least one preselected RNA.

89. The method of paragraph 88, wherein cells exogenously expressing said preselected RNA were isolated according to the method of paragraph 1 or 7.

90. The method of paragraph 88, wherein an expression library of RNA is used as the test RNA sequence.

91. A method for identifying genetic recombinational events in living cells comprising the steps of:
  a) exposing a cell to a signaling probe that produces a detectable signal upon hybridization with an RNA sequence selected from the group consisting of that transcribed from a recombined sequence and that transcribed from the non-recombined sequence;
  b) detecting said cell expressing said RNA sequence.

92. The method of any one of paragraphs 1, 3, 5, 7, 9, 13, 18, 21, 39, 53, 62, 67, 73, 80, 85, 88 and 91, wherein the signaling probe comprises two separate strands of nucleic acid or modified nucleic acid that form at least a mutually complementary region.

93. The method of paragraph 92, wherein the two separate strands form a continuous mutually complementary region from 5' to 3' end, and the two strands have the same number of nucleotides.

94. The method of paragraph 92, wherein after mutually complementary regions are formed between the two strands, the 5' end of one strand is offset from the other strand, or the 3' end of that strand is offset from the other strand, or both, wherein the offset is up to 10 nucleotides or modified nucleotides.

95. The method of paragraph 92, wherein the two strands form a mutually complementary region of 5 or 6 continuous basepairs at each end.

96. The method of paragraph 92, wherein the two strands are not identical in sequence.

97. The method of paragraph 92, wherein the strand has more than 30 nucleotides or modified nucleotides.

98. The method of paragraph 92, wherein the nucleic acid is DNA, RNA, or both.

99. The method of paragraph 92, wherein the modified nucleic acid comprises peptide nucleic acid, chemically modified DNA or RNA, or a combination thereof.

100. The method of paragraph 92, wherein the modified nucleic acid is chemically modified in one or more of a sugar group, phosphodiester linkage and base group.

101. The method of paragraph 100, wherein the phosphodiester linkage is substituted with a chemical group selected from the group consisting of —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$ NH—, —OCH$_2$C(O)$_2$O—, —OP(CH$_3$)(O)O—, —OP(CH$_2$C$_6$H$_5$)(O)O—, —P(S)(O)O— and —OC(O)$_2$NH—.

102. The method of paragraph 101, wherein the phosphodiester linkage is substituted with —OP(SH)(O)O—, —OP(S$^-$M$^+$)(O)O— or —P(S)(O)O—.

103. The method of paragraph 100, wherein the 2' position of the chemically modified RNA comprises the chemical group selected from the group consisting of a C$_1$-C$_4$ alkoxy, OCH$_2$—CH—CH$_2$, OCH$_2$—CH═CH—CH$_3$, OCH$_2$—CH═CH—(CH$_2$)$_n$CH3 (n=0, 1 ... 30), halogen, C$_1$-C$_6$ alkyl and OCH$_3$.

104. The method of paragraph 100, wherein the chemically modified RNA comprises a 2'-O-methyl substitution.

105. The method of paragraph 92, wherein the signaling probe comprises at least an interacting pair comprising two chemical groups, and one chemical group is at one terminus of one strand, and the other chemical group is at the adjacent terminus of the other strand.

106. The method of paragraph 92, wherein the signaling probe has two interacting pairs, wherein each end of the probe has one interacting pair at the adjacent terminus of both strands.

107. The method of paragraph 92, wherein the interacting pair is selected from the group consisting of a fluorophore and a quencher, a chemiluminescent label and a quencher or adduct, dye dimer, and FRET donor and acceptor, a proteolytic enzyme and an inhibitor of the proteolytic enzyme or another molecule capable of reversibly inactivating the enzyme.

108. The method of paragraph 92, wherein the interacting pair is a fluorophore and a quencher, and cells that fluoresce are isolated.

109. The method of paragraph 92, wherein the signaling probe comprises at least two fluorophores that are the same or different.

110. The method of paragraph 109, wherein the signaling probe comprises at least two fluorophores that are a FRET donor and acceptor pair, or a harvester and an emitter fluorophore.

111. The method of paragraph 108, wherein the step of isolating said cells that fluoresce is carried out using a fluorescence activated cell sorter, a fluorescence microscope or a fluorometer.

112. The method of any one of paragraphs 1, 3, 5, 7, 9, 13, 18, 21, 39, 53, 62, 67, 73, 80, 85, 88 and 91, wherein the signaling probe comprises a stem-loop structure.

113. The method of paragraph 112, wherein the stem region forms 4 to 6 continuous basepairs.

114. The method of paragraph 112, wherein the stem-loop structure comprises at least an interactive pair comprising two chemical groups, and one chemical group is at each terminus of the strand, wherein the stem region comprises two mutually complementary regions connected via a non-complementary region, the mutually complementary region adjacent to the interactive pair forms 5 to 6 basepairs, and the mutually complementary region adjacent to the loop region forms 4 to 5 basepairs.

115. The method of paragraph 114, wherein the non-complementary region is a single-stranded loop region or a mismatch region.

116. The method of paragraph 112, wherein the stem-loop structure comprises at least an interactive pair comprising two chemical groups, and one chemical group is at each terminus of the strand, wherein the stem region comprises three mutually complementary regions connected via two non-complementary regions, the first mutually complementary region adjacent to the interactive pair forms 4 to 5 basepairs, the second mutually complementary region forms 2 to 3 basepairs, and the third mutually complementary region adjacent to the loop region forms 2 to 3 basepairs.

117. The method of paragraph 116, wherein the non-complementary regions are one or more of a single-stranded loop region and a mismatch region.

118. The method of any one of paragraphs 1, 3, 5, 7, 9, 13, 18, 21, 39, 53, 62, 67, 73, 80, 85, 88 and 91, wherein the signaling probe comprises a dumbbell structure.

119. The method of paragraph 118, wherein the dumbbell structure comprises one stem region of 4 continuous basepairs, and one stem region of 3 continuous basepairs.

120. The method of paragraph 118, wherein the two stem regions are connected by a phosphodiester linkage or modified phosphodiester linkage via one arm of the stem regions.

121. The method of paragraph 118, wherein the two stem regions are connected by 1 or 2 nucleotides or modified nucleotides via one arm of the stem regions.

122. The method of paragraphs any one of paragraphs 1, 3, 5, 7, 9, 13, 18, 21, 39, 53, 62, 67, 73, 80, 85, 88 and 91, wherein the signaling probe comprises a three-arm junction structure.

123. The method of paragraph 122, wherein the three-arm junction structure comprises at least an interactive pair comprising two chemical groups, and one chemical group is at each terminus of the strand, wherein the stem region adjacent to the interactive pair forms 3 to 4 continuous basepairs, the stem region of the first stem-loop structure forms 4 to 5 continuous basepairs, and the stem region of the second stem-loop structure forms 2 to 3 continuous basepairs.

124. The method of paragraph 122, wherein the three regions are connected by a phosphodiester linkage or modified phosphodiester linkage via the arms of the stem regions.

125. The method of paragraph 122, wherein the three regions are connected by 1 or 2 nucleotides or modified nucleotides via the arms of the stem regions.

126. The method of any one of paragraphs 112, 118 and 122, wherein the stem-loop structure, dumbbell structure or three-arm junction structure has more than 30 nucleotides or modified nucleotides.

127. The method of any one of paragraphs 112, 118 and 122, wherein the structure is DNA, RNA, peptide nucleic acid, chemically modified DNA, RNA, or a combination thereof.

128. The method of any one of paragraphs 112, 118 and 122, wherein the structure is chemically modified in one or more of a sugar group, phosphodiester linkage and base.

129. The method of paragraph 128, wherein the phosphodiester linkage is substituted with the chemical group selected from the group consisting of —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$NH—, —OCH$_2$C(O)$_2$O—, —OP(CH$_3$)(O)O—, —OP(CH$_2$C$_6$H$_5$)(O)O—, —P(S)(O)O— and —OC(O)$_2$NH—.

130. The method of paragraph 129, wherein the phosphodiester linkage is substituted with —OP(SH)(O)O—, —OP(S$^-$M$^+$)(O)O— or —P(S)(O)O—.

131. The method of paragraph 128, wherein the 2' position of the chemically modified RNA comprises the chemical group selected from the group consisting of a C$_1$-C$_4$ alkoxy, OCH$_2$—CH═CH$_2$, OCH$_2$—CH═CH—CH$_3$, OCH$_2$—CH═CH—(CH$_2$)$_n$CH3 (n=0, 1 ... 30), halogen, or C$_1$-C$_6$ alkyl and OCH$_3$.

132. The method of paragraph 128, wherein the chemically modified RNA has a 2'-O-methyl substitution.

133. The method of any one of paragraphs 112, 118 and 122, wherein the interacting pair is selected from the group consisting of a fluorophore and a quencher, a chemiluminescent label and a quencher or adduct, dye dimer, and a FRET donor and acceptor, a proteolytic enzyme and an inhibitor of the proteolytic enzyme or another molecule capable of reversibly inactivating the enzyme.

134. The method of paragraph 133, wherein the interacting pair is a fluorophore and a quencher, and cells that fluoresce are isolated.

135. The method of paragraph 134, wherein the step of isolating said cells that fluoresce is carried out using a fluorescence activated cell sorter, fluorescence microscope or fluorometer.

136. The method of any one of paragraphs 112, 118 and 122, wherein the signaling probe comprises at least two fluorophores on one terminus of the strand, and a quencher on the other terminus of the strand, wherein the two fluorophores are a FRET donor and acceptor pair.

137. A probe comprising a nucleic acid or modified nucleic acid comprising sequence complementary to a target sequence and mutually complementary sequences, and at least a proteolytic enzyme and at least an inhibitor of the proteolytic enzyme, wherein said probe having, under assay conditions in the absence of said target sequence, a characteristic proteolytic activity whose level is a function of the degree of interaction of said proteolytic enzyme and inhibitor thereof; and wherein under conditions in the presence of an excess of said target sequence, hybridization of the target complement sequence to the target sequence increases the level of said characteristic proteolytic activity.

138. The probe of paragraph 137, wherein the proteolytic enzyme is a site-specific or target-specific protease.

139. The probe of paragraph 137, wherein said proteolytic enzyme inhibitor is a peptide or compound.

140. The probe of paragraph 137, wherein said proteolytic enzyme and said inhibitor of said proteolytic enzyme is selected from the group consisting of aminopeptidase and amastatin, trypsin-like cysteine proteases and antipain, aminopeptidase and bestatin, chymotrypsin like cysteine proteases and chymostatin, aminopeptidase and diprotin A or B, carboxypeptidase A and EDTA, elastase-like serine proteases and elastinal, and thermolysin or aminopeptidase M and 1,10-phenanthroline.

141. The probe of paragraph 137 that comprises two separate strands of nucleic acid or modified nucleic acid that form at least a mutually complementary region.

142. The probe of paragraph 141, wherein the proteolytic enzyme is at one terminus of one strand, and the proteolytic enzyme inhibitor is at the adjacent terminus of the other strand.

143. The probe of paragraph 141, wherein the two separate strands form a continuous mutually complementary region from 5' to 3' end, and the two strands have the same number of nucleotides.

144. The probe of paragraph 141, wherein after mutually complementary regions are formed between the two strands, the 5' end of one strand is offset from the other strand, or the 3' end of that strand is offset from the other strand, or both, wherein the offset is up to 10 nucleotides or modified nucleotides.

145. The probe of paragraph 141, wherein the two strands form a mutually complementary region of 5 or 6 continuous basepairs at each end.

146. The probe of paragraph 145, wherein the two strands are not identical in sequence.

147. The probe of paragraph 141, wherein the strand has more than 30 nucleotides or modified nucleotides.

148. The probe of paragraph 141, wherein the nucleic acid is DNA, RNA, or both.

149. The probe of paragraph 141, wherein the modified nucleic acid comprises peptide nucleic acid, chemically modified DNA or RNA, or a combination thereof.

150. The probe of paragraph 141, wherein the modified nucleic acid is chemically modified in one or more of a sugar group, phosphodiester linkage and base group.

151. The probe of paragraph 150, wherein the phosphodiester linkage is substituted with a chemical group selected from the group consisting of —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$ NH—, —OCH$_2$C(O)$_2$O—, —OP(CH$_3$)(O)O—, —OP(CH$_2$C$_6$H$_5$)(O)O—, —P(S)(O)O— and —OC(O)$_2$NH—.

152. The probe of paragraph 150, wherein the phosphodiester linkage is substituted with —OP(SH)(O)O—, —OP(S$^-$M$^+$)(O)O— or —P(S)(O)O—.

153. The probe of paragraph 150, wherein the 2' position of the chemically modified RNA comprises the chemical group selected from the group consisting of a $C_1$-$C_4$ alkoxy, OCH$_2$—CH=CH$_2$, OCH$_2$—CH=CH—CH$_3$, OCH$_2$—CH=CH—(CH$_2$)$_n$CH3 (n=0, 1 . . . 30), halogen, $C_1$-$C_6$ alkyl and OCH$_3$.

154. The probe of paragraph 150, wherein the chemically modified RNA comprises a 2'-O-methyl substitution.

155. The probe of paragraph 137 that comprises a stem-loop structure.

156. The probe of paragraph 155, wherein the stem region forms 5 to 6 continuous basepairs.

157. The probe of paragraph 155, wherein the stem-loop structure comprises at least a proteolytic enzyme and an inhibitor of said proteolytic enzyme at each terminus of the strand, wherein the stem region comprises two mutually complementary regions connected via a non-complementary region, the mutually complementary region adjacent to the terminus of the strand forms 5 to 6 basepairs, and the mutually complementary region adjacent to the loop region forms 4 to 5 basepairs.

158. The probe of paragraph 157, wherein the non-complementary region is a single-stranded loop region or a mismatch region.

159. The probe of paragraph 155, wherein the stem-loop structure comprises at least a proteolytic enzyme and an inhibitor of said proteolytic enzyme at each terminus of the strand, wherein the stem region comprises three mutually complementary regions connected via two non-complementary regions, the first mutually complementary region adjacent to the terminus of the strand forms 4 to 6 basepairs, the second mutually complementary region forms 2 to 3 basepairs, and the third mutually complementary region adjacent to the loop region forms 2 to 3 basepairs.

160. The probe of paragraph 159, wherein the non-complementary regions are one or more of a single-stranded loop region and a mismatch region.

161. The probe of paragraph 137 that comprises a dumbbell structure.

162. The probe of paragraph 161, wherein the dumbbell structure comprises one stem region of 4 continuous basepairs, and one stem region of 3 continuous basepairs.

163. The probe of paragraph 161, wherein the two stem regions are connected by a phosphodiester linkage or modified phosphodiester linkage via one arm of the stem regions.

164. The probe of paragraph 161, wherein the two stem regions are connected by 1 or 2 nucleotides or modified nucleotides via one arm of the stem regions.

165. The probe of paragraph 137 that comprises a three-arm junction structure.

166. The probe of paragraph 165, wherein the three-arm junction structure comprises at least a proteolytic enzyme and an inhibitor of said proteolytic enzyme at each terminus of the strand, wherein the stem region adjacent to the terminus of the strand forms 3 to 4 continuous basepairs, the stem region of the first stem-loop structure forms 4 to 5 continuous basepairs, and the stem region of the second stem-loop structure forms 2 to 3 continuous basepairs.

167. The probe of paragraph 165, wherein the three regions are connected by a phosphodiester linkage or modified phosphodiester linkage via the arms of the stem regions.

168. The probe of paragraph 165, wherein the three regions are connected by 1 or 2 nucleotides or modified nucleotides via the arms of the stem regions.

169. The probe of paragraph 155, 161 or 165, wherein the stem-loop structure, dumbbell structure or three-arm junction structure has more than 30 nucleotides or modified nucleotides.

170. The probe of paragraph 155, 161 or 165, wherein the structure is DNA, RNA, peptide nucleic acid, chemically modified DNA, RNA, or a combination thereof.

171. The probe of paragraph 155, 161 or 165, wherein the structure is chemically modified in one or more of a sugar group, phosphodiester linkage and base.

172. The probe of paragraph 171, wherein the phosphodiester linkage is substituted with the chemical group selected from the group consisting of —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$NH—, —OCH$_2$C(O)$_2$O—, —OP(CH$_3$)(O)O—, —OP(CH$_2$C$_6$H$_5$)(O)O, —P(S)(O)O— and —OC(O)$_2$NH—.

173. The probe of paragraph 171, wherein the phosphodiester linkage is substituted with —OP(SH)(O)O—, —OP(S$^-$-M$^+$)(O)O— or —P(S)(O)O—.

174. The probe of paragraph 171, wherein the 2' position of the chemically modified RNA comprises the chemical group selected from the group consisting of a C$_1$-C$_4$ alkoxy, OCH$_2$—CH═CH$_2$, OCH$_2$—CH═CH—CH$_3$, OCH$_2$—CH═CH—(CH$_2$)$_n$CH$_3$ (n=0, 1 . . . 30), halogen, or C$_1$-C$_6$ alkyl and OCH$_3$.

175. The probe of paragraph 171, wherein the chemically modified RNA has a 2'-O-methyl substitution.

176. A DNA construct comprising at least one DNA encoding at least one RNA of interest and a tag sequence, wherein the tag sequence forms a three-arm junction structure, and the stem region comprises 8-9 basepairs, the first stem-loop region comprises 4-6 basepairs and the second stem-loop region comprises 13-17 basepairs.

177. The DNA construct of paragraph 176, wherein the stem regions of the three arms further comprise non-complementary regions.

178. The DNA construct of paragraph 176, wherein the stem region and the first stem-loop region both further comprise one mismatch region, and the second stem-loop region further comprises 2-7 mismatch or bulge regions.

179. The DNA construct of paragraph 176, wherein the linkage between the stem regions has a total of 8-12 nucleotides.

180. A DNA construct comprising at least one DNA encoding at least one RNA of interest and a tag sequence, wherein the tag sequence is selected from the group consisting of the sequences shown in FIGS. 42A, B and C.

181. A DNA construct comprising at least one DNA encoding at least one RNA of interest and a tag sequence, wherein the tag sequence forms the more energetically favorable structures predicted by the sequences shown in FIG. 42A, B or C.

182. A vector comprising the DNA construct of any one of paragraphs 176 to 181.

183. A cell comprising the vector of paragraph 182 or the DNA construct of any one of paragraphs 176 to 181.

184. The cell of paragraph 183, that is selected from the group consisting of immortalized, primary, stem and germ cell.

185. The cell of paragraph 183 that is selected from the group consisting of HeLa cell, NIH3T3 cell, HEK293 cell and CHO cell.

186. A library of stable mammalian cell lines comprising at least 10,000 cell lines each comprising at least one stably integrated expressed sequence.

187. A library of stable mammalian cell lines comprising at least 500 cell lines each comprising at least two stably integrated sequences.

188. A library of stable mammalian cell lines comprising at least 50 cell lines each comprising at least three stably integrated sequences.

189. A library of stable mammalian cell lines comprising at least 20 cell lines each comprising at least four stably integrated sequences.

190. The library of any one of paragraphs 186-189, wherein the cell lines further comprise a drug resistance gene.

191. A library of stable mammalian cell lines comprising at least 50 cell lines each comprising at least one stably integrated sequence, wherein the cell lines lack a drug resistance gene.

192. A library of stable mammalian cell lines comprising at least 20 cell lines each comprising at least two stably integrated sequences, wherein the cell lines lack a drug resistance gene.

193. The library of any one of paragraphs 186-192, wherein each cell line comprises a variable library sequence.

194. The library of paragraph 193, wherein the variable sequence of said expression library is selected from the group consisting of genomic, genomic untranslated, genomic translated, gene, cDNA, EST, oligo, random, RNA, protein, protein domain, peptide, intronic, exonic, tag, or linker sequence, or combination thereof or recombination thereof, or one or more of the unmodified, mutagenized, randomized, shuffled or recombined sequences.

195. The library of any one of paragraphs 186-192, wherein the library was generated using at least a pool or mixture of genetic sequences having unknown sequence identity.

196. The library of paragraph 195, wherein said sequence having unknown identity has shared sequence homology, functional significance, or related origin.

197. The library of any one of paragraphs 186-192, wherein the library is a collection of individually synthesized constructs comprising specific sequences having known identities.

198. The library of paragraph 197, wherein said specific sequences have shared sequence homology, functional significance, or related origin.

199. The library of any one of paragraphs 186-192, wherein said expressed sequence is under the control of a constitutive promoter.

200. The library of any one of paragraphs 186-192, wherein said expressed sequence is under the control of a conditional promoter selected from the group consisting of an inducible, repressible, tissue-specific, temporal or heat-shock promoter.

201. The library of any one of paragraphs 186-192, wherein the library is used in a cell-based screening assay.

202. The library of paragraph 201, wherein the cell-based screening assay is carried out in parallel for all cell lines in said library.

203. The library of paragraph 201, wherein the cell-based screening assay is carried out for a portion of the cell lines in said library.

204. A nucleic acid or modified nucleic acid molecule comprising the sequence of any one of FP1 to FP18 according to FIGS. 8 to 24 and 41.

205. The nucleic acid or modified nucleic acid molecule of paragraph 204 further comprising an interactive pair.

206. The nucleic acid or modified nucleic acid molecule of paragraph 205, wherein the interactive pair is selected from the group consisting of a fluorophore and a quencher, a chemiluminescent label and a quencher or adduct, dye dimer, and a FRET donor and acceptor, a proteolytic enzyme and an inhibitor of the proteolytic enzyme or another molecule capable of reversibly inactivating the enzyme.

207. A nucleic acid or modified nucleic acid molecule that hybridizes to the sequences according to FIG. 42 D1, 2 or 3.

208. The nucleic acid or modified nucleic acid molecule of paragraph 207 further comprising an interactive pair.

209. The nucleic acid or modified nucleic acid molecule of paragraph 208, wherein the interactive pair is selected from the group consisting of a fluorophore and a quencher, a chemiluminescent label and a quencher or adduct, dye dimer, and a FRET donor and acceptor, a proteolytic enzyme and an inhibitor of the proteolytic enzyme or another molecule capable of reversibly inactivating the enzyme.

210. A nucleic acid or modified nucleic acid molecule comprising the sequence in FIG. 42 A, B or C.

211. A nucleic acid or modified nucleic acid molecule comprising the sequence in FIG. 42 D1 or D2.

This invention provides a method of isolating cells expressing an RNA comprising the steps of providing cells expressing the RNA, exposing the cells to a signaling probe that produces a detectable signal upon hybridization with the RNA, and isolating the cells that produce the signal. In one embodiment, the RNA is an endogenous RNA. In another embodiment, the endogenous RNA is expressed as a result of DNA that is introduced into the cell, e.g., the DNA comprises enhancer or promoter or other sequences that induce expression of an endogenous RNA. For example, the DNA may encode a protein, e.g., a transcription factor that induces expression of an RNA. In yet another embodiment, the RNA is encoded by a nucleic acid that is introduced into the cells. The DNA that is introduced into the cells may additionally encode a tag sequence where the signaling probe may optionally be targeted to the tag and/or RNA sequence. The tag sequence may be in-frame or out of frame with the open reading frame of the RNA. In one embodiment, the method includes detecting the expression of both an exogenous or heterologous RNA and an endogenous RNA. These methods may be practiced to detect multiple RNAs and/or tags at the same time. The RNAs may be the same or different RNAs. In those embodiments where the method is used to detect more than one RNA using more than one signaling probe, the signal produced by the different signaling probes may be the same or may be different from each other.

This invention also provides a method of isolating cells that comprise more than one copy of an exogenous or heterologous DNA. Such method include the steps of introducing a DNA encoding an RNA and a tag sequence and introducing a DNA encoding the same RNA and a different tag sequence; exposing the cells to signaling probes that produce a detectable signal to both tags; and isolating the cells that produce both signals.

In any of the methods of the invention where there is more than one exposing step, one or more of the exposing steps (i.e., the step where the cells are exposed to signaling probe) may be performed simultaneously or sequentially.

In any of the methods of the invention, the RNAs or proteins may be those in the same or related biological pathway, act upstream or downstream from each other, have modulating, activating, or repressing function with respect to each other, dependent on each other for function or activity, are components of the same complex, members of the same protein family, etc.

This invention provides a method of isolating cells comprising a DNA construct encoding a first RNA that is under the control of a conditional promoter, comprising the steps of introducing into cells a DNA construct encoding an RNA under the control of a constitutive promoter, wherein the DNA construct further encodes a second RNA under the control of a conditional promoter, under conditions where the second RNA is not expressed or expressed at a low level; exposing the cells to a signaling probe that produces a detectable signal upon hybridization with the first RNA; and isolating the cells that produce the signal. The DNA construct may further encode a test RNA, where, for example, the test RNA is variable, e.g., derived from an expression library. These cells may be used to obtain or identify RNA or compounds that are capable of activating the conditional promoter that drives expression of the second RNA.

Also provided by this invention are methods of isolating a plurality of cells wherein a subset of the cells express an RNA that is not expressed by another subset of the cells, comprising the steps of introducing into cells a plurality of DNA encoding a plurality of RNA, wherein at least a subset of the plurality of RNA are different from each other, exposing the cells to a plurality of different signaling probes, wherein the signaling probes produce a detectable signal upon hybridization to one or more RNAs encoded by the plurality of DNA, and isolating the cells that produce the signal. The subset of cells may be one cell or more than one cell. In one embodiment, the DNA does not encode RNA but results in the expression of endogenous RNA, e.g., the DNA comprises enhancer or promoter sequences, e.g., the DNA comprises sequences that induce expression of the endogenous RNA. For example, the DNA may encode a protein, e.g., a transcription factor that induces expression of an RNA. The DNA may additionally encode a tag sequence and the signaling probe may target the tag sequence and/or the RNA sequence. In one embodiment, the plurality of RNA form an expression library. In another embodiment, at least a subset of the DNA encode the same tag sequence.

This invention also provides a method of isolating two or more RNA libraries of cells comprising the steps of introducing into cells DNA encoding a first RNA expression library, wherein each DNA further encodes a first tag sequence, introducing into cells DNA encoding a second RNA expression library, wherein each DNA further encodes a second tag sequence, exposing the cells to a first signaling probe that produces a detectable signal upon hybridization to the first tag and a second signaling probe that produces a detectable signal upon hybridization to the second tag sequence, and isolating the cells that produce both signals. This method may be carried out with DNA encoding additional RNA expression libraries where one uses a third tag, etc.

Any of the methods of this invention may be used to identify a compound that modulates the expression of an RNA or plurality of RNAs by adding the compound to the cells and assaying for a change (increase or decrease) in signal produced by the signaling probe(s).

This invention provides methods of reducing expression of a protein comprising the steps of introducing into cells a DNA encoding an antisense RNA or an shRNA that reduces expression of the protein, exposing the cells to a first signaling probe that produces a detectable signal upon hybridization to the antisense RNA or shRNA, and isolating the cells that produce the signal. This method may further comprise the step of exposing the cells to a second signaling probe that produces a detectable signal upon hybridization to the RNA encoding the protein, wherein lack of signal from the second signaling probe indicates that the expression of the protein is reduced. One may also assay for reduced expression of the protein using other methods, e.g., using an antibody that specifically binds the protein, using a functional test, e.g. assaying for a known biological activity of the protein, etc. In one embodiment of this method, the step of exposing the cells to the first signaling probe is omitted. Any of the methods using siRNA may also be carried out using shRNA.

In any of the methods of this invention, the DNA that is introduced into the cells may be operably linked to a conditional promoter. In one embodiment, the RNA encoded by the DNA is lethal or damaging to the cell. The DNA may additionally comprise a selectable marker that can be used to select cells comprising the DNA.

This invention also provides a method of quantifying the expression level of an RNA in a biological sample comprising the steps of exposing the biological sample to a first signaling probe that produces a detectable signal upon hybridization with the RNA, quantifying the level of the signal in the biological sample, and correlating the level of signal with the expression level of the RNA.

This invention further provides a method of identifying a compound that modulates expression of an RNA comprising adding a test compound to cells expressing the RNA, exposing the cells to a signaling probe that produces a detectable signal upon hybridization with the RNA, and comparing the signal produced by cells exposed to the test compound to the signal produced by cells not exposed to the test compound, wherein an increase or decrease in signal produced by the former cells as compared to the signal produced by the latter cells indicates that the compound modulates expression of the RNA. In one embodiment, the RNA is encoded by DNA that is introduced into the cells. In one embodiment, the compound is an RNA or protein.

This invention provides a method of identifying a genetic recombinatorial event in living cells comprising the steps of exposing a cell to a signaling probe that produces a detectable signal upon hybridization with an RNA transcribed from a recombined sequence, wherein detection of a cell producing the signal indicates that the cell comprises the genetic recombinatorial event.

This invention also provides cells produced by any of the methods. These cells may be cultured and may be used to generate cell lines or a plurality of cell lines. The cells may be used for a variety of purposes, e.g., in a cell-based assay or where the cell is implanted in an animal, non-human animal, or mammal. The cell may be an embryonic stem cell, a primary, germ, or stem cell. The cell may also be an immortalized cell. The cells may be endothelial, epidermal, mesenchymal, neural, renal, hepatic, hematopoietic, or immune cells. The cells may be eukaryotic, prokaryotic, mammalian, yeast, plant, human, primate, bovine, porcine, feline, rodent, marsupial, murine or other cells.

The tag sequences may comprise multiple target sequences, wherein one signaling probe hybridizes to each target sequence. The tag sequences may be an RNA having secondary structure. The structure may be a three-arm junction structure. The DNA may comprise multiple tag sequences. The tag sequence may be transcribed as the same RNA as the RNA encoded by the DNA or the tag sequence may be transcribed as a separate RNA. Also provided is a DNA construct comprising a DNA sequence that encodes an RNA and a tag sequence. The tag sequence may be any one of those described herein. Cells and vectors comprising the DNA construct are also provided.

This invention also provides libraries of mammalian cell lines comprising at least 1,000, at least 800, at least 600, at least 500, at least 400, at least 200, at least 100 or at least 50 cell lines, wherein each cell line comprises a stably integrated expressed sequence. Also provided are libraries of mammalian cell lines comprising at least 500, at least 400, at least 300, at least 200, at least 200, at least 100, at least 50 cell lines, wherein each cell line comprises at least two stably integrated sequences. Also provided are libraries of mammalian cell lines comprising at least 100, at least 50, at least 25, at least 10 cell lines, wherein each cell line comprises at least three stably integrated sequences. Also provided are libraries of mammalian cell lines comprising at least 50, at least 25, at least 20, at least 10 cell lines, wherein each cell line comprises at least four stably integrated sequences. The stably integrated sequences in these cell lines may additionally lack a selection marker, e.g., a drug resistance gene. The stably integrated sequences may be of known or unknown sequence identity. These sequences may have shared sequence homology, functional significance, or related origin. These libraries may be used for a variety of purposes, e.g., in a cell-based screening assay.

This invention also provides a method of identifying a compound that enhances the detection of targets in cells using signaling probes comprising the steps of introducing a signaling probe into cells comprising a target sequence, wherein the signaling probe produces a detectable signal upon hybridization with the target sequence, exposing the cells to a test compound, and detecting the signal produced by the cells, wherein an increase in the signal produced by cells exposed to the test compound as compared to the signal produced by cells not exposed to the test compound indicates that the test compound is a compound that enhances the detection of targets in cells using signaling probes.

This invention also provides a method of identifying a compound that mediates or improves the introduction of signaling probes into cells comprising the steps of exposing cells to a signaling probe in the presence of a test compound, wherein the cells comprise a target sequence and wherein the signaling probe produces a signal upon hybridization with the target sequence; and detecting the signal produced by the cells, wherein an increase in signal produced by the cells exposed to the test compound as compared to cells not exposed to the test compound indicates that the test compound is a compound that mediates or improves the introduction of signaling probes into cells.

These and other aspects of the invention will be appreciated from the following detailed description.

BRIEF DESCRIPTION OF THE DRAWINGS

FIGS. 1 and 2 depict signaling or protease probes with two separate strands. The interacting chemical groups are shown as ovals. The different ovals present one embodiment of the invention, wherein the dark oval indicates a quencher moiety, and the white and grey ovals indicate different fluorophores.

FIGS. 3, 4 and 5 depict signaling or protease probes designed to have a stem-loop structure. The interacting chemical groups are shown as ovals. The different ovals present one embodiment of the invention, wherein the dark oval indicates a quencher moiety, and the white oval indicates a fluorophore.

FIGS. 12 through 13 show the sequences of fluorescent probes FP5 (SEQ ID NO: 27) to FP6 (SEQ ID NO: 28). The sequences comprises bases which are designed to be complementary to the target sequence and additional flanking bases. The flanking bases are underlined.

FIG. 15 shows the sequence and predicted native conformation of fluorescent probe FP8. The FP8 sequence comprises bases which are designed to be complementary to the target sequence and additional flanking bases. The flanking bases are underlined. Panel A shows the predicted structure of the sequence using DNA folding programs according to *Nucleic Acids Res.* 31: 3429-3431 (2003). Panel B shows predicted self dimerization of the FP1 sequence according to the oligoanalyzer 3.0 software available at the Integrated DNA Technologies SciTools website. In both Panels A and B, the flanking bases are shaded in grey, white and black ovals indicate fluorophore and quencher moieties, respectively.

FIGS. 16 through 20 show the sequences of the fluorescent probes FP9 to FP13. The sequences comprises bases which are designed to be complementary to the target sequence and additional flanking bases. The flanking bases are underlined.

FIGS. 22 through 24 show the sequence and predicted native conformation of fluorescent probes FP15 to 17, respectively. The sequences comprises bases which are designed to be complementary to the target sequence and additional flanking bases. The flanking bases are underlined. Panel A shows the predicted structure of the sequence using DNA folding programs according to *Nucleic Acids Res.* 31: 3429-3431 (2003). Panel B shows predicted self dimerization of the FP15 sequence according to the oligoanalyzer 3.0 software available at the Integrated DNA Technologies SciTools website In both Panels A and B, the flanking bases are shaded in grey, white and black ovals indicate fluorophore and quencher moieties, respectively.

FIG. 25A shows the profile for control NIH3T3 cells exposed to signaling probe FP1. The fluorophore Alexafluor633 was used in FP1. Control NIH3T3 cells were untransfected with plasmid and do not contain target sequence. FIG. 25B shows the profile for transfected NIH3T3 cells exposed to signaling probe FP1. The transfected NIH3T3 cells contained DNA encoding the RNA of interest and a tag1 sequence shown in FIG. 42A. FIG. 25C is an overlay of FIGS. 25A and 25B. FIG.

25C shows that FACS distinguishes cells transfected with plasmid encoding target sequences from untransfected control cells.

Figure 26:
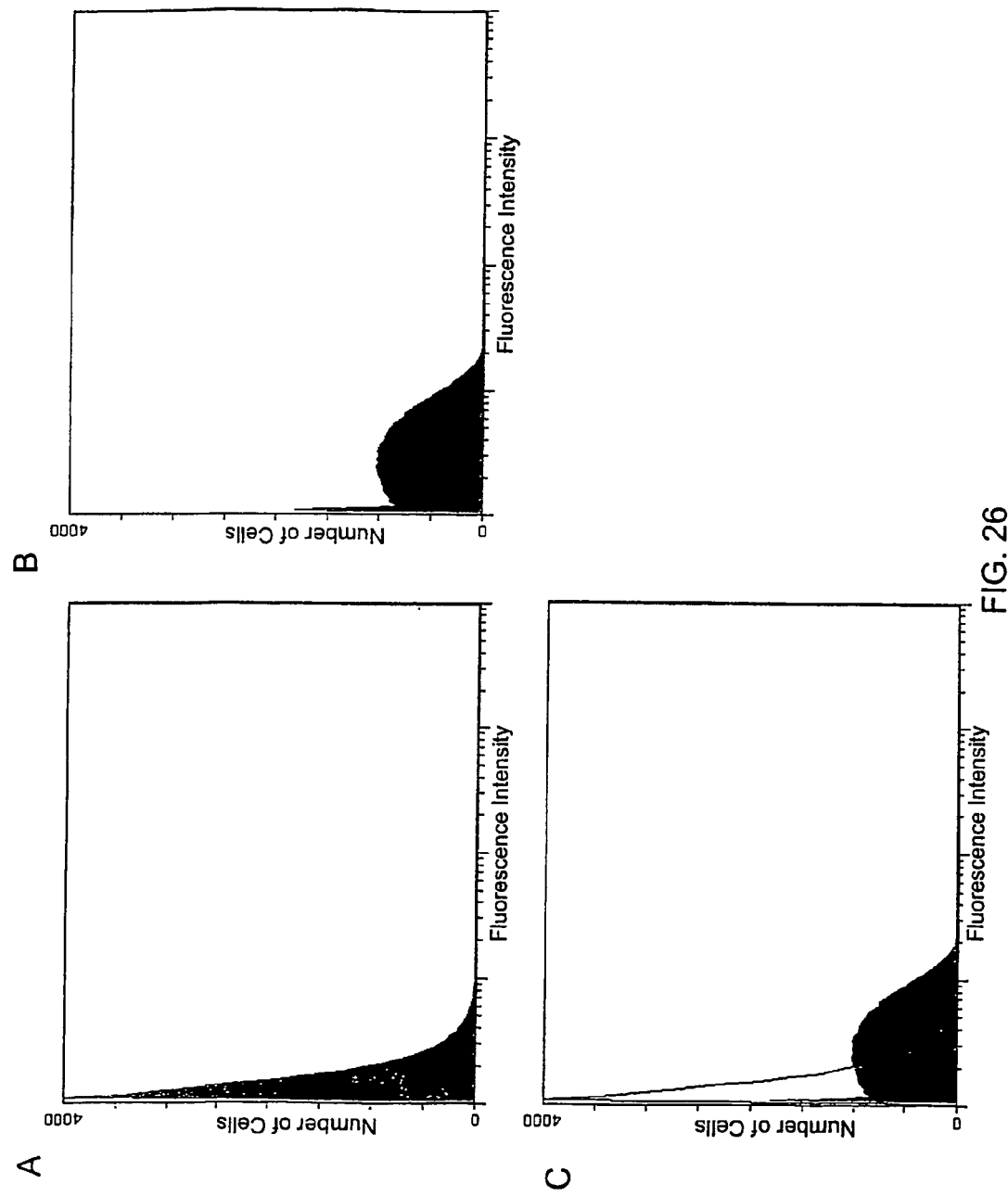

FIG. 26 shows the number of cells observed in reference to the fluorescence intensity during the FACS process. FIG. 26A shows the profile for control NIH3T3 cells exposed to signaling probe FP2. The fluorophore Alexafluor680 was used in FP2. Control NIH3T3 cells were untransfected with plasmid and do not contain target sequence. FIG. 26B shows the profile for transfected NIH3T3 cells exposed to signaling probe FP2. The transfected NIH3T3 cells contained DNA encoding the RNA of interest and a tag2 sequence shown in FIG. 42B. FIG. 26C is an overlay of FIGS. 26A and 26B. FIG. 26C shows that FACS distinguishes cells transfected with plasmid encoding target sequences from untransfected control cells.

Figure 27:
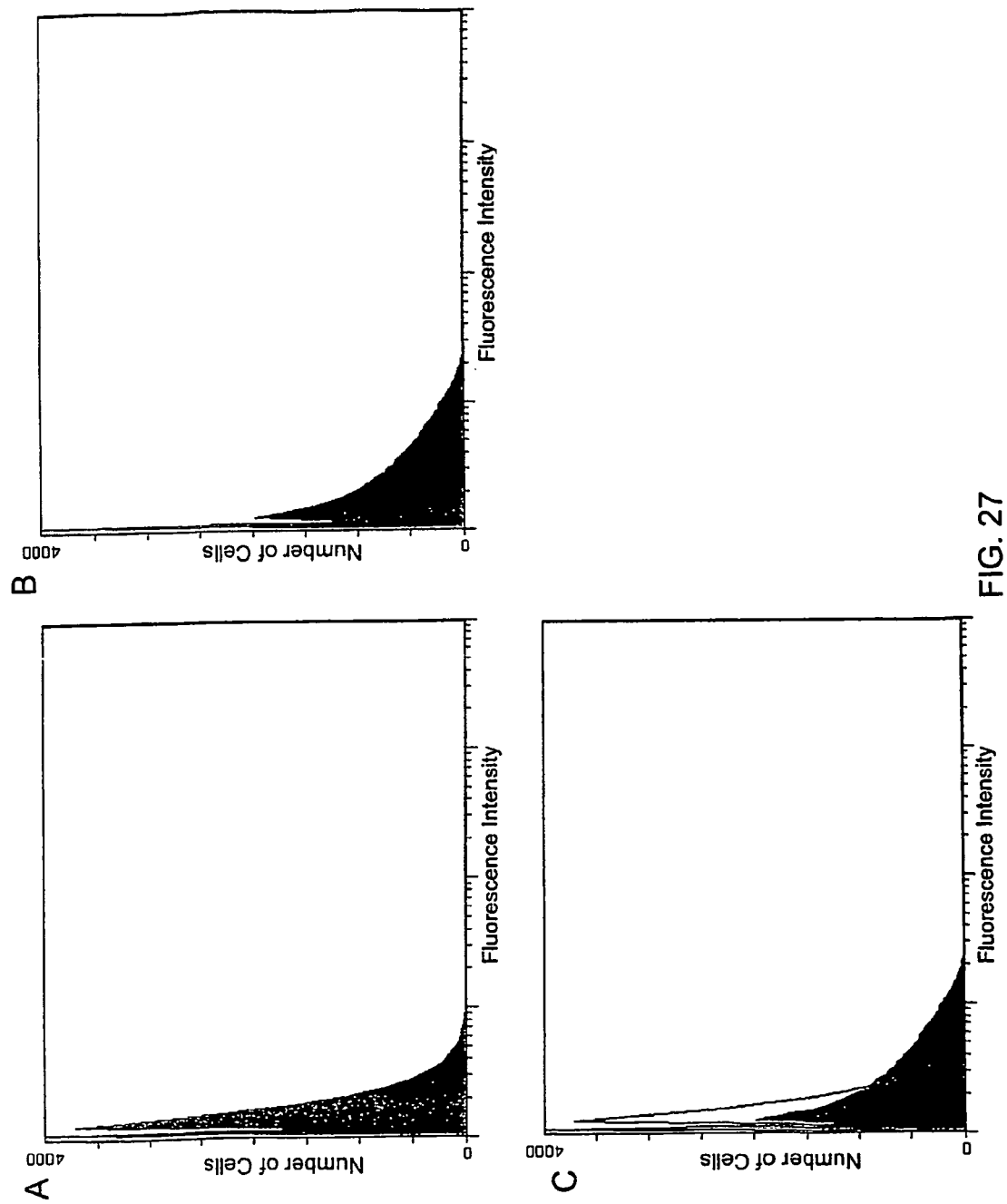

FIG. 27 shows the number of cells observed in reference to the fluorescence intensity during the FACS process. FIG. 27A shows the profile for control NIH3T3 cells exposed to signaling probe FP3. The fluorophore fluorescein was used in FP3. Control NIH3T3 cells were untransfected with plasmid and do not contain target sequence. FIG. 27B shows the profile for transfected NIH3T3 cells exposed to signaling probe FP3. The transfected NIH3T3 cells contained DNA encoding the RNA of interest and a tag3 sequence shown in FIG. 42C. FIG. 27C is an overlay of FIGS. 27A and 27B. FIG. 27C shows that FACS distinguishes cells transfected with plasmid encoding target sequences from untransfected control cells.

FIG. 28 shows the number of cells observed in reference to the fluorescence intensity during the FACS process. FIG. 28A shows the profile for control HeLa cells exposed to signaling probe FP1. The fluorophore fluorescein was used in FP1. Control HeLa cells were untransfected with plasmid and do not contain target sequence. FIG. 28B shows the profile for transfected HeLa cells exposed to signaling probe FP1. The transfected HeLa cells contained DNA encoding the reverse vav RNA. FIG. 28C is an overlay of FIGS. 28A and 28B. FIG. 28C shows that FACS distinguishes cells transfected with plasmid encoding target sequences from untransfected control cells.

FIG. 29 shows the number of cells observed in reference to the fluorescence intensity during the FACS process. FIG. 29A shows the profile for control HeLa cells exposed to signaling probe FP8. The fluorophore fluorescein was used in FP8. Control HeLa cells were untransfected with plasmid and do not contain target sequence. FIG. 29B shows the profile for transfected HeLa cells exposed to signaling probe FP8. The transfected HeLa cells contained DNA encoding the reverse vav RNA. FIG. 29C is an overlay of FIGS. 29A and 29B.

FIG. 29C shows that FACS distinguishes cells transfected with plasmid encoding target sequences from untransfected control cells.

Figure 30:
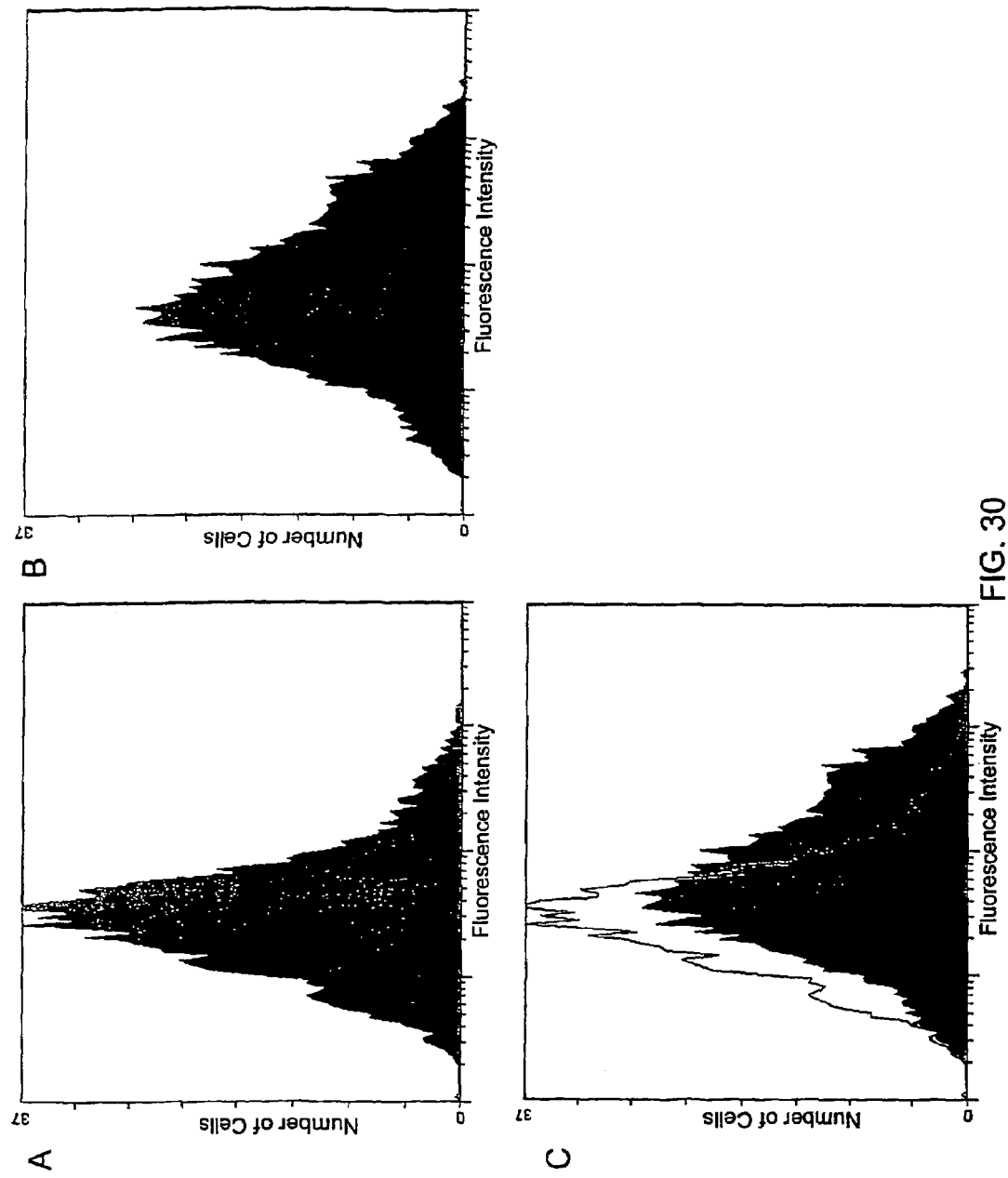

FIG. 30 shows the number of cells observed in reference to the fluorescence intensity during the FACS process. FIG. 30A shows the profile for control HeLa cells exposed to signaling probe FP5. The fluorophore fluorescein was used in FP5. Control HeLa cells were untransfected with plasmid and do not contain target sequence. FIG. 30B shows the profile for transfected HeLa cells exposed to signaling probe FP5. The transfected HeLa cells contained DNA encoding the reverse vav RNA. FIG. 30C is an overlay of FIGS. 30A and 30B. FIG. 30C shows that FACS distinguishes cells transfected with plasmid encoding target sequences from untransfected control cells.

FIG. 31 shows the number of cells observed in reference to the fluorescence intensity during the FACS process. FIG. 31A shows the profile for control HeLa cells exposed to signaling probe FP9. The fluorophore fluorescein was used in FP9. Control HeLa cells were untransfected with plasmid and do not contain target sequence. FIG. 31B shows the profile for transfected HeLa cells exposed to signaling probe FP9. The transfected HeLa cells contained DNA encoding the reverse vav RNA. FIG. 31C is an overlay of FIGS. 31A and 31B. FIG. 31C shows that FACS distinguishes cells transfected with plasmid encoding target sequences from untransfected control cells.

Figure 32:
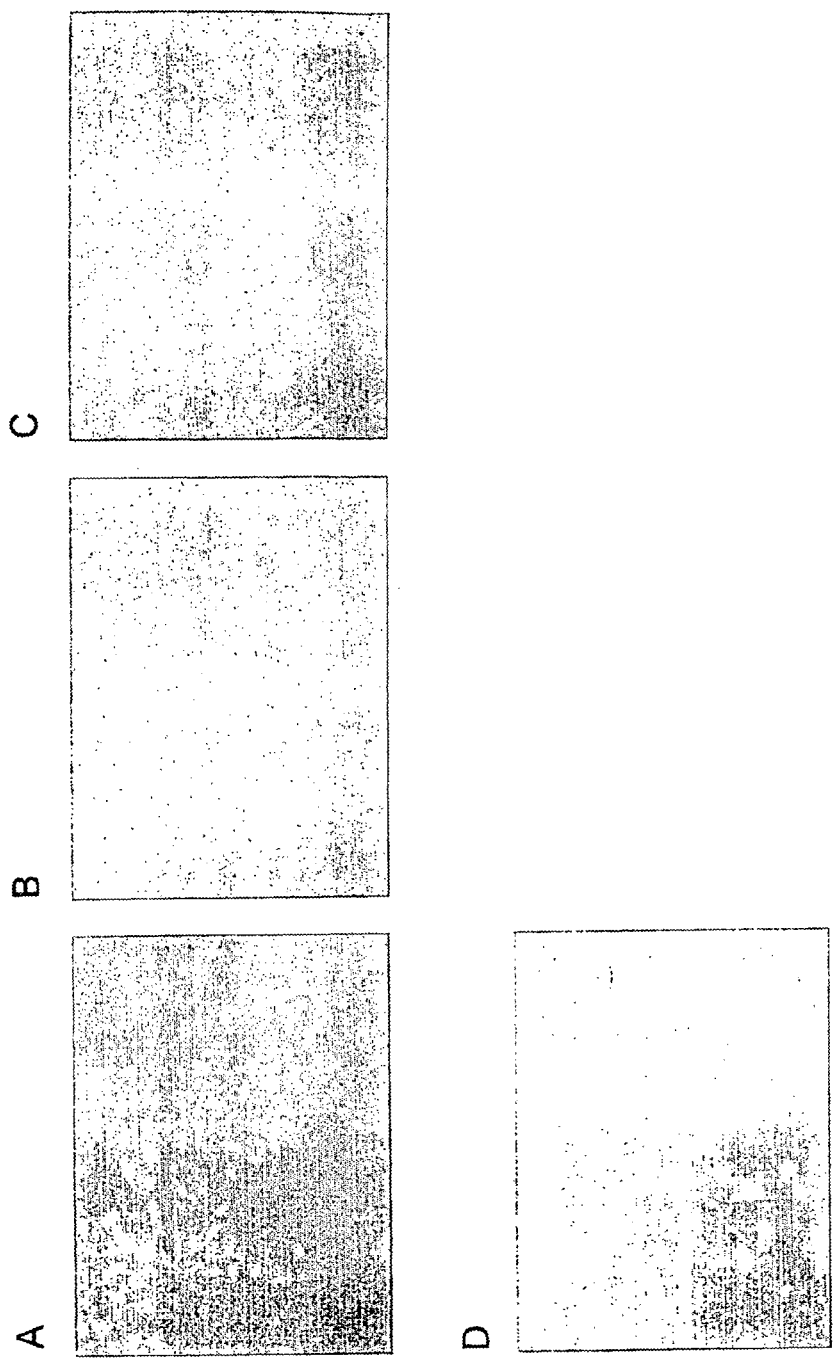

FIG. 32 shows fluorescence images of drug selected HeLa cells transfected with an expression plasmid encoding a portion of the sequence of vav cloned in reverse orientation (referred to r-vav) as well as a drug resistance gene. The cells were exposed to fluorescent probes (FP) designed to recognize the same target sequence within r-vav (5' GTTCTTAAG-GCACAGGAACTGGGA 3') (SEQ ID NO: 1). The images were obtained using a fluorescence microscope and filters designed to detect fluorescence from Fam. All FPs used here were labeled using FAM except FP1, which was labeled using fluorescein. Panel A, B, C, D each were exposed to FP10, FP 11, FP12 and FP13.

Figure 33:
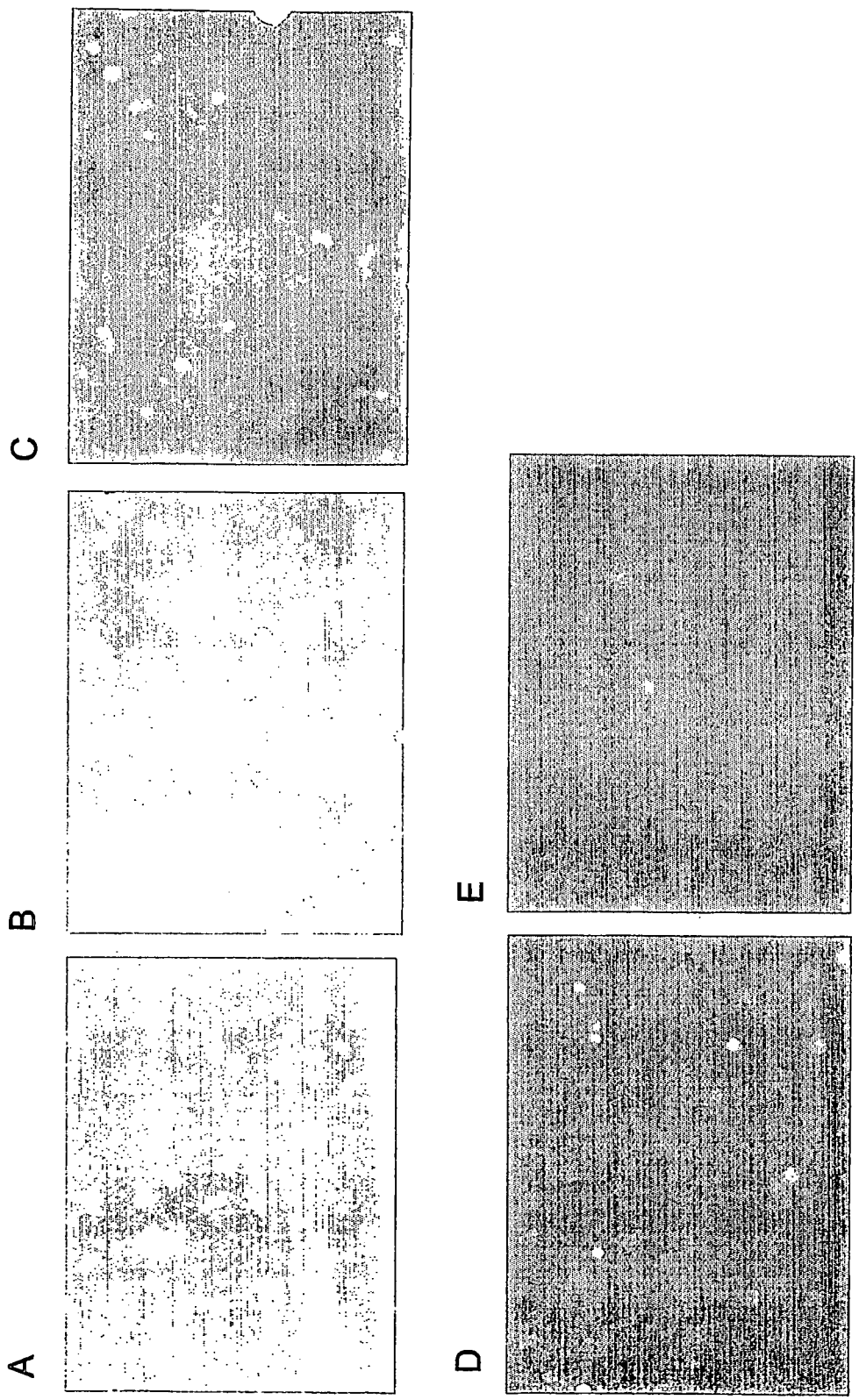

FIG. 33 shows the fluorescence image of cells transfected with constructs encoding RNA and tag sequences designed to be recognized by FP15 (Panels A, B, D) or transfected with control constructs encoding the same RNA but not the tag sequence (Panel C or E). The tag sequences used were termed 6-5, 6-7, or 6B10, which contained 1, 2 and 3 copies of the target sequence, respectively, which FP15 was designed to recognize. Cells transfected with constructs comprising tag sequences designed to be recognized by FP15 (Panels A, B and D) exhibited greater fluorescence than control cells (Panel C or E).

FIG. 34 shows the fluorescence image of cells transfected with constructs encoding RNA and tag sequence 6CA4 designed to be recognized by FP16 (Panel A) or transfected with control constructs encoding the same RNA but not the tag sequence (Panel B). Cells transfected with constructs comprising the tag sequence (Panel A) exhibited greater fluorescence than control cells (Panel B).

FIG. 35A (SEQ ID NO: 46) shows a portion of (underlined) the reverse complement of the vav DNA sequence (r-vav DNA) selected for forming the tag sequence. This sequence was cloned into an expression plasmid designed to express r-vav mRNA. The sequence indicated in bold is the target sequence for certain fluorescent probes. FIG. 35B (SEQ ID NO: 47) shows the sequences underlined in FIG. 35A after they have been combined to form a tag sequence (tag 1 sequence).

FIG. 36A (SEQ ID NOS: 69-71) shows the predicted structure of part of the r-vav RNA using RNA folding programs in *Nucleic Acids Res.* 31: 3429-3431 (2003). FIG. 36B (SEQ ID NO: 68) is the predicted structure of the tag 1 sequence shown in FIG. 35B. The shading indicates the target sequence designed to be recognized by some of the fluorescent probes.

FIGS. 37A (SEQ ID NO: 65), B (SEQ ID NO: 66) and C (SEQ ID NO: 67) show the predicted structures for tag 1, 2 and 3 sequence as described in FIG. 42. These structures resemble each other but present a different sequence for recognition by fluorescent probes. The prediction was generated using RNA folding programs in *Nucleic Acids Res.* 31: 3429-3431 (2003).

Figure 38:
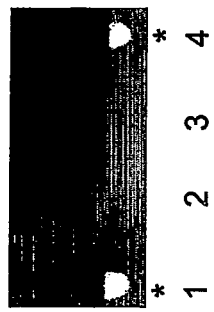

FIG. 38 shows fluorescence signal emitted from FPs in solution in the presence of target or control oligo sequence. Samples were illuminated by UV and photographed. All FPs used here incorporated Fluorescein. Tubes each contained 16 ul total consisting of 5 ul of a 20 uM FP stock, 1.5 ul 25 mM MgCl2, 8 ul 20 uM oligo, and 1.5 ul of water, having a final magnesium concentration of approximately 2.34 mM. FP1 and FP18 were used here and were synthesized incorporating sulfur linkages between the bases of the sequence designed to recognize target oligos TO-FP1 and TO-FP18, respectively. FP1 is directed against the sequence of target oligo 1 (TO-FP15'GTTCTTAAGGCACAGGAACTGGGA3') (SEQ ID NO: 1), and FP 18 is directed against the sequence of target oligo FP18 (TO-FP18 5'TCCCAGTTCCTGTGCCTTAA-GAAC3') (SEQ ID NO: 2). The sequences of TO-FP1 and TO-FP 18 were reverse complements of each other. TO-FP 18 has sequence not targeted by FP 1 and served as a control oligo for FP 1. TO-FP 1 has sequence not targeted by FP 18 and served as a control oligo for FP18.

In all Panels, the compositions of the tubes are as indicated below:

| tube | FP | oligo |
|---|---|---|
| 1 | FP18 | TO-FP18 |
| 2 | FP18 | TO-FP1 |
| 3 | FP1 | TO-FP18 |
| 4 | FP1 | TO-FP1 |

This figure shows that each of the FPs tested were specifically reporting the presence of target sequences by emitting a greater signal in tubes containing oligos having targeted sequence as compared to control tubes containing oligos having non-targeted sequence. Tubes containing FPs in the presence of oligos comprising target sequence are indicated by asterisk.

FIG. 39 shows fluorescence signal emitted from FPs in solution in the presence of target or control oligo sequence. Samples were illuminated by UV and photographed. All FPs used here incorporated FAM. Panels A, B, C each show four tubes to which the same FP was added. Each tube contains a total of 10 ul containing 2 ul of a 20 uM FP stock and 1 ul of a 100 um oligo stock in PBS supplemented to 4 mM MgCl$_2$. In each Panel, tube 1 contained no oligo stock and instead contained 1 ul water, tube 2 contained oligo TO-M1, tube 3 contained oligo TO-M2 and tube 4 contained oligo TO-M3.

The FPs tested in each Panel are listed below, alongside the oligo which includes sequence that is designed to be recognized by the FP:

| Panel | FP | oligo comprising target sequence |
|---|---|---|
| A | FP4 | TO-M3 (tube 4) |
| B | FP6 | TO-M2 (tube 3) |
| C | FP7 | TO-M3 (tube 4) |

This figure shows that each of the FPs tested were specifically reporting the presence of target sequences by emitting a greater signal in tubes containing oligo having targeted sequence as compared to control tubes containing no oligo or oligo having non-targeted sequence. Tubes containing FPs in the presence of oligos comprising target sequence are indicated by asterisk.

Sequences from 5' to 3' direction for TO-M1, TO-M2 and TO-M3 are listed below:

```
TO-M1:
                                     (SEQ ID NO: 3)
TTTCTCTGTGATCCGGTACAGTCCTTCTGCGCAGGTGGACAGGAA

GGTTCTAATGTTCTTAAGGCACAGGAACTGGGACATCTGGGCCCG
```

```
GAAAGCCTTTTTCTCTGTGATCCGGTACAGTCCTTCTGCGCAGGT

GGACAGGAAGGTTCTAATGTTCTT
```

```
TO-M2:
                                     (SEQ ID NO: 4)
TTTAACTGATGGATGGAACAGTCCTTCTGCGCAGGTGGACAGCTT

GGTTCTAATGAAGTTAACCCTGTCGTTCTGCGACATCTGGGCCCG

GAAAGCGTTTAACTGATGGATGGAACAGTCCTTCTGCGCAGGTGG

ACAGCTTGGTTCTAATGAAGTT
```

```
TO-M3:
                                     (SEQ ID NO: 5)
GTAAAGTCAGACATCCGGTACAGTCCTTCTGCGCAGGTGGACAGG

AAGGTTCTAATGTTCTATAGGGTCTGCTTGTCGCTCATCTGGGCC

CGGAGATGCGTAAAGTCAGACATCCGGTACAGTCCTTCTGCGCAG

GTGGACAGGAAGGTTCTAATGTTCTAT
```

FIG. 40 shows fluorescence signal emitted from FPs in solution in the presence of target or control oligo sequence. Samples were illuminated by UV and photographed. All FPs used here incorporated FAM. FPs 1, 2 and 3 were tested in Panels A, B and C, respectively, and are each designed to recognize related target sequences incorporated into tags 1, 2 and 3, respectively, as described in FIG. 42. Tubes containing FPs in the presence of oligos comprising target sequence are indicated by asterisk.

The protocol for panel A, B, C was according to the protocol for FIG. 39, and samples are described below:

| Panel | FP | oligo comprising target sequence |
|---|---|---|
| A | FP1 | TO-M1 (tube 2) |
| B | FP2 | TO-M2 (tube 3) |
| C | FP3 | TO-M3 (tube 4) |

FIG. 41 shows the sequence and predicted native conformation of fluorescent probe FP18. The sequence comprises bases which are designed to be complementary to the target sequence and additional flanking bases. The flanking bases are underlined. Panel A shows the predicted structure of the sequence using DNA folding programs according to Nucleic Acids Res. 31: 3429-3431 (2003). Panel B shows predicted self dimerization of the FP2 sequence according to the oligo-analyzer 3.0 software available at the Integrated DNA Technologies SciTools website. In both Panels A and B, the flanking bases are shaded in grey, white and black ovals indicate fluorophore and quencher moieties, respectively.

FIGS. 42A, B and C show the three tag sequences recognized by fluorescent probes. In FIGS. 42A, B and C, the target sequences are indicated in bold and they are also shown in FIG. 42D. The first sequence (tag1, 42A) is the same as the sequence indicated in FIG. 35B. The next two sequences (tag2, 42B and tag3, 42C) are altered versions of tag1. The differences in sequence of target2 and target3 as compared to target1 is underlined in Panel D. Additional sequence changes were made in the remaining tag sequences to compensate for the changes made in the portions shown.

FIG. 43 shows the design of tag2 sequence from tag1 sequence. A-F indicate the sequential base changes made during the design.

FIG. 44 shows the design of tag3 sequence from tag1 sequence. A-F indicate the sequential base changes made during the design.

Figure 45:
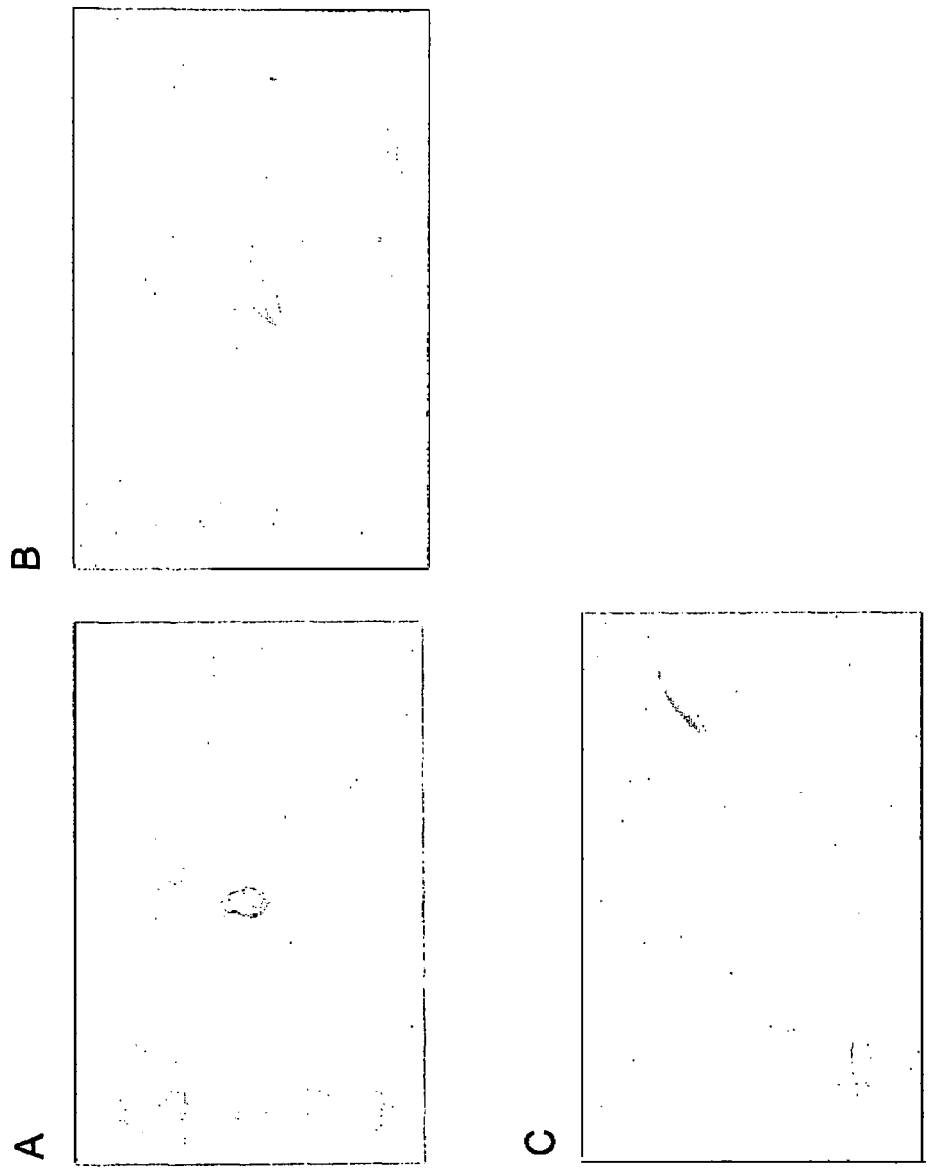

FIG. 45 shows that cells isolated according to the methods of this invention are viable. Panel A shows a cell isolated using FACS after the cell was transfected with three DNA constructs each encoding an RNA of interest tagged with tag1, 2 and 3, respectively. The cells were drug selected and exposed to FP1, 2 and 3 and isolated. The fluorescence intensity of the cells for each of the three probes was above background intensities compared to control cells not transfected with any of the DNA constructs. The cells were individually plated in a well of a 96-well plate directly by the FACS and one was imaged right after its isolation. Panel B shows the same cell one hour later, after it attached to the surface of the well. Panel C shows the same cell the following day, after it had undergone cell division.

The three panels each show that cells isolated according to the methods remain viable despite the previously unknown effects of the reagents used to expose the cells to the probes. These effects include compromising the plasma membrane of the cell and possibly further subjecting the cells to high pressures during FACS. Panel A shows that the cell membrane is not found to be compromised, and Panels B and C further demonstrate that the cell is viable since it can attach to the surface of the culture dish and divide, both of which are properties of viable cells.

FIG. 46 shows the results of FACS analysis of 293T cells transfected with mcon1 as compared to control cells.

FIG. 47 shows the results of FACS analysis of 293T cells transfected with mcon2 as compared to control cells.

FIG. 48 shows the results of FACS analysis of 293T cells transfected with mcon3 as compared to control cells.

FIG. 49 shows the results of FACS analysis of 293T cells transfected with mcon4 as compared to control cells.

FIG. 50 shows the results of FACS analysis of 293T cells transfected with mcon5 as compared to control cells.

FIG. 51 shows the results of FACS analysis of 293T cells transfected with mcon6 as compared to control cells.

FIG. 52 shows the results of FACS analysis of 293T cells transfected with mcon7 as compared to control cells.

FIG. 53 shows the results of FACS analysis of 293T cells transfected with mcon8 as compared to control cells.

FIG. 54 shows the results of FACS analysis of 293T cells transfected with mcon9 as compared to control cells.

FIG. 55 shows the results of FACS analysis of 293T cells transfected with mcon10 as compared to control cells.

FIG. 56 shows the results of FACS analysis of 293T cells transfected with mcon11 as compared to control cells.

FIG. 57 shows the results of FACS analysis of 293T cells transfected with mcon12 as compared to control cells.

FIG. 58 shows the results of FACS-analysis of 293T cells transfected with mcon13 as compared to control cells.

FIG. 59 shows the results of FACS analysis of 293T cells transfected with mcon14 as compared to control cells.

FIG. 60 shows the results of FACS analysis of 293T cells transfected with mcon15 as compared to control cells.

DETAILED DESCRIPTION OF THE INVENTION

Unless otherwise defined, all technical and scientific terms used herein have the same meaning as commonly understood by one of ordinary skill in the art to which this invention belongs. All publications and other references mentioned herein are incorporated by reference in their entirety. In case of conflict, the present specification, including definitions, will control.

The term "adjacent" as used in the context of probes refers to a condition of proximity to allow an interacting pair to functionally interact with each other. For example, the condition of proximity allows a fluorophore to be quenched or partially quenched by a quencher moiety or a protease inhibitor to inhibit or partially inhibit a protease. The distance required for currently known fluorophore and quencher to interact is about 20-100 Å.

The term "basepair" refers to Watson-Crick basepairs.

The term "bulge region" refers to a single-stranded region of one nucleotide or modified nucleotide that is not base-paired. The bulged nucleotide can be between mutually complementary regions (for example, FIG. 4A).

Figure 7:
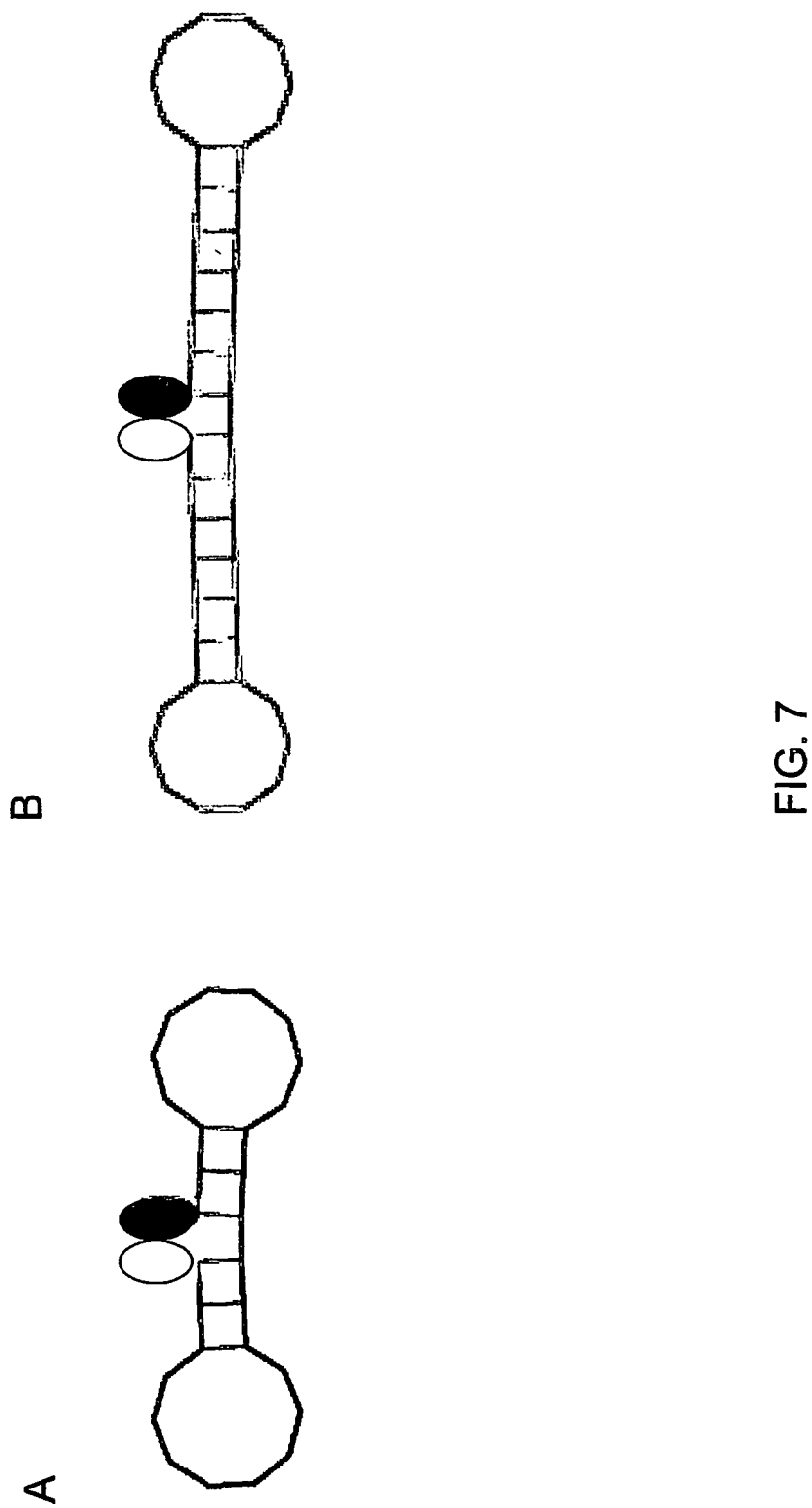
FIG. 7 depicts signaling or protease probes with a dumbbell structure. The interacting chemical groups are shown as ovals. The different ovals present one embodiment of the invention, wherein the dark oval indicates a quencher moiety, and the white oval indicates a fluorophore.

The term "dumbbell structure" refers to a strand of nucleic acid or modified nucleic acid having the conformation of two stem-loop structures linked via the end of an arm from each of the stem regions (for example, FIG. 7). The linkage may be a non-complementary region, or a phosphodiester linkage with or without modification.

The term "interacting pair" refers to two chemical groups that functionally interact when adjacent to each other, and when not adjacent to each other, produce a detectable signal compared to the absence of signal or background signal produced by the interacting chemical groups, or produce a different signal than the signal produced by the interacting chemical groups. An interacting pair includes but is not limited to a fluorophore and a quencher, a chemiluminescent label and a quencher or adduct, a dye dimer and FRET donor and acceptor, or a combination thereof. A signaling probe can comprise more than one interacting pair. For example, a wavelength-shifting signaling probe has a first fluorophore and a second fluorophore that both interact with the quencher, and the two fluorophores are FRET donor and acceptor pairs.

Figure 23:
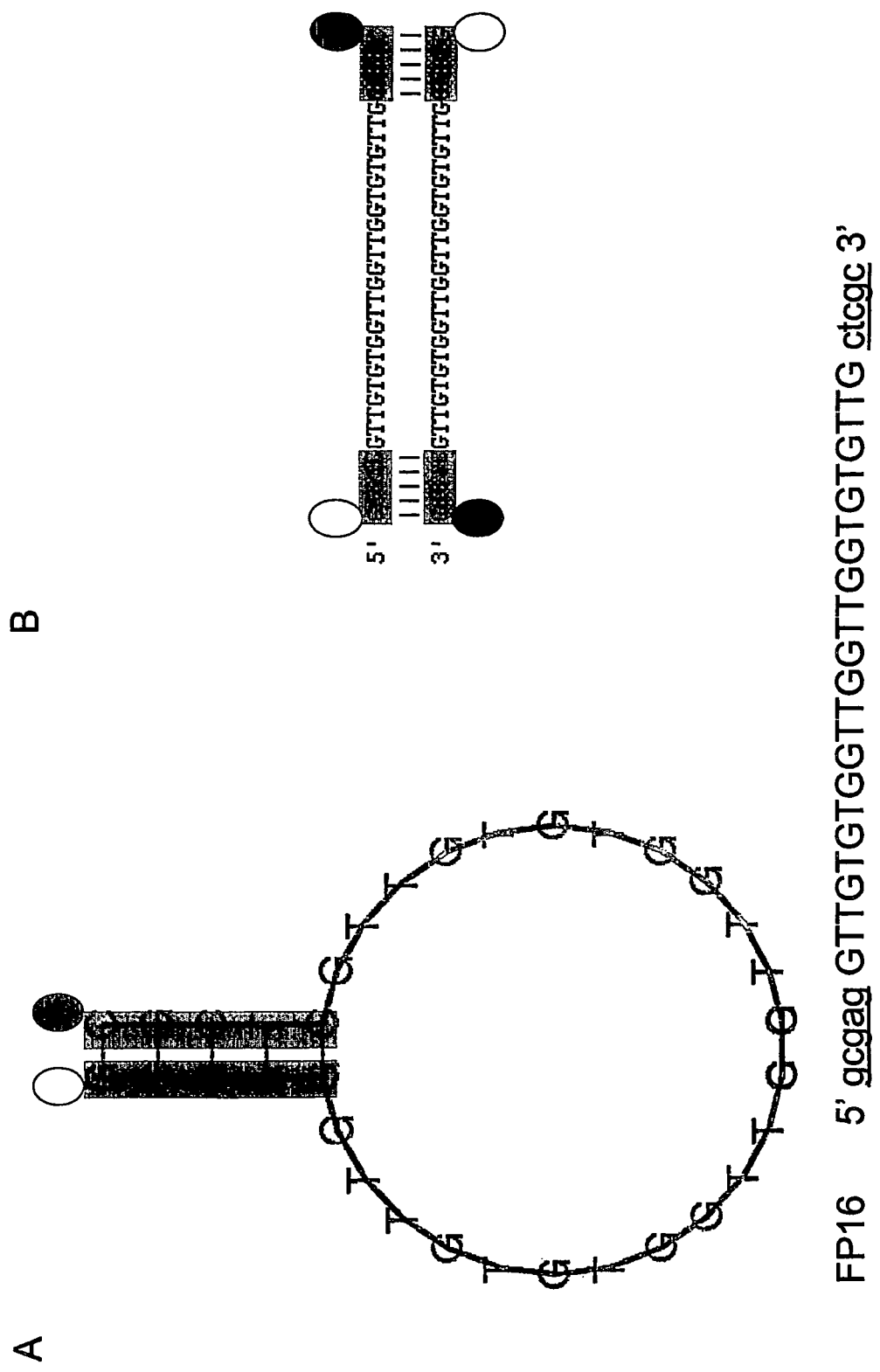
Figure 25:
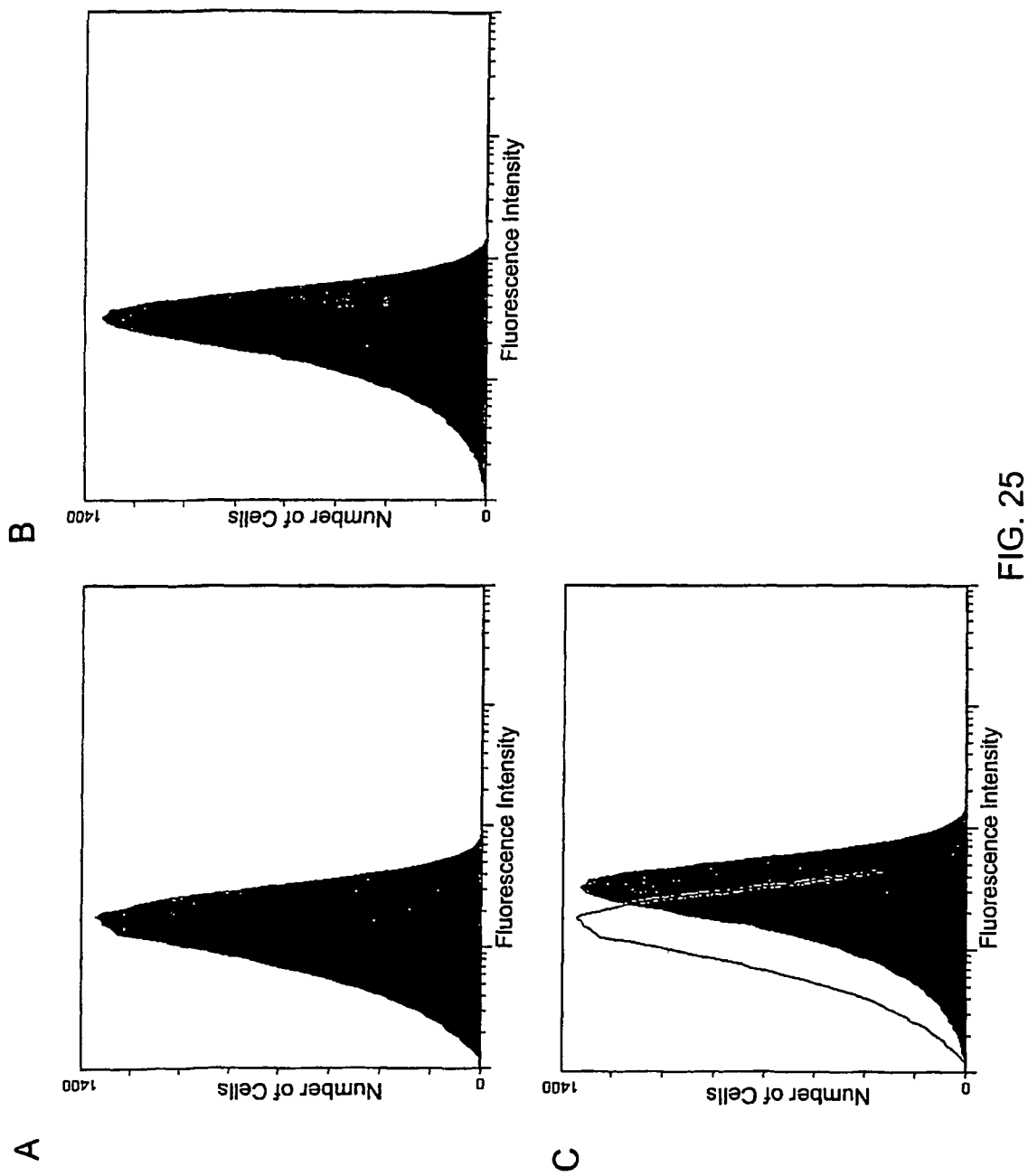
FIG. 25 shows the number of cells observed in reference to the fluorescence intensity during the FACS process.

The term "loop region" refers to a single-stranded region of more than one nucleotide or modified nucleotide that is not base-paired (for example, FIG. 4B and FIG. 23A). The loop can also be between a mutually complementary region (FIG. 8A)

The term "signaling probe" refers to a probe comprising a sequence complementary to a target nucleic acid sequence and at least a mutually complementary region, and further comprising at least an interacting pair. When the signaling probe is not bound to its target sequence, the moieties of the interacting pair are adjacent to each other such that no or little or different signal is produced. When the signaling probe is bound to the target sequence, the moieties of the interacting pair are no longer adjacent to each other and a detectable signal or a different signal than the signal produced by the probe in its unbound state is produced. In one embodiment, the signaling probe is a fluorogenic or fluorescent probe that comprises a fluorophore and a quencher moiety, and a change in fluorescence is produced upon hybridization to the target sequence. The moieties of the interacting pair may be attached to the termini of the signaling probe or may be attached within the nucleic acid sequence. Examples of moieties that may be incorporated internally into the sequence of the signaling probe include the quenchers: dabcyl dT, BHQ2 dT, and BHQ1 dT, and the fluorophores: fluorescein dT, Alexa dT, and Tamra dT.

The term "protease probe" refers to a probe comprising a sequence complementary to a target sequence and at least a mutually complementary region, and further comprising at least a proteolytic enzyme and at least an inhibitor of the proteolytic enzyme or another molecule capable of reversibly inactivating the enzyme. When the probe is not hybridized to a target sequence, the proximity of the proteolytic enzyme and the inhibitor of the proteolytic enzyme allows them to interact, inhibiting proteolytic activity. Upon hybridization of the probe to the target sequence, the proteolytic enzyme and its inhibitor are separated, activating the proteolytic enzyme.

The proteolytic enzyme and inhibitor can be covalently or non-covalently attached to the probe.

The term "mismatch region" refers to a double-stranded region in a nucleic acid molecule or modified nucleic acid molecule, wherein the bases or modified bases do not form Watson-Crick base-pairing (for example, FIGS. 4B and C). The mismatch region is between two base-paired regions. The double-stranded region can be non-hydrogen bonded, or hydrogen bonded to form Hoogsteen basepairs, etc, or both.

The term "mutually complementary region" refers to a region in a nucleic acid molecule or modified nucleic acid molecule that is Watson-Crick base paired.

The term "non-complementary region" refers to a region in a nucleic acid molecule or modified nucleic acid molecule that is not Watson-Crick base paired. For example, the non-complementary region can be designed to have bulged nucleotides, a single-stranded loop, overhang nucleotides at the 5' or 3' ends, or mismatch regions.

The term "stem region" refers to a region in a nucleic acid molecule or modified nucleic acid molecule that has at least two Watson-Crick basepairs. For example, the stem region can be designed to have more than one mutually complementary region linked by non-complementary regions, or form a continuous mutually complementary region.

Figure 4:
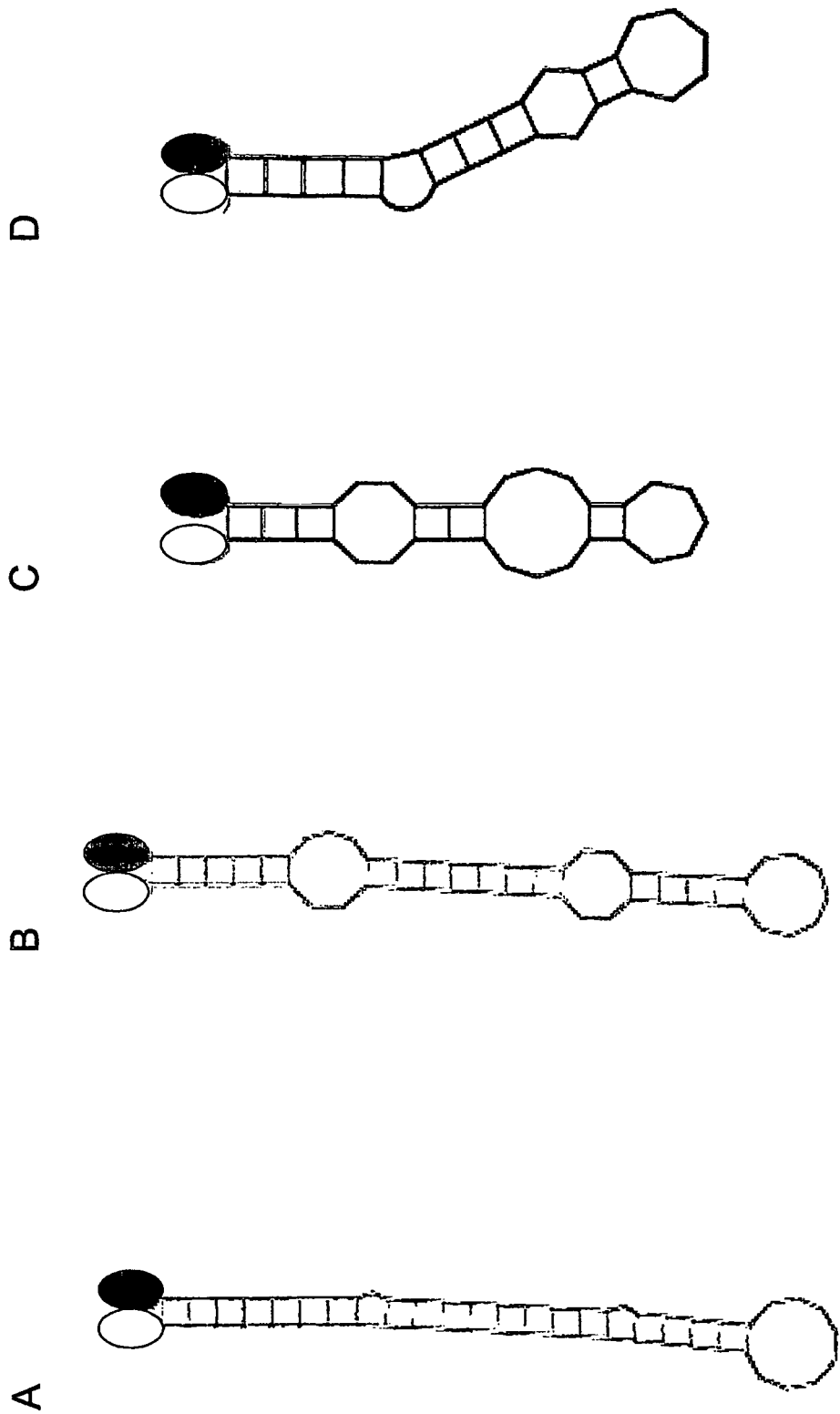

The term "stem-loop structure" refers to a nucleic acid molecule or modified nucleic acid molecule with a single-stranded loop sequence flanked by a pair of 5' and 3' oligonucleotide or modified oligonucleotide arms (for example, FIG. 4). The 5' and 3' arms form the stem region.

Figure 6:
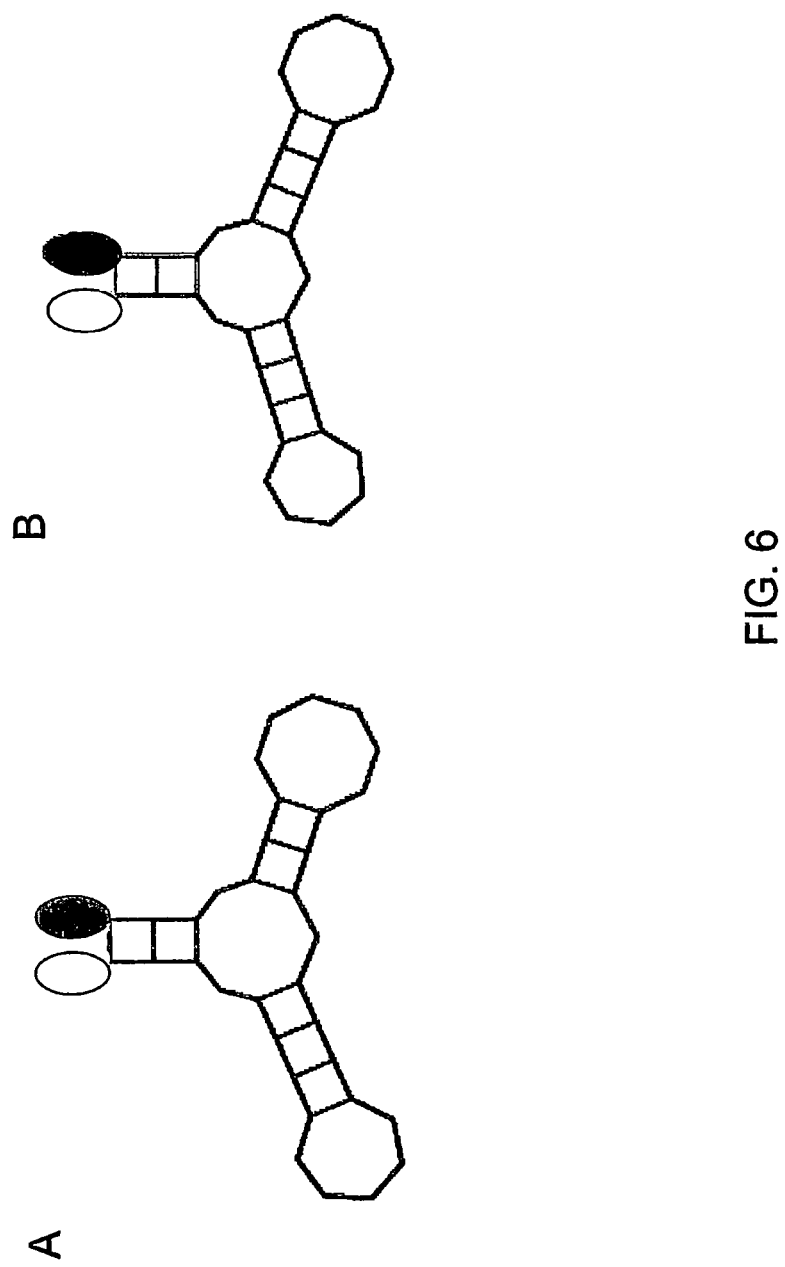
FIG. 6 depicts signaling or protease probes with a three-arm junction structure. The interacting chemical groups are shown as ovals. The different ovals present one embodiment of the invention, wherein the dark oval indicates a quencher moiety, and the white oval indicates a fluorophore.

The term "three-arm junction structure" refers to a strand of nucleic acid or modified nucleic acid that has a conformation of a stem region, a first stem-loop region, and a second stem-loop region linked together via arms of the stem regions (for example, FIG. 6). The first stem-loop region is 5' to the second stem-loop region. The three regions can be connected via a non-complementary region, a phosphodiester linkage, or a modified phosphodiester linkage, or a combination thereof.

Signaling Probe
Interacting Pair

The signaling probe may have more than one interacting pair, or have different interacting pairs. In one embodiment, the signaling probe is a fluorogenic probe. In one embodiment, the fluorogenic probe does not emit or emits a background level of fluorescence in its unhybridized state, but fluoresces upon or fluoresces above the background level upon binding to its target. Multiple fluorophores can be used to increase signal or provide fluorescence at different color ranges. Multiple quenchers can be used to decrease or eliminate signal in the absence of target sequence. Examples of quenchers include but are not limited to DABCYL, EDAC, Cesium, p-xylene-bis-pyridinium bromide, Thallium and Gold nanoparticles. Examples of fluorophores include but are not limited to sulforhodamine 101, acridine, 5-(2'-aminoethyl)aminoaphthaline-1-sulfonic acid (EDANS), Texas Red, Eosine, and Bodipy and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, Allophycocyanin, Aminocoumarin, Bodipy-FL, Cy2, Cy3, Cy3.5, Cy5, Cy5.5, carboxyfluorescein (FAM), Cascade Blue, APC-Cy5, APC-Cy5.5, APC-Cy7, Coumarin, ECD (Red613), Fluorescein (FITC), Hexachlorfluoroscein (HEX), Hydroxycoumarin, Lissamine Rhodamine B, Lucifer yellow, Methoxycoumarin, Oregon Green 488, Oregon Green 514, Pacific Blue, PE-Cy7 conjugates, PerC, PerCP-Cy5.5, R-Phycoerythrin (PE), Rhodamine, Rhodamine Green, Rodamine Red-X, Tetratchlorofluoroscein (TET), TRITC, Tetramethylrhodamine, Texas Red-X, TRITC, XRITC, and Quantum dots. See, for example, Tyagi et al. *Nature Biotechnology* 16:49-53, (1998) and Dubertret et al., *Nature Biotechnology*, 19:365-370 (2001), incorporated herein by reference.

The invention also provides signaling probes that are wavelength-shifting. In one embodiment, one terminus of the probe has at least a harvester fluorophore and an emitter fluorophore, an adjacent terminus of the probe has at least a quencher moiety. See, for example, Tyagi et al., *Nature Biotechnology*, 18, 1191-1196 (2000), incorporated herein by reference. In one embodiment, the harvester fluorophore and the emitter fluorophore are at the same terminus, wherein the emitter fluorophore is at the distal end, and a quencher moiety is at an opposite terminus to the harvester fluorophore. The emitter fluorophore may be separated from the harvester fluorophore by a spacer arm of a few nucleotides. The harvester fluorophore absorbs strongly in the wavelength range of the monochromatic light source. In the absence of target sequence, both fluorophores are quenched. In the presence of targets, the probe fluoresces in the emission range of the emitter fluorophore. The shift in emission spectrum is due to the transfer of absorbed energy from the harvester fluorophore to the emitter fluorophore by fluorescence resonance energy transfer. These types of signaling probes may provide a stronger signal than signaling probes containing a fluorophore that cannot efficiently absorb energy from the monochromatic light sources. In one embodiment, the harvester fluorophore is fluorescein and the emitter fluorophore is 6-carboxyrhodamine 6G, tetramethylrhodamine or Texas red.

In another embodiment, one terminus of the probe has at least a fluorophore F1, and another adjacent terminus has at least another fluorophore F2. The two fluorophores are chosen so that fluorescence resonance energy transfer (FRET) will occur when they are in close proximity. When the probe is not bound to its target sequence, upon excitation at the absorption band of F1, the fluorescence of F1 is quenched by F2, and the fluorescence of F2 is observed. When the probe is bound to its target sequence, FRET is reduced or eliminated and the fluorescence of F1 will rise while that of F2 will diminish or disappear. This difference in fluorescence intensities can be monitored and a ratio between the fluorescence of F1 and F2 can be calculated. As residual fluorescence is sometimes observed in fluorophore-quencher systems, this system may be more advantageous in the quantitative detection of target sequence. See, Zhang et al., *Angrew. Chem. Int. Ed.*, 40, 2, pp. 402-405 (2001), incorporated herein by reference. Examples of FRET donor-acceptor pairs include but are not limited to the coumarin group and 6-carboxyfluorescein group, respectively.

In one embodiment, the signaling probe comprises a luminescent label and adduct pair. The interaction of the adduct with the luminescent label diminishes signal produced from the label. See Becker and Nelson, U.S. Pat. No. 5,731,148, incorporated herein by reference.

In another embodiment, the signaling probe comprises at least a dye dimer. When the probe is bound to the target sequence, the signal from the dyes are different from the signal of the dye in dimer conformation.

In yet another embodiment, the interacting pair may be an enzyme and an inhibitor of that enzyme, e.g., a nuclease and a nuclease inhibitor, a kinase and an inhibitor of the kinase, a protease and an inhibitor of the protease, a phosphatase and an inhibitor of the phosphatase, a caspase and an inhibitor of the caspase, or a ribozyme and an inhibitor of the ribozyme, or an antigen and an antibody that specifically binds to the antigen such that the detected target of the probe may be shuttled to a specific cellular localization of the antigen, e.g., to the synapse of a neuron, etc.

Conformation of Signaling Probes and Protease Probes or Other Probes

Double-Stranded Structure

Figure 1:
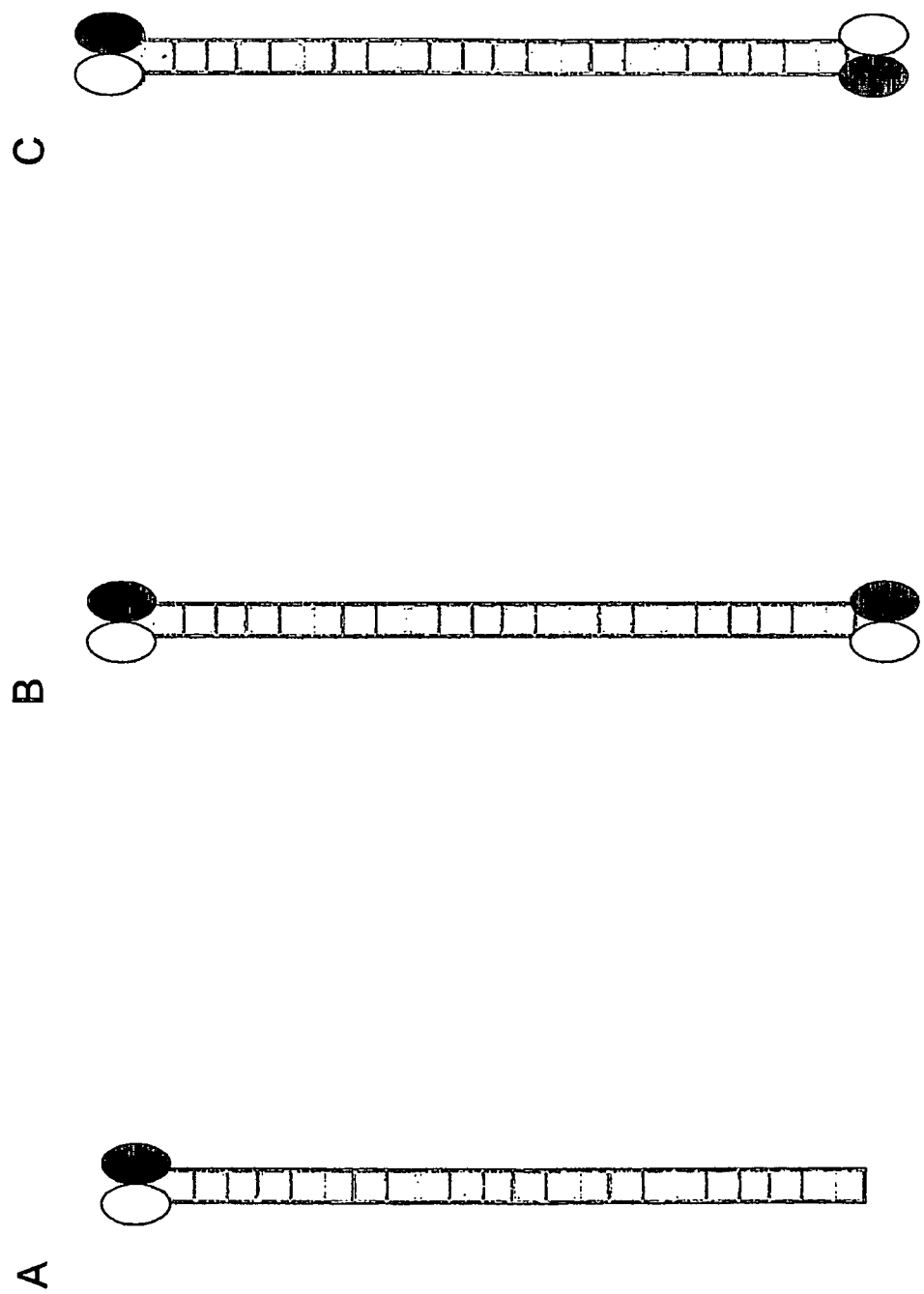

The present invention provides signaling or protease probes or other probe comprising at least two separate strands of nucleic acid that are designed to anneal to each other or form at least a mutually complementary region. At least one terminus of one strand is adjacent to a terminus of the other strand (FIG. 1). The nucleic acid may be DNA, RNA or modified DNA or RNA. The two strands may be identical strands that form a self-dimer (FIG. 8B). The strands may also not be identical in sequence.

The two separate strands may be designed to be fully complementary or comprise complementary regions and non-complementary regions. In one embodiment, the two separate strands are designed to be fully complementary to each other. In one embodiment, the two strands form a mutually complementary region of 4 to 9, 5 to 6, 2 to 10, 10 to 40, or 40 to 400 continuous basepairs at each end (see, e.g., FIG. 8, 9, 15, 22, 24 or 41). The strands may contain 5-7, 8-10, 11-15, 16-22, more than 30, 3-10, 11-80, 81-200, or more than 200 nucleotides or modified nucleotides. The two strands may have the same or a different number of nucleotides (FIG. 2). For example, one strand may be longer than the other (FIG. 2C). In one embodiment, the 5' end of one strand is offset from the other strand, or the 3' end of that strand is offset from the other strand, or both, wherein the offset is up to 10, up to 20, or up to 30 nucleotides or modified nucleotides.

The region that hybridizes to the target sequence may be in the complementary regions, non-complementary regions of one or both strands or a combination thereof. More than one target nucleic acid sequence may be targeted by the same signaling probe. The one or more targets may be on the same or different sequences, and they may be exactly complementary to the portion of the probe designed to bind target or at least complementary enough. In one embodiment, the two strands form a mutually complementary region at each end and the target complement sequence resides in the regions other than the mutually complementary regions at the ends (FIG. 8B)

In one embodiment, the signaling probe with at least two separate strands is a fluorogenic probe. In one embodiment, one strand has at least a quencher moiety on one terminus, and a fluorophore on an adjacent terminus of the other strand (FIG. 1). In one embodiment, each of the 5' and 3' terminus of one strand has the same or a different fluorophore, and each of the 5' and 3' terminus of the other strand has the same or a different quencher moiety (FIGS. 1B and 2A). In one embodiment, the 5' terminus of one strand has a fluorophore and the 3' terminus has a quencher moiety, and the 3' terminus of the other strand has the same or a different quencher moiety and the 5' terminus has the same or a different fluorophore (FIGS. 1C and 2B).

For the protease probe, in one embodiment, one strand has at least a proteolytic enzyme on one terminus, and an inhibitor of the proteolytic enzyme on an adjacent terminus of the other strand. In one embodiment, each of the 5' and 3' terminus of one strand has a proteolytic enzyme, and each of the 5' and 3' terminus of the other strand has an inhibitor of the proteolytic enzyme. In one embodiment, the 5' terminus of one strand has a proteolytic enzyme and the 3' terminus has an inhibitor of the proteolytic enzyme, and the 3' terminus of the other strand has an inhibitor of the proteolytic enzyme and the 5' terminus has a proteolytic enzyme.

Stem-Loop Structure

In another embodiment, the signaling or protease probe or other probe is a strand of nucleic acid or modified nucleic acid that comprises at least a mutually complementary region and at least a non-complementary region. In one embodiment, the probe forms a stem-loop structure. The stem region can be mutually complementary, or comprise mutually complementary regions and non-complementary regions (FIG. 4). For example, the stem region can have bulged nucleotides that are not base-paired (FIG. 4). The stem region can also contain overhang nucleotides at the 5' or 3' ends that are not base-paired (FIGS. 3B and 3C).

Figure 3:
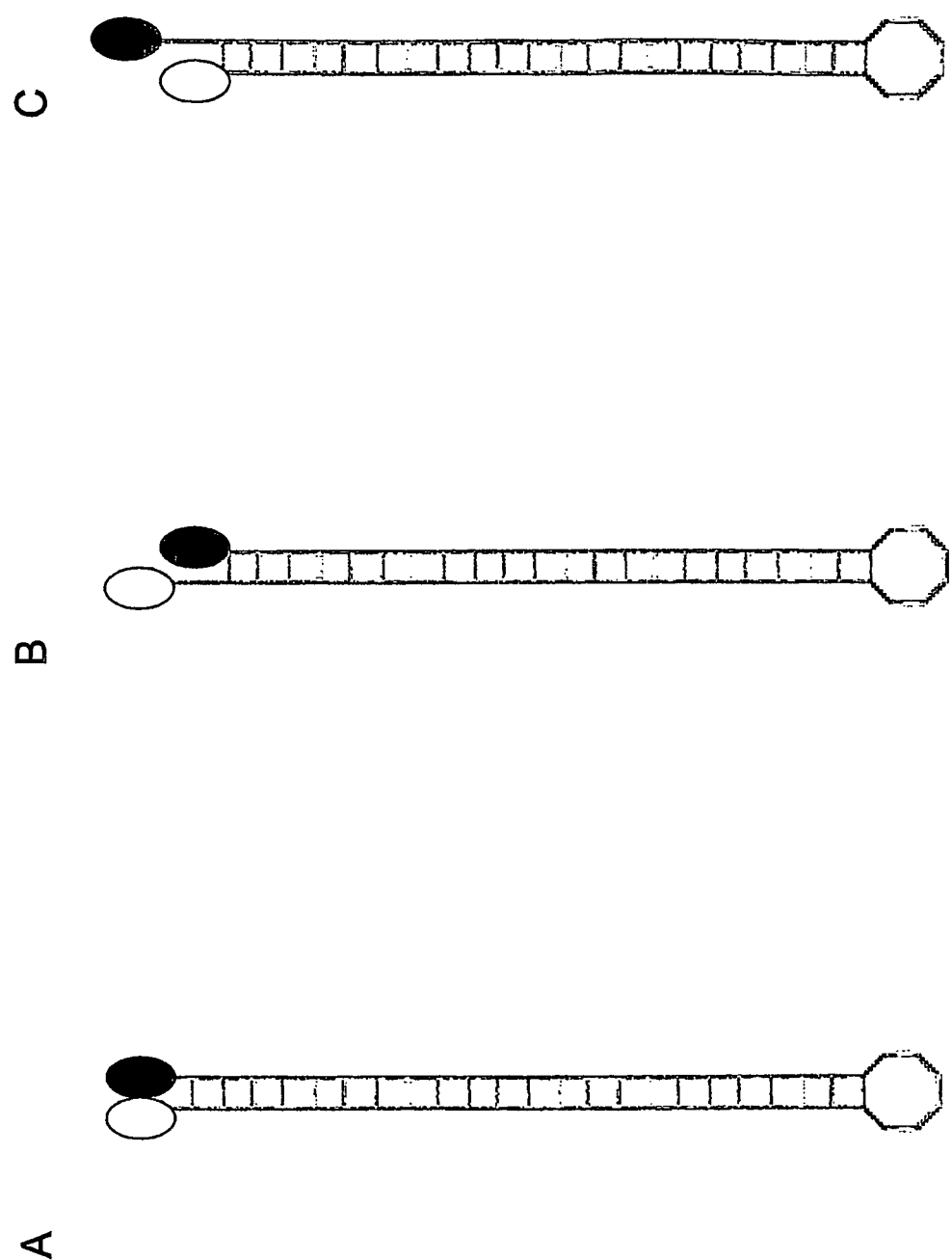

When the stem region is fully complementary, the stem region can include 3-4, 5-6, 7-8, 9-10, 2-6, 7-10, or 11-30 base-pairs (see, e.g., FIGS. 3 and 5). The loop region can contain 10-16, 17-26, 27-36, 37-45, 3-10, 11-25, or 25-60 nucleotides. In one embodiment, the stem region forms 4-10, 4, or 5 continuous basepairs (see, e.g., FIG. 23).

In one embodiment, the stem-loop structure comprises at least an interactive pair comprising two chemical groups, and one chemical group is at each terminus of the strand. In one embodiment, the signaling probe has at least a fluorophore and a quencher moiety at each terminus of the strand (FIGS. 3, 4 and 5). The protease probe has at least a proteolytic enzyme and an inhibitor of the proteolytic enzyme at each terminus of the strand.

In one embodiment, the stem region comprises two mutually complementary regions connected via a non-complementary region, the mutually complementary region adjacent to the interactive pair forms 5 to 9 basepairs, and the mutually complementary region adjacent to the loop region forms 4 to 5 basepairs (FIG. 8, 15, 21, 22, 24 or 41). In one embodiment, the non-complementary region is a single-stranded loop region (FIG. 8), a mismatch region (FIG. 15) or both. In another embodiment, the stem region comprises three mutually complementary regions connected via two non-complementary regions, the first mutually complementary region adjacent to the interactive pair forms 4 to 5 basepairs, the second mutually complementary region forms 2 to 3 basepairs, and the third mutually complementary region adjacent to the loop region forms 2 to 3 basepairs.

Figure 8:
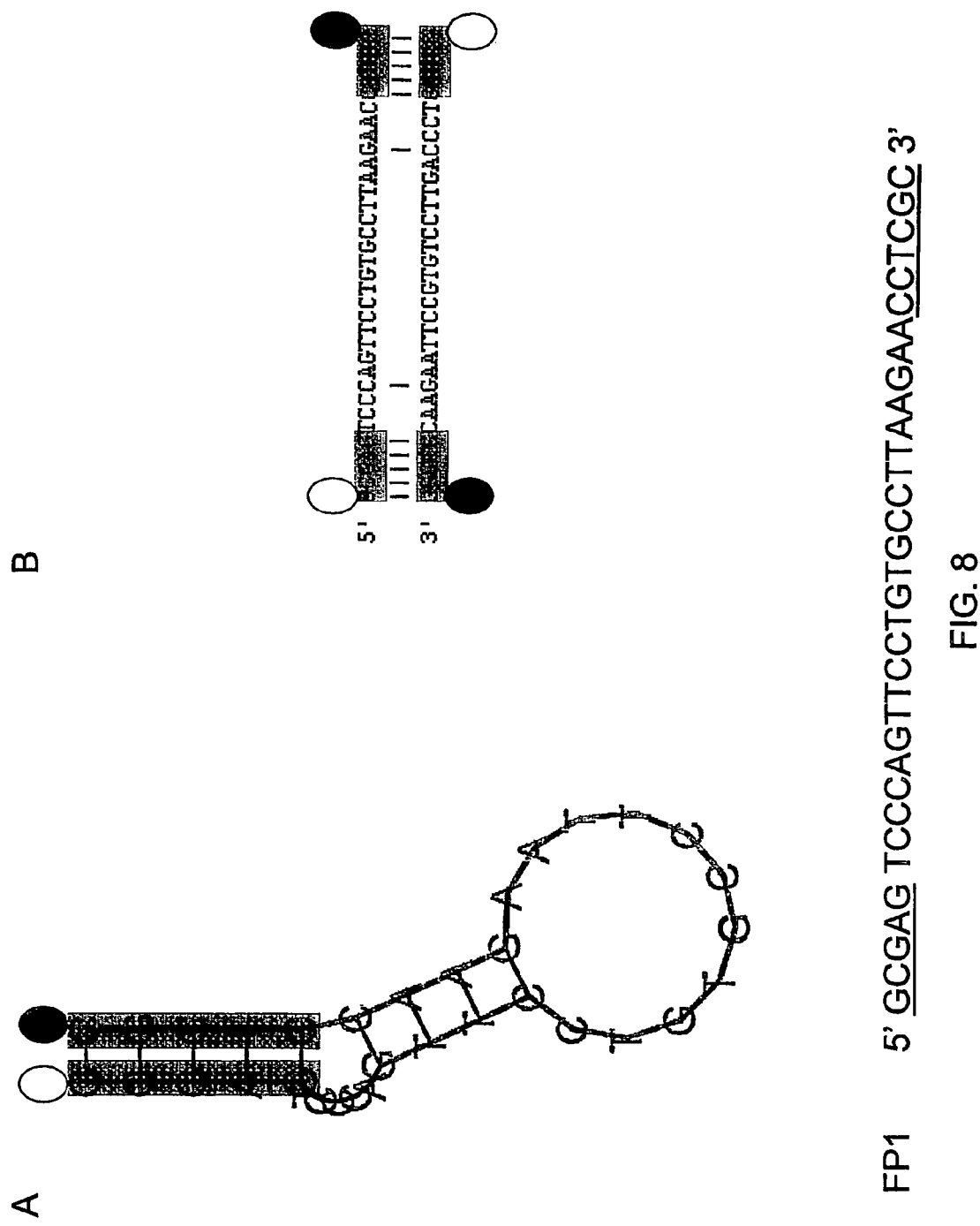
FIG. 8 shows the sequence and predicted native conformation of fluorescent probe FP1. The FP1 sequence comprises bases which are designed to be complementary to the target sequence and additional flanking bases. The flanking bases are underlined. Panel A shows the predicted structure of the sequence using DNA folding programs according to *Nucleic Acids Res.* 31: 3429-3431 (2003). Panel B shows predicted self dimerization of the FP1 sequence according to the oligoanalyzer 3.0 software available at the Integrated DNA Technologies SciTools website. In both Panels A and B, the flanking bases are shaded in grey, white and black ovals indicate fluorophore and quencher moieties, respectively.

In the stem-loop structure, the region that is complementary to the target sequence may be in one or more stem regions or loop regions, or both. The region in the stem that hybridizes to the target may be in the mutually complementary regions, non-complementary regions or both. In one embodiment, the target complement sequence is in the single-stranded loop region. In one embodiment, the regions other than the stem region adjacent to the interactive pair is the target complement sequence (FIG. 8). More than one target nucleic acid sequence may be targeted by the same probe. The one or more targets may be on the same or different sequences, and they may be exactly complementary to the portion of the probe designed to bind target or at least complementary enough.

The increase in stem length may increase the stability of the signaling probes in their closed conformation, and thus, may increase the signal to noise ratio of detectable signal. Exposure of these signaling probes to cells can be carried out at slightly elevated temperatures which are still safe for the cell followed by a return to normal temperatures. At the higher temperatures, the signaling probes would open and bind to their target if present. Once cooled, the signaling probes not bound to target would revert to their closed states, which is assisted by the increased stability of the stem. Similarly, other forces may be used to achieve the same outcome, for instance DMSO which is thought to relax base-pairing.

Three-Arm Junction Structure

In another embodiment, the signaling or protease probe or other probe is a strand of nucleic acid that forms a three-arm junction structure (FIGS. 6A and 6B). In this structure, a stem region and two stein-loop regions are connected to form a three-way junction. The stem regions can contain 2-5, 7-9, 10-12 base pairs. The loop of the stem-loop regions can contain 3-7, 8-10, 11-13 nucleotides or modified nucleotides.

In one embodiment, the three-arm junction structure comprises at least an interactive pair comprising two chemical groups, and one chemical group is at each terminus of the strand. In one embodiment, the probe has at least a fluorophore and a quencher moiety at each terminus of the strand. The protease probe has at least a proteolytic enzyme and an inhibitor of the proteolytic enzyme at each terminus of the strand.

Figure 9:
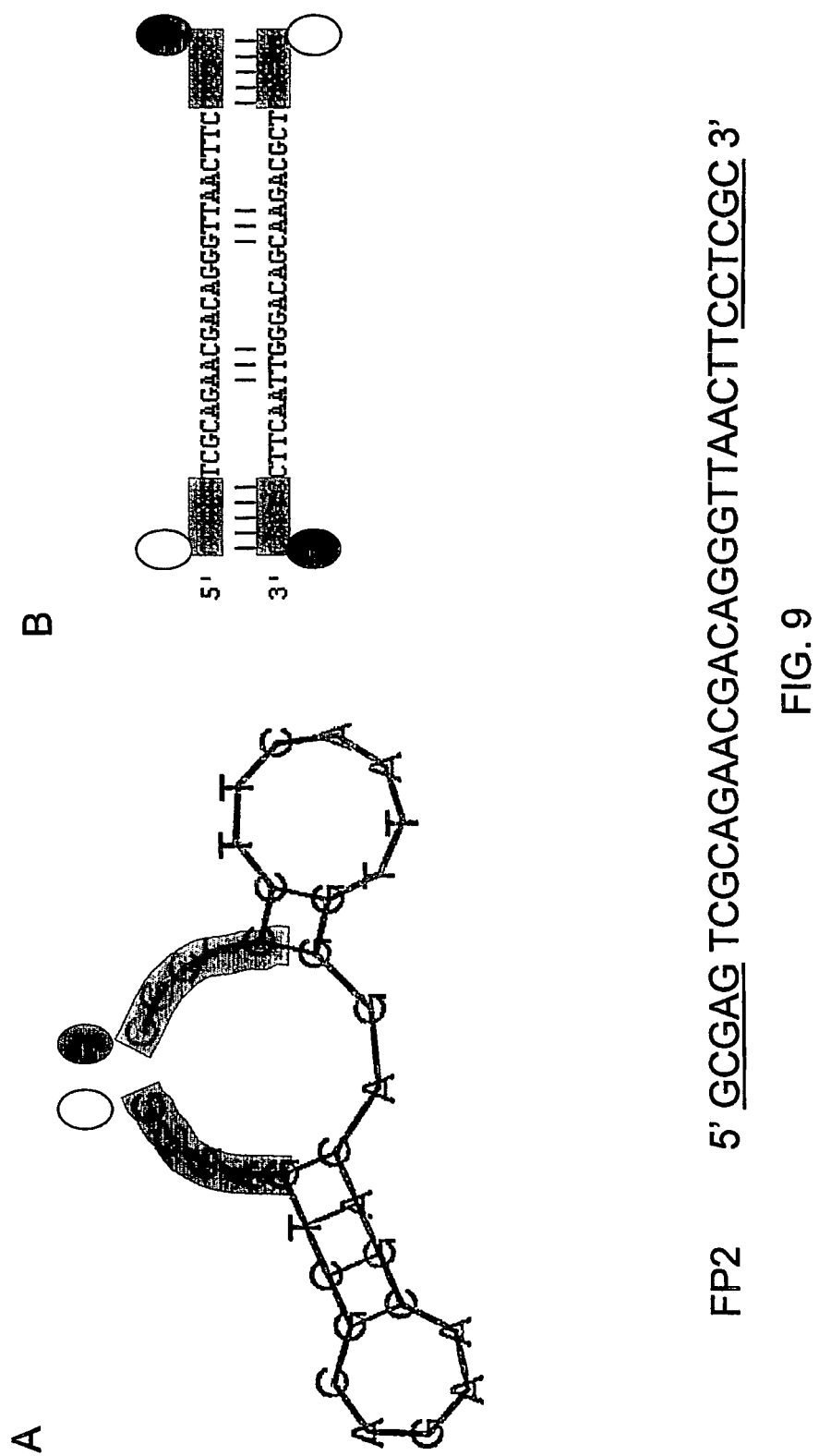
FIG. 9 shows the sequence and predicted native conformation of fluorescent probe FP2. The sequence comprises bases which are designed to be complementary to the target sequence and additional flanking bases. The flanking bases are underlined. Panel A shows the predicted structure of the sequence using DNA folding programs according to *Nucleic Acids Res.* 31: 3429-3431 (2003). It is likely that all or part of the shaded region form Watson-Crick basepairs, thereby forming a three-arm junction. Panel B shows predicted self dimerization of the FP2 sequence according to the oligoanalyzer 3.0 software available at the Integrated DNA Technologies SciTools website. In both Panels A and B, the flanking bases are shaded in grey, white and black ovals indicate fluorophore and quencher moieties, respectively. http://biotools.idtdna.com/analyzer/oligocalc.asp. In both Panels A and B, the flanking bases are shaded in grey, white and black ovals indicate fluorophore and quencher moieties, respectively.
Figure 10:
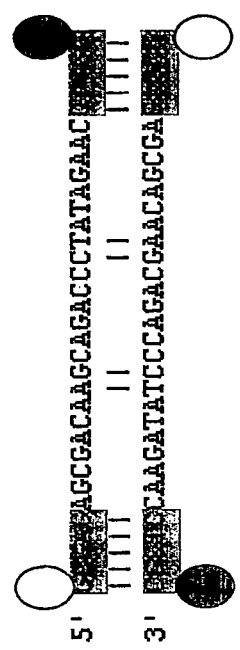
FIG. 10 shows the sequence and predicted native conformation of fluorescent probe FP3. The FP3 sequence comprises bases which are designed to be complementary to the target sequence and additional flanking bases. The flanking bases are underlined. The figure shows predicted self dimerization of the FP3 sequence according to the oligoanalyzer 3.0 software available at the Integrated DNA Technologies SciTools website. The flanking bases are shaded in grey, white and black ovals indicate fluorophore and quencher moieties, respectively.

In one embodiment, the stem region adjacent to the interactive pair forms 3 to 4, or 3 to 6 continuous basepairs, the stem region of the first stem-loop structure forms 4 to 5 continuous basepairs, and the stem region of the second stem-loop structure forms 2 to 3 continuous basepairs (FIG. 9). In one embodiment, the three regions are connected by a phosphodiester linkage or modified phosphodiester linkage via the arms of the stem regions. In one embodiment, the three regions are connected by 1 or 2 nucleotides or modified nucleotides via the arms of the stem regions.

The region in the stem that hybridizes to the target may be in the mutually complementary regions, non-complementary regions or both. In one embodiment, the target complement sequence is in the single-stranded loop region. In one embodiment, the regions other than the stem region adjacent to the interactive pair is the target complement sequence (FIG. 9). More than one target nucleic acid sequence may be targeted by the same probes. The one or more targets may be on the same or different sequences, and they may be exactly complementary to the portion of the probe designed to bind target or at least complementary enough.

Dumbbell Structure

Figure 11:
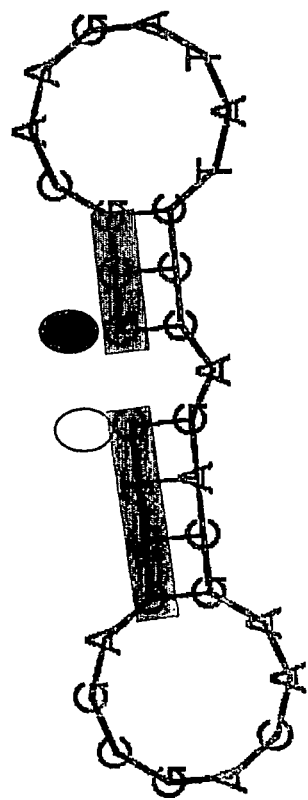
FIG. 11 shows the sequence and predicted native conformation of fluorescent probe FP4 (SEQ ID NO: 26). The FP4 sequence comprises bases which are designed to be complementary to the target sequence and additional flanking bases. The flanking bases are underlined. The figure (SEQ ID NO: 24) shows the predicted structure of the sequence using DNA folding programs according to *Nucleic Acids Res.* 31: 3429-3431 (2003). The flanking bases are shaded in grey, white and black ovals indicate fluorophore and quencher moieties, respectively.
Figure 14:
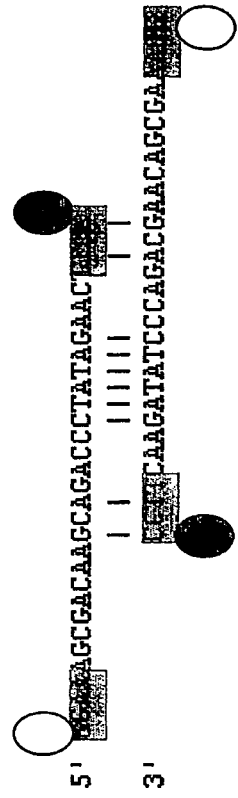
FIG. 14 shows the sequence and predicted native conformation of fluorescent probe FP7. The FP7 sequence comprises bases which are designed to be complementary to the target sequence and additional flanking bases. The flanking bases are underlined. The predicted self dimerization of the FP7 sequence according to the oligoanalyzer 3.0 software available at the Integrated DNA Technologies SciTools website is shown. The flanking bases are shaded in grey, white and black ovals indicate fluorophore and quencher moieties, respectively.
Figure 21:
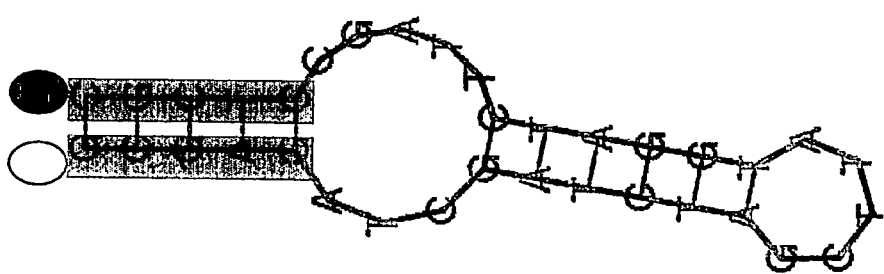
FIG. 21 shows the sequence and predicted native conformation of fluorescent probe FP14 (SEQ ID NO: 39). The FP14 sequence comprises bases which are designed to be complementary to the target sequence and additional flanking bases. The flanking bases are underlined. The figure (SEQ ID NO: 38) shows the predicted structure of the sequence using DNA folding programs according to *Nucleic Acids Res.* 31: 3429-3431 (2003). The flanking bases are shaded in grey, white and black ovals indicate fluorophore and quencher moieties, respectively.
Figure 22:
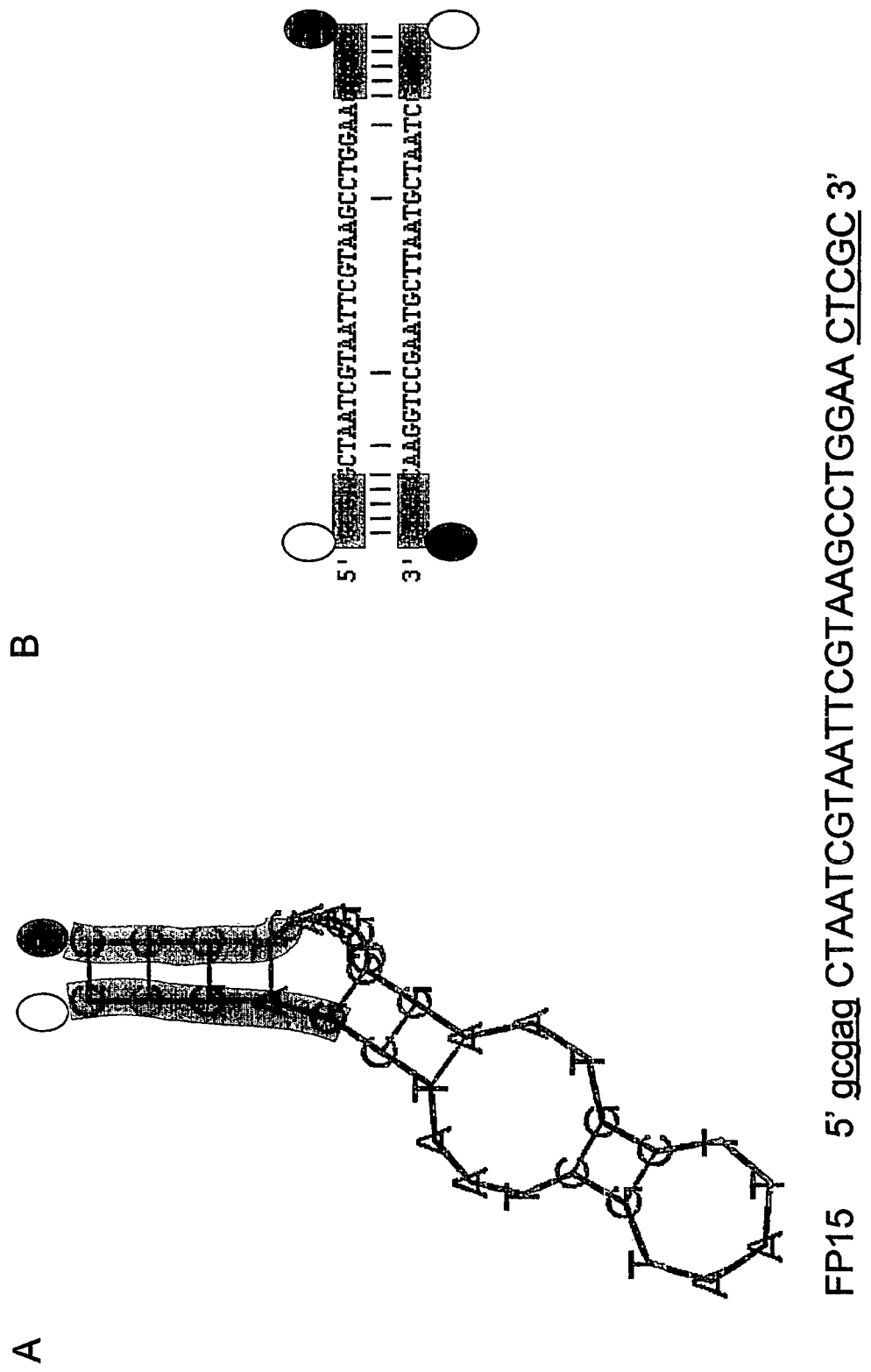

In another embodiment, the signaling or protease probe or other probe is a strand of nucleic acid that forms a dumbbell-shaped structure (FIG. 7 or 11). The structure is two stem-loop regions connected via one arm of the two stem regions. The stem regions can contain 3-5, 7-9, 10-12 base pairs. The loop of the stem-loop regions can contain 5-7, 8-10, 11-13 nucleotides. In one embodiment, the dumbbell structure has one stem region of 3 continuous basepairs, and one stem region of 4 continuous basepairs. In one embodiment, the two stem regions are connected by 1 or 2 nucleotides or modified nucleotides. In another embodiment, the two stem regions by a phosphodiester linkage or modified phosphodiester linkage. In one embodiment, the stem-loop structure, dumbbell structure or three-arm junction structure has more than 30 nucleotides or modified nucleotides.

In one embodiment, the signaling probe has at least a fluorophore and a quencher moiety at each terminus of the strand. The protease probe has at least a proteolytic enzyme and an inhibitor of the proteolytic enzyme at each terminus of the strand.

The region in the stem that hybridizes to the target may be in the mutually complementary regions, non-complementary regions or a combination thereof. In one embodiment, the target complement sequence is in the single-stranded loop region. In one embodiment, the target complement sequence is the region other than the two stem regions. More than one target nucleic acid sequence may be targeted by the same probe. The one or more targets may be on the same or different sequences, and they may be exactly complementary to the portion of the probe designed to bind target or at least complementary enough.

DNA or RNA folding programs are available in the art to predict the conformation of a given nucleic acid or modified nucleic acid. Such folding programs include but are not limited to the programs described in *Nucleic Acids Res.* 31: 3429-3431 (2003) and the oligoanalyzer 3.0 software available at the Integrated DNA Technologies SciTools website; hereby incorporated by reference. Such folding programs often predict a number of energetically more favorable structures. In other embodiments, the invention encompasses the energetically more favorable structures of probes FP1-18 (FIGS. 8-24 and 41) that are predicted by folding programs. If the energy of the conformation is measured by free energy, the lower free energy value (negative) indicates that the conformation is more energetically favorable.

Chemical Modification of Signaling and Protease Probes or Other Probe

The present invention also provides signaling or protease probes or other probes which are chemically modified. One or more of the sugar-phosphodiester type backbone, 2'OH, base can be modified. The substitution of the phosphodiester linkage includes but is not limited to —OP(OH)(O)O—, —OP(O$^-$M$^+$)(O)O—, —OP(SH)(O)O—, —OP(S$^-$M$^+$)(O)O—, —NHP(O)$_2$O—, —OC(O)$_2$O—, —OCH$_2$C(O)$_2$ NH—, —OCH$_2$C(O)$_2$O—, —OP(CH$_3$)(O)O—, —OP(CH$_2$C$_6$H$_5$)(O)O—, —P(S)(O)O— and —OC(O)$_2$NH—. M$^+$ is an inorganic or organic cation. The backbone can also be peptide nucleic acid, where the deoxyribose phosphate backbone is replaced by a pseudo peptide backbone. Peptide nucleic acid is described by Hyrup and Nielsen, *Bioorganic & Medicinal Chemistry* 4:5-23, 1996, and Hydig-Hielsen and Godskesen, WO 95/32305, each of which is hereby incorporated by reference herein.

The 2' position of the sugar includes but is not limited to H, OH, C$_1$-C$_4$ alkoxy, OCH$_2$—CH=CH$_2$, OCH$_2$—CH=CH—CH$_3$, OCH$_2$—CH=CH—(CH$_2$)$_n$CH$_3$ (n=0, 1 . . . 30), halogen (F, Cl, Br, I), C$_1$-C$_6$ alkyl and OCH$_3$. C$_1$-C$_4$ alkoxy and C$_1$-C$_6$ alkyl may be or may include groups which are straight-chain, branched, or cyclic.

The bases of the nucleotide can be any one of adenine, guanine, cytosine, thymine, uracil, inosine, or the forgoing with modifications. Modified bases include but are not limited to N4-methyl deoxyguanosine, deaza or aza purines and pyrimidines. Ring nitrogens such as the N1 of adenine, N7 of guanine, N3 of cytosine can be alkylated. The pyrimidine bases can be substituted at position 5 or 6, and the purine bases can be substituted at position 2, 6 or 8. See, for example, Cook, WO 93/13121; Sanger, Principles of Nucleic Acid Structure, Springer-Verlag, New York (1984), incorporated herein by reference.

Derivatives of the conventional nucleotide are well known in the art and include, for example, molecules having a different type of sugar. The O4' position of the sugar can be substituted with S or CH$_2$. For example, a nucleotide base recognition sequence can have cyclobutyl moieties connected by linking moieties, where the cyclobutyl moieties have hetereocyclic bases attached thereto. See, e.g., Cook et al., International Publication WO 94/19023 (hereby incorporated by reference herein).

Other chemical modifications of probes useful in facilitating the delivery of the probes into cells include, but are not limited to, cholesterol, transduction peptides (e.g., TAT, penetratin, etc.).

Methods

The methods of this invention are based upon the ability of signaling probes to produce a detectable signal upon hybridization to target RNA sequences in living cells. The signal produced should be detectably higher than that produced in control cells (e.g., background fluorescence). Thus, it is not necessary that the control cells produce no fluorescence at all. In one embodiment, the method is for detecting or quantitating RNA. One method is to isolate cells or generate cell lines that express at least an RNA. In any of the methods of the invention that involve isolating cells, the cells may be cultured and may also be cultured to generate cell lines. A DNA construct encoding an RNA or an RNA and a tag sequence is introduced into cells. The DNA construct may be integrated at different locations in the genome of the cell. Integration at one or more specific loci may also be accomplished. Then, the transfected cells are exposed to the signaling probe, which generates a detectable signal upon binding to the target RNA or tag sequence. The cells that produce the detectable signal are isolated. Cells can be isolated and cultured by any method in the art, e.g., cells can be isolated and plated individually or in batch. Cell lines can be generated by growing the isolated cells.

Any of the method of the invention may be carried out using a selection marker. Although drug selection (or selection using any other suitable selection marker) is not a required step, it may be used to enrich the transfected cell population for stably transfected cells, provided that the transfected constructs are designed to confer drug resistance. If selection using signaling probes is performed too soon following transfection, some positive cells may only be transiently and not stably transfected. However, this can be minimized given sufficient cell passage allowing for dilution or loss of transfected plasmid from non-stably transfected cells. Some stably integrated plasmids may not generate any RNA corresponding to cloned cDNA inserts. Others may generate RNAs which may not be or may be inefficiently detected by the signaling probes.

The RNAs can have one or more of the following different roles: messenger RNAs that encode proteins, fusion proteins, peptides fused to proteins, export signals, import signals, intracellular localization signals or other signals, which may be fused to proteins or peptides; antisense RNA, siRNA, structural RNAs, cellular RNAs including but not limited to such as ribosomal RNAs, tRNAs, hnRNA, snRNA; random RNAs, RNAs corresponding to cDNAs or ESTs; RNAs from diverse species, RNAs corresponding to oligonucleotides, RNAs corresponding to whole cell, tissue, or organism cDNA preparations; RNAs that have some binding activity to other nucleic acids, proteins, other cell components or drug molecules; RNAs that may be incorporated into various macromolecular complexes; RNAs that may affect some cellular function; or RNAs that do not have the aforementioned function or activity but which may be expressed by cells nevertheless; RNAs corresponding to viral or foreign RNAs, linker RNA, or sequence that links one or more RNAs; or RNAs that serve as tags or a combination or recombination of unmodified mutagenized, randomized, or shuffled sequences of any one or more of the above. RNAs may be under the control of constitutive or conditional promoters including but not limited to inducible, repressible, tissue-specific, heat-shock, developmental, cell lineage specific, or temporal promoters or a combination or recombination of unmodified or mutagenized, randomized, shuffled sequences of any one or more of the above.

In one embodiment, the signaling probes are fluorogenic probes. Fluorescence cell sorter or related technology can be used with fluorogenic probes to identify and/or separate cells exhibiting a certain level or levels of fluorescence at one or more wavelengths. Being able to detect reliably and efficiently mRNAs as well as other RNAs in living cells enables their use to identify and, if desired, separate cells based on their desired characteristics, for instance by using a Fluorescence Activated Cell Sorter (FACS). FACS technology currently allows sorting at up to 70,000 cells per second. 5,000,000 cells can be sorted in less than 2 minutes.

1. Generating Protein-Expressing Cell Lines

Some of the most tedious steps involved in generating cell lines are eliminated by the application of signaling probes as described herein. In one embodiment, following transfection with a DNA construct encoding a desired gene, one introduces into these cells fluorogenic probes designed to recognize the message of the gene of interest. This step can be performed following selection using a selection marker, e.g., drug selection provided that the transfected DNA construct also encodes drug resistance. Those cells transcribing the gene will fluoresce. Subsequent FACS analysis results in the isolation of the fluorescent cells which may then be grown to give rise to cell lines expressing the gene of choice.

In one embodiment, the signaling probes are designed to be complementary to either a portion of the RNA encoding the protein of interest or to portions of their 5' or 3' untranslated regions. If the signaling probe designed to recognize a messenger RNA of interest is able to detect endogenously existing target sequences, the proportion of these in comparison to the proportion of the target sequence produced by transfected cells is such that the sorter is able to discriminate the two cell types. The gene of interest may be tagged with a tag sequence and the signaling probe may be designed so that it recognizes the tag sequence. The tag sequence can either be in frame with the protein-coding portion of the message of the gene or out of frame with it, depending on whether one wishes to tag the protein produced.

Additionally, the level of expression of the gene of interest in any given cell may vary. This can be due to a variety of factors that can influence the level of RNA expression including but not limited to the quantity or copy number of DNA that was transfected into a cell, the site of any resulting genomic integration of the DNA and the integrity of the DNA and resulting expression from it following genomic integration. One may apply FACS to evaluate expression levels and differentially select individual cells expressing the same gene.

2. Generating Cell Lines that Down Regulate Genes

There are several studies describing the generation of cell lines which express not RNA that encodes a protein, but rather one that is the antisense of a gene or portion of a gene. Such methods aim to reduce the amount of a specific RNA or protein in a given cell. The steps described above for the generation of protein-expressing cell lines are equally applicable here and virtually identical except that here the signaling probe is designed to detect an RNA which is an antisense RNA.

Not all attempts at making stably transfected antisense-expressing cell lines result in cell lines where the expression of the targeted protein is affected sufficiently. This difficulty has made it less worthwhile to pursue the production of such cell lines. Given the ease of the procedure described here, one easily assays the effectiveness of numerous different genetic sequences for their ability to yield active, i.e., effective antisense expressing cell lines. One can then analyze these to determine which exhibit appropriate expression profiles where the down regulation of targeted genes can be analyzed.

RNA interference is an alternate approach which also aims to decrease transcription levels of specific genes. RNA interference may be induced transiently using chemically synthesized siRNA or DNA constructs encoding short siRNAs, or it may be stably induced if stable cells appropriately expressing the short siRNAs are generated. The methods described here can also be used to analyze or isolate cells or cell lines based on their expression of such siRNAs.

The application of the methods described here to obtain cells expressing RNAs that induce RNA interference is additionally important because it will help overcome some complexities currently encountered in such cells. For instance, although RNA interference is performed in order to reduce the transcriptional levels of targeted RNAs and may cause downstream effects on the transcriptional levels of other RNAs, it has also been shown to reduce the transcriptional levels of RNAs that are not intended targets. The identity of these unintended targets varies depending on the sequence of the RNA that is used to induce RNA interference. This is a complicating feature of using RNA interference in cells as results may be compromised by such unintended consequences. Because the methods described here enable the efficient generation of multiple stable cells each expressing for instance, a different RNA sequence used to induce RNA interference for the same gene, each of these sequences can be assayed in the cell for its effects on the transcriptional levels of other genes. Analysis of this information can be used to distinguish RNAs that have decreased transcriptional levels, of which the decrease is not due to a decreased expression level of the targeted RNA. RNA interference has rapidly gained popularity as it has been successfully used to overcome difficulties associated with achieving specific down-regulation using antisense RNA. Our methods may be helpful in determining the most effective sequences for more specific RNA interference having reduced non-specific activity. Because the methods also provide a method for selection of the most effective and specific antisense, they also represent a method of identifying effective antisense RNAs.

3. Differentiating Between Cells Based on Cell Surface-Localized Antigens

Immunologists and others have long used the FACS to sort cells. Generally, this method is based on labeling cell-surface localized proteins with differentially labeled probes, usually fluorophore-labeled antibody probes. For instance, cells positive for expression of cell surface localized proteins may be carried out. This method is most commonly used under conditions designed to preserve the integrity of the cell and maintain its viability.

In accordance with the present invention, to detect the presence of cell surface localized protein, a signaling probe is made to target the mRNA encoding the protein of interest. The signaling probe is introduced into cells by transfection without abrogating cell viability. Then, the cell sorter is used to isolate positive-scoring cells. Additionally, if a combination of signaling probes is used, each targeted to the mRNA of one of the proteins of interest, each can be labeled differently. If cells have a greater number of targets than what can be detected in a single application of FACS, multiple rounds of sorting are performed to sort cells.

The methods described here also enable the analysis or sorting of cells for other cellular RNAs, for instance mRNAs that code for proteins that are internally localized or secreted from the cell, or RNAs that do not code for protein. As a result, one or more of the cellular RNAs described previously may be detected as targets, including RNAs encoding proteins which are inaccessible to the commonly used antibody probes or for which probes have not yet been developed. These may include membrane-associated, membrane-spanning, membrane-anchored, cytoplasmic, or nucleoplasmic proteins.

4. Assaying Cells for the Expression of Specific RNAs and Quantifying the Level of RNA Expression in Cells If the target RNA of a fluorogenic probe that is introduced into a cell is present, the cell will fluoresce. This information can be qualitatively assessed by use of Fluorescence Microscopy (including confocal, laser-scanning or other types of microscopy) or FACS, and it is also quantifiable by either of these. For instance, instead of performing in situ reverse-transcription polymerase chain reaction (RT-PCR) on slices of tissues to determine a pattern of expression for a particular RNA, a signaling probe is used to carry out the same experiment. Moreover, using a combination of differently fluorescent fluorogenic probes, each targeting a specific RNA, one assays for the presence or quantity of several RNAs of interest in one step. Detection of RNAs (in fixed samples) can be performed at temperatures empirically determined to limit non-target specific signal generation. It is common practice to establish optimal temperature conditions for target detection when using nucleic acid probes. (Localization of Antigens in Combination with Detection of RNAs in Cells and Tissues)

Using fixed cells or tissue slices, one uses immunocytochemistry to describe the localization of the protein antigens recognized, and using signaling probe targeting specific RNAs, one co-localizes in the same samples the RNAs of interest. It has been shown that fluorogenic probes targeted to RNAs function in fixed cells.

5. Generating Cell Lines Expressing Multiple RNAs or Proteins

Using the methods of the present invention, one very quickly generates stably transfected cell lines expressing any number of RNAs or proteins, even without the need to maintain these cells in the presence of a mixture of numerous selective drugs (or using other selective agents). Following gene transfection and optionally, drug-selection, a combination of signaling probes, one to the message for each protein, is introduced into the cells. By designing the target complementary sequence of each fluorogenic probe to hybridize to the mRNA of only one of the genes or to the tag sequences with which the messages may be associated, each signaling probe is designed to recognize the mRNA encoded by only one of the genes. In one embodiment, the cells are then sorted by FACS. By selecting for one or more signals, a variety of cell lines is generated in a single application.

One may have a need to produce a cell line expressing a number of RNAs of interest that is above the number that may be identified in a single application of FACS. For instance, it would be highly informative to have a cell line in which are over-expressed all of the proteins and RNA sequences thought to be involved in the formation of a particular complex or involved in a biological pathway. For example, RNAs or proteins in the same or related biological pathway, RNAs or proteins that act upstream or downstream of each other, RNAs or proteins that have a modulating, activating or repressing function to each other, RNAs or proteins that are dependent on each other for function or activity, RNAs or proteins that form a complex or bind to each other, or RNAs or proteins that share homology (e.g., sequence, structural, or functional homology). If the number of RNAs required is greater than can be analyzed in one application of FACS, then to achieve this, the steps described above are repeated using cells already expressing a combination of some of the RNAs as the host cells into which would be transfected additional constructs encoding additional RNAs. Multiple rounds of the methods described may be used to obtain cells expressing all or a subset of the RNAs that are required.

If multiple RNAs to be expressed are all cloned into constructs conferring upon cells resistance to the same drug, in one embodiment, FACS can be used to isolate cells expressing all of the desired RNAs. In the case where the sequences are stably integrated into the genome, it is desired that the cells not lose expression of any of the sequences. However, it is possible that one or more of the sequences could be lost. If this is the case, one increases the concentration of the selective drug or selection agent in the media in which these cells are grown, making this possibility less likely. Alternatively, one uses constructs each of which confers resistance to a different drug, and maintains cells in a mix of appropriate drugs. Also, a subset of the constructs to be stably transfected into cells may be chosen so as to encode a resistance gene for one drug, and another subset to encode a resistance gene for another drug.

Moreover, if some cells of a cell line lose expression of an RNA of interest, then as one resort, the first experiment to isolate the cell line as described above is repeated and new cells obtained. Alternatively, the mixture of cells described are analyzed by FACS, with the aim of re-isolating cells expressing all of the desired RNAs. This is a very useful procedure as it again yields cells which give rise to a cell line with the same genetic make-up of the original cell line selected.

The approaches described above yield an unlimited supply of cells expressing any combination of proteins and RNA sequences, amenable to virtually unlimited methods of analysis. Yet it is possible that a protein that is overexpressed may be toxic to the cell, and as will be discussed later, this possibility can be readily addressed.

The ease with which it is possible to re-isolate cells expressing all of the desired RNAs from cells which no longer express all of the RNAs makes it possible to maintain cell lines in the presence of no drug or minimal concentrations of drug. The methods described here also enable the re-application of signaling probes to cells or cell lines generated previously. For example, to determine if and to what extent the cells are still positive for any one or more of the RNAs for which they were originally isolated.

6. Generating Cell Lines Dramatically Over-Expressing One or More RNAs or Proteins For each gene that is to be highly over-expressed, for example, two or more sequences for the same gene are first cloned into DNA constructs optionally also conferring drug resistance or other selectable marker. Each of the multiple sequences for each gene is designed to include the sequence encoding a different tag sequence. In one embodiment, following transfection of the DNA constructs into cells and subsequent selection, fluorogenic probes, each of which is targeted to only one tag sequence and differentially fluorescently labeled, are introduced into the cells and the cell sorter is used to isolate cells positive for their signals. Such cells have integrated into their genomes at least one copy of each of the differentially tagged sequences, and thus the expression of the sequence of interest occurs from an increased number of copies of essentially the same sequence of interest. The sequence of interest may be integrated at different locations of the genome in the cell. This method is used in conjunction with the use of the FACS to pick out those cells scoring most intensely for the signal of each fluorophore. A portion or all of the different tags may be identical such that a common signaling probe directed against this common sequence may be used to detect all of the various tags in cells.

7. Generating Cell Lines Expressing Multiple Antisense RNAs

Stably transfected cell lines producing multiple antisense messages are created as follows. Such antisense messages target either mRNAs or other RNAs. One selects cells which express at different levels any one of the antisense sequences transfected. Through repeated rounds of stable transfections, one readily selects cells that would give rise to stably transfected cell lines which express the antisense message of an unlimited number of RNAs.

Of course, cells expressing other RNAs other than antisense RNAs can be prepared by the methods described herein. Such RNAs include but are not limited to one or more of mRNA, rRNA, siRNA, shRNA, other structural RNAs such as hnRNA, tRNA, or snRNA, RNAs that have RNA interference activity, RNAs that serve as tags, etc 8. Generating Libraries of Cell Lines A plurality of cells are transfected with DNA constructs that form an expression library. Expression libraries of DNA sequences can include any of the kinds that are known in the art or a mixture of these, including but not limited to cDNA or EST libraries generated from, e.g., whole organisms, tissues, cells or cell lines, and synthetic libraries including but not limited to oligonucleotides or sequences coding for peptides. Similarly, libraries of DNA constructs not specifically designated as expression libraries may be used. For instance, a DNA construct library may include sequences of DNA that may have regulatory functions such as promoter, repressor, or enhancer elements, and these may be constitutive, inducible or repressible. Likewise, DNA construct libraries may comprise large segments of DNA such as entire or partial genetic loci or genomic DNA, from which transcription may occur. Any of these expression libraries of DNA constructs may each be wholly or partially mutagenized, randomized, recombined, shuffled, altered or treated in any combination thereof. Additionally, any of these types of libraries may further comprise at least one tag that is expressed and that may be used as a target for the signaling probes.

Expression libraries of DNA sequences for specific classes of proteins can be made and used to generate cell line libraries. For instance, cDNAs for protein kinases can be cloned into expression constructs comprising a tag sequence. Cells stably expressing different kinases can be obtained and used to generate a cell line library limited to cell lines expressing kinases. The class of sequences can be chosen to meet further applications such as drug screening.

Libraries of cell lines can also express classes of proteins having sequence homology, belonging to the same protein family or within a functional family, and also proteins defined by their role in a given protein pathway or complex or system. For instance, in a drug screen for compounds which may bind to various HIV proteins, a cell line library where each cell line expresses a different HIV protein can be made and used for screening drug compounds.

Libraries of cell lines may be used to assay secreted peptides or proteins having a desired activity. First, a cell line library is made using an expression library (for peptides, proteins, ESTs, cDNAs, etc.) additionally encoding an export signal translated in frame with the peptides/proteins. Expressed peptides/proteins are secreted into the growth medium. The effect of these peptides on a particular activity can then be determined given an appropriately designed assay. Tissue culture supernatant from the cell lines can be collected and applied to test cells to assay for the activity.

In addition, a library of cell lines may be generated for instance by transfecting an expression library into cells, and optionally, first selecting cells transfected with the expression library (for instance, using a signaling probe directed against a tag that is included in the expression library) and then exposing the cells to one or more signaling probes directed against one or more RNAs of interest. This would enable one to express various RNAs in cells and determine which of these RNAs results in the downstream transcriptional upregulation or downregulation of one or more RNAs of interest.

9. Generating Cell Lines which are Functional Knock-Outs for One or More Proteins The methods of the present invention provide the means to prepare functional knock-outs in cultured cells. One generates cell lines which are functional knock-outs of any one protein of interest by generating cells expressing from multiple loci virtually the same antisense RNA or siRNA having RNA interference activity to a unique RNA sequence. Any of the methods of the invention using siRNA may also be carried out using shRNA. For instance, one transfects into cells multiple constructs each of which would encode either the antisense RNA for a particular gene or siRNA having RNA interference activity for the gene, or both. Here each antisense RNA sequence differs only in that each would be tagged with the nucleotide sequence of a unique tag sequence. One selects those cells expressing one or more or all of the differentially-tagged antisense RNAs. Similarly, the presence of each siRNA or sh RNA with RNA interference activity would be determined by detection of a tag with which each siRNA or shRNA is associated. Because the FACS is used to quantify fluorescence as previously described, this feature enables one to select for those cells most strongly expressing any one or more of the antisense sequences. One could isolate cells exhibiting the desired expression levels of the targeted RNA, or little or no expression of it due to expression of any number or combination of expressed RNAs, which act to decrease the expression level of the targeted RNA.

Importantly, one or more of different antisense sequences and siRNAs having RNA interference activity targeting the same gene may be used in this approach. For instance, some of the antisense RNAs, the expression of which is selected for by using signaling probes and the FACS, is designed so as to target a particular region of the messenger RNA for the gene, whereas others are designed such that they target an alternate portion of the same messenger. In order to generate cell lines which are functional knock-outs of a protein of interest, one stably transfects into cells as many genetic sequences encoding similar or different antisense RNAs or siRNAs having RNA interference activity to the same gene of interest as is necessary for the production of a cell line which exhibits no detectable levels of expression of the protein of interest, or alternatively, acceptably low levels of expression.

Moreover, one generates cell lines in which multiple proteins are functionally knocked-out or have reduced expression levels by repeating the procedure described above while targeting any number of sequences to be knocked-out functionally by antisense or siRNA. For instance, to study the function of a complex of proteins, one knock-outs or reduces the expression levels of one, all, or any combination of the proteins making up the complex.

10. Generating Cell Lines which are Functional Knock-Outs of Only Selected Alternatively Spliced Forms of One or More Genes Differentially spliced versions of a single gene are often translated into proteins with differing functions. Using the methods of the present invention, one generates cell lines in which only selected alternatively spliced forms of one or more proteins are functional knock-outs or are reduced in expression levels. For example, by designing antisense or siRNAs that would target only those alternatively spliced versions of the messenger RNA of the gene that one would like to eliminate from the cell, one functionally knock-outs all of the alternatively spliced RNAs of the gene of interest, or sufficiently reduces their expression levels to desired levels except for those alternatively spliced messages which are of interest.

11. Generating Cell Lines Expressing One or More RNAs or Proteins a while Functionally Knocked-Out for One or More Other Proteins For instance, for a given group of proteins that is thought to interact with each other, one can study their interactions by generating stably transfected cell lines in which one or more of the proteins of interest are functionally knocked-out or have reduced expression levels by the cell's expression of antisense or siRNAs (or shRNAs). The function of the remaining proteins of interest in the cell can then be studied, but perhaps more interestingly, such a cell could be further altered by further manipulating it such that it will now over-express one or more of the remaining proteins of interest. In addition, one can over-express or eliminate or reduce the expression of additional proteins in cells. Again, it is possible that overexpression of certain proteins or a functional knock out of certain proteins may be lethal to cells. This is a problem that will be addressed below.

Analogous methods can be used to randomly up or down-regulate genes by introduction of DNAs with direct or indirect roles in transcriptional regulation. For instance, DNA sequences including but not limited to one or a combination of a promoter, enhancer, or repressor sequences, or a sequence which has some other binding or functional activity that results in the modulation of transcriptional levels for one or more RNAs can be transfected into cells. The activity of these elements may be constitutive, inducible or repressible. The signaling probes to one or more specific RNAs can be used to identify or isolate cells where the expression levels of these RNAs have been increased or decreased. Stable integration of some DNA sequences using the methods described may randomly sufficiently turn on or shut off transcription from genetic loci. These cell line libraries can be screened for cells which are effectively overexpressing or knocked-out for specific genes. Cells with desired levels of one or more RNAs can be selected in this way. Multiple rounds of this procedure may be performed, if necessary, to isolate cells having the desired expression profiles for multiple RNAs of interest.

12. Generation of Transgenic Mice

For some purposes, the study of cells in culture is not sufficient. The methodology described above, however, also lends itself towards the manipulation of embryonic stem cells. Embryonic stem cells may be obtained that could either express multiple RNAs or proteins or act as functional knock-outs of multiple proteins or a subset of the alternatively spliced forms of multiple proteins, etc., following the above procedures. Such embryonic stem cells are then used as the basis for the generation of transgenic animals.

Cells isolated according to the methods described may be implanted into organisms directly, or their nuclei may be transferred into other recipient cells and these may then be implanted. One use could be to generate transgenic animals and other uses may include but are not limited to introducing cells which synthesize or secrete cellular products into the organism and cells which are engineered to carry out desired roles in the organism.

13. Generating Inducible Stably Transfected Cell Lines

The over-expression or the lack of expression of certain proteins or RNAs in cells may be lethal or damaging. Yet it may be of critical importance to study a cell over-expressing a toxic protein or RNA, or one which is a functional knock-out of a protein or RNA, without which the cell is unable to survive. To this end, one generates stably transfected cells where selected RNAs having such deleterious effects on the cell are under the control of inducible or conditional promoters. To isolate such cell lines, in one embodiment, the transfected and optionally drug-selected cells are first minimally induced to affect transcription of the inducible genes, and the cells are then subjected to FACS analysis following the transfection into them of signaling probes designed to recognize the appropriate RNAs. The cells obtained are maintained such that the toxic RNAs are induced and transcribed only when necessary.

Inducible systems may be advantageous for applications other than the expression of toxic RNAs. For instance, one induces the expression of genetic sequences stably transfected into cells at a certain point during the cell cycle of a synchronized cell line. Alternatively, if the expressed products of a set of one or more stably transfected genetic sequences is thought to act on the expressed products of another set, then it is of interest to clone the genetic sequences of the first set under the control of one inducible promoter, and those of the second set under the control of a second inducible promoter. By varied inductions, one studies the expressed products encoded by either set of genetic sequences in either the absence or the presence of the expressed products of the other set. In general, the DNA sequences which are incorporated into cells as described in the methods above can each be placed under the control of a promoter or other regulator of transcription with desired activity. For instance inducible, tissue-specific, time-specific or temporal promoters, enhancers or repressors may be used, as well as regulatory elements that are modulated, activated or repressed due to cellular or extracellular signals, including but not limited to one or more of compounds or chemicals, other cells, proteins, peptides, hormones, signaling molecules, factors secreted from cells, whole or fractionated extracts from organisms, tissues or cells, or environmental samples. In these cases cells are first exposed to appropriate levels of the agents regulating transcription prior to their exposure to the signaling probe.

14. Detecting Genetic Recombinational Events in Living Cells and the Subsequent Isolation of Non-Recombined or Differentially Recombined Cells Parallel to the use of signaling probes to detect cells having undergone the recombinational events involved in the creation of stable cell lines, is the use of signaling probes to detect and isolate from a mixture of living cells those cells which have undergone other specific recombinational events. The same principle can be used to assay for VDJ recombination, translocation, and viral genome integration, for instance.

In cellular recombinational events, for instance, one sequence of genomic DNA is swapped for another. If a DNA sequence encoding a region where a recombinational event occurred is transcribed into RNA, then the presence of such an event is detected by a signaling probe designed to recognize either the RNA transcribed from the unrecombined DNA sequence, or that which is transcribed from the recombined sequence. Such an assay can also be carried out using the Fluorescent Microscope (or other equipment which can quantify the resulting signal). If one would like to separate cells which have recombined from those which have not, then one subjects the cells to FACS and sorts them. In addition, FACS can be used to sort out cells based on the presence or absence in them of numerous recombinational events.

15. Sorting Cells on the Basis of Expressed RNAs

The use of signaling probes as described herein allows cells to be sorted based on their expression of RNAs encoding internally localized, cell-surface localized, or secreted proteins as well as for other RNAs that may be present in the cell. For instance, starting from a mixed population of cells, one isolates those cells which express internally localized proteins of interest by designing signaling probes which recognize the mRNAs which give rise to these proteins. These signaling probes are transfected into the mixture of cells and FACS can be used to sort them as appropriate. Multiple rounds of sorting may be carried out.

Additionally, a researcher may be interested, for instance, in isolating cells which express the mRNA of one or more specific protein or RNAs that are transcribed in response to a given added factor, or in determining which added factor induces or represses the transcription of one or more proteins or RNAs. The added factors which may be tested in this way may include but are not limited to one or more of nucleic acids, proteins, peptides, hormones, signaling molecules, chemical compounds, inorganic or organic chemicals, cells, whole or fractionated extracts from or derived from organisms, tissues or cells, products purified or isolated from cells or organisms, samples from the environment or other sources.

To isolate cells that are induced to express one or more specific RNAs in response to a cytokine, for instance, a mixture of cells is first induced by the cytokine, then transfected with signaling probes, each of which is designed to recognize the mRNA that would give rise to one of the proteins of interest. In one embodiment, the FACS is then used to isolate those cells which score positive for the mRNA of interest. In an alternative embodiment, one also assays cells infected with a virus, for instance, for their expression of a particular gene. Alternatively, a set or library of compounds such as a chemical compound library, or an expression library of RNAs can be applied to cells to determine which if any compounds or mixture of compounds, or RNAs induces, represses or modulates the transcription of one or more specific proteins or RNAs.

It is possible with the methodology described hereinabove to detect cells positive for the presence of RNAs with one or more of the following different roles: messenger RNAs that encode proteins, fusion proteins, peptides fused to proteins, export signals, import signals, intracellular localization signals or other signals, which may be fused to proteins or peptides; antisense RNA, siRNA, short RNAs which form hairpin structures that have an activity similar to siRNA; structural RNAs, cellular RNAs including but not limited to such as ribosomal RNAs, tRNAs, hnRNA, snRNA; random RNAs, RNAs corresponding to cDNAs or ESTs; RNAs from diverse species, RNAs corresponding to oligonucleotides, RNAs corresponding to whole cell, tissue, or organism cDNA preparations; RNAs that have some binding activity to other nucleic acids, proteins, other cell components or drug molecules; RNAs that may be incorporated into various macromolecular complexes; RNAs that may affect some cellular function; or RNAs that do not have the aforementioned function or activity but which may be expressed by cells nevertheless; RNAs corresponding to viral or foreign RNAs linker RNA, or sequence that links one or more RNAs; or RNAs that serve as tags or a combination or recombination of unmodified mutagenized, randomized, or shuffled sequences of any one or more of the above. RNAs may be under the control of constitutive or conditional promoters including but not limited to inducible, repressible, tissue-specific, or temporal promoters or a combination or recombination of unmodified or mutagenized, randomized, shuffled sequences of any one or more of the above. Expression of the RNAs described above may result from the introduction into cells of DNA constructs, vectors or other delivery methods that deliver nucleic acids that result in their expression.

16. In Vivo Detection of Nucleic Acids and Subsequent Selection of Cells Using Protease Probes The present invention is also directed to a novel form of protease probe which, in contrast to the signaling probe, exhibits proteolytic activity upon binding to their target nucleic acids. Such proteolytic activity may be used for detection purposes, but also to degrade particular protein sequences in a cell should the target nucleic acid be present in the cell. For example, a protease which specifically cleaves a viral protein may be activated when transcription of a viral sequence is activated, such as in a latent infection and where, e.g., the protease probe is directed against the viral message).

In another aspect, the present invention is directed to a proteolytic activity-generating unitary hybridization probe, herein referred to as a protease probe. Such protease probes also comprise nucleotides or modified nucleotides complementary to a target RNA and nucleotides or modified nucleotides mutually complementary. These protease probes operate in a similar fashion to the aforementioned probes, but instead of a production of or change in fluorescent signal upon interaction of the signaling probe with its target nucleic acid sequence, the protease probe becomes proteolytic in the presence of the target.

One can substitute protease probes in place of signaling probes in the above methods, yielding new possibilities. Upon transfection of protease probes into cells expressing the RNA that is recognized by a protease probe, the protease probe hybridizes to its target. This causes activation of the protease as in its hybridized state, the protease is no longer in the vicinity of its protease inhibitor. A cell in which the target of such a protease probe is present and recognized, is damaged and is thus selected against. Cells not expressing this mRNA are more or less unaffected. Conversely, the protease probe can be designed to catalyze a proteolytic reaction which stimulates or otherwise imparts a beneficiary effect on cell growth or viability, or imparts a growth advantage to cells where its target is present and recognized.

Additionally, protease probes are useful in various other applications. The activity of the protease can be readily measured, and furthermore, the active protease in the presence of a particular nucleic acid target sequence may be employed not only for detection purposes but also for therapeutic purposes, in which, for example, a cell in which the protease probe is delivered is proteolyzed and rendered nonviable if a particular gene is transcribed, for example, one related to cellular transformation, oncogenesis, dysproliferation, and the like. For example, given a mixture of cells in which some of the cells are infected by a particular virus, one introduces into the cells a protease probes that targets a specifically viral mRNA. Cells which carry such an mRNA activate the proteolytic activity of the protease probe they contain, and this destroys these cells.

Preferably, the proteolytic enzyme inhibitor is a peptide or small chemical, although other molecules including but not limited to metals and metal chelators are also useful, to provide reversible inhibition of the enzyme upon interaction with the inhibitor. Examples of useful pairs of proteolytic enzymes and inhibitors of the proteolytic enzyme include but are not limited to aminopeptidase and amastatin, trypsin-like cysteine proteases and antipain, aminopeptidase and bestatin, chymotrypsin like cysteine proteases and chymostatin, aminopeptidase and diprotin A or B, carboxypeptidase A and EDTA, elastase-like serine proteases and elastinal, and thermolysin or aminopeptidase M and 1,10-phenanthroline.

In addition, probes incorporating other interacting pairs can be used where one member of the interacting pair has a desired activity and the second acts to inhibit or diminish this activity when the probes are unbound to the target. Upon binding to their targets, the activity of the probe is exhibited as the inhibitory member of the interacting pair is no longer in the vicinity of the member having the desired activity.

Based on the foregoing description, the following methods may be carried out.

A method for isolating cells expressing at least one RNA, comprising the steps of:
  a) introducing into cells DNA encoding said at least one RNA;
  b) exposing said cells to at least one signaling probe that produces a detectable signal upon hybridization to said at least one RNA; and
  c) isolating said cells that produce said signal.

This method may further comprise the step of growing the isolated cells to generate a cell line expressing the RNA. A plurality of cell lines may be generated if the DNA construct is integrated at different locations in the genome of the transfected cells. Unless genomic integration of a transfected construct is directed to a particular location with the genome, integration is thought to occur randomly, so each positive cell may be different from another, and there would be multiple different cell lines all positive for the RNAs for which they selected. A plurality of cell lines may also be generated if the DNA construct is introduced into a mixed population of cells, for example, immortalized, primary, stem and germ cells or cell lines. The cells may also be from any established cell line, including but not limited to HeLa, HEK 293T, Vero, Caco, Caco-2, MDCK, COS-1, COS-7, K562, Jurkat, CHO-K1, Huvec, CV-1, HuH-7, NIH3T3, HEK293, 293, A549, HepG2, IMR-90, MCF-7, U-2 OS or CHO. Optionally, the DNA construct may further encode at least a drug resistance marker or other selectable marker, and the method may further comprise the step of selecting cells using the selection marker after step a). Isolated cells may be grown separately or pooled. Whenever cells are isolated, whether following transfection with one or more constructs or one or more expression libraries, the isolated cells may be grown separated from each other, or pooled.

The isolated cells may be further prepared to express a second RNA. In either a simultaneous or sequential fashion, additional steps include transfecting the cells or cell line with a second DNA construct encoding a second RNA; exposing said cells to a second signaling probe which produces a detectable signal upon hybridization to said second RNA; and isolating cells that exhibit the signal of at least one or both of said RNA and second RNA. The first signaling probe may produce the same or a different signal from the second signaling probe, for example, they may have the same or different fluorophores. Cells or cell lines expressing more than two RNAs may be provided by repeating the steps simultaneously or sequentially. The second DNA construct may also contain the same or different drug resistance or other selectable marker. If the first and second drug resistance markers are the same, simultaneous selection may be achieved by increasing the level of the drug. A plurality of cell lines may be generated by repeating the above steps in a simultaneous or sequential fashion using DNA constructs that form an expression library, wherein at least a portion of the cells express different RNA.

A related approach is disclosed in which a tag sequence associated with the transfected gene is used as the target for the signaling probe, of which one application is to allow the selection of cells whose RNA may be difficult to identify over background, for example, if the signaling probe detects a closely related RNA species. Accordingly, a method for isolating cells expressing at least one RNA is provided comprising the steps of:

a) introducing into cells DNA encoding said at least one RNA and at least one tag sequence;

b) exposing said cells to at least one signaling probe that produces a detectable signal upon hybridization with the tag sequence; and c) isolating said cells that produce the signal.

This method is essentially the same as that described previously, except that the signaling probe used is designed to recognize the tag sequence rather than said RNA. A benefit of this procedure over the previous one is that only a small number of signaling probes, corresponding to the number of different tag sequences, is needed to prepare a large number of different cell lines expressing one or more RNAs. Optionally, the DNA construct may further encode at least a drug resistance or other selectable marker, and the method may further comprise the step of selecting cells resistant to at least one drug or other selective agent to which said marker confers resistance after step a). Isolated cells may be grown separately or pooled. Whenever cells are isolated, whether following transfection with one or more constructs or one or more expression libraries, the isolated cells may be grown separated from each other, or pooled.

Tag sequences refers to a nucleic acid sequence that is expressed as part of an RNA that is to be detected by a signaling probe. Signaling probes may be directed against the tag by designing the probes to include a portion that is complementary to the sequence of the tag. Examples of tag sequences which may be used in the invention, and to which signaling probes may be prepared include but are not limited to the RNA transcript of epitope tags which include but are not limited to HA (influenza hemagglutinin protein), myc, his, protein C, VSV-G, FLAG, or FLU. These and other tag sequences are known to one of skill in the art and typically correspond to amino acid sequences which may be incorporated into expressed protein products and often selected based on the availability of robust antibodies or protein detection reagents which may be used to report their presence. The tag sequences described herein are not meant to refer solely to sequences which may be used to modify at the amino acid level protein products encoded by the RNAs that are tagged, or to aid in the subsequent detection of any such modified protein products through use of the corresponding antibody or protein detection reagents. As used herein, the tag sequence provides at least a unique nucleic acid sequence for recognition by a signaling probe. The signaling probes have been described for use in detecting a variety of RNAs. Any of these RNAs may be used as tags. The DNA portion of the construct encoding the tag sequence may be in frame or out of frame with the portion of the DNA construct encoding the protein-coding portion of the at least one RNA. Thus, the tag sequence does not need to be translated for detection by the signaling probe.

A tag sequence may comprise a multiple repeated sequence which is designed to act as target sites for a signaling probe. Such a tag sequence would provide multiple signaling probe target sites. As a result, a greater number of signaling probes can bind. This would increase the total signal that can be generated from any one nucleic acid molecule that is to be detected by a signaling probe, and thus increase signal to noise ratios.

In addition to target sequences for probes, tags may comprise one or more additional sequences (referred to as "helper" or "helper sequence") designed, identified or selected to improve the detection of cells expressing the tags. For instance, helpers may have a number of effects including but not limited to effects on the folding, localization, or secondary, tertiary or quaternary structure of the tags where any or a combination of these effects acts to improve or increase the detection of the target sequence in cells. Helpers may influence tag folding or structure so that the target sequence is presented such that it is more accessible for probe binding. This could result from altered base-pairings or it could be due to binding interactions between the helpers and proteins or other cellular or introduced components. Helpers may work to stabilize or to make more dynamic the folding or structure of sequences comprising them. Also, helpers may act to stabilize with respect to degradation the sequences comprising them either before, during or following probe binding, and such effects could result directly from changes in folding or structure of sequences or as a consequence of the binding of proteins or cellular or introduced components to the helper sequences. Also, helpers may act to increase the transcription of sequences comprising them, for instance by enhancing the efficiency of transcriptional initiation or processing, decreasing premature termination of transcription or increasing the efficiency of post-transcriptional processing.

Functional approaches can be used to identify helpers regardless of how they exert their effect, and there may be different helper sequences for any given tag and corresponding probe. Helper sequences that work for multiple sets of a tag and corresponding probe may be identified functionally, also.

Variable sequences can be tested to identify which ones act as helpers for instance by constructing an expression library comprising a gene sequence and a tag sequence where variable sequences are inserted in between the gene and tag sequences. If the gene has a stop codon, the variable sequence may be inserted downstream of the stop codon. Additional variable sequences may be inserted at different sites. Next, the expression library is introduced into cells, and the cells are subsequently assayed by introduction of signaling probe directed against the target sequence. Cells that exhibit increased signal above control are detected (where control signal is the signal exhibited by control cells or cells into which a control expression construct, for instance one comprising the gene and the tag but no additional variable sequence, has been introduced). Such cells may be isolated for instance by FACS and the variable sequences represented by them may be isolated and further characterized, if desired. This approach can be used to detect or identify sequences that act as helper sequences for the specific combinations of a gene, tag and corresponding signaling probe used. Essentially the same approach can be used to find helper sequences for any sequence that comprises at least a target sequence for a corresponding signaling probe (i.e., an expression library comprising either a variable sequence and a target sequence but for instance no gene or an expression library comprising a gene, itself comprising the target sequence, and a variable sequence but no tag can each be used to detect suitable helpers). Cells that are isolated may be grown and cell lines may be generated.

The benefit of helper sequences that are detected or identified in this way may be specific for the sequence context which was used (i.e., for the specific tag, gene, target sequence or corresponding probe). More versatile helper sequences that are beneficial for more broadly in various sequence contexts can be determined experimentally for instance by following the methods described above. For instance, iterative rounds of selection of variable sequences can be performed where variable sequences acting as helper sequences can be isolated in each round and then tested in a subsequent rounds. In this case for instance, each subsequent round of testing would be performed by creating expression vectors where the sequences isolated from the previous round would be used to create an expression construct comprising a gene or tag or target sequence that is different from that used in the expression construct of the first round. The methods described can also be used to confirm the versatility of helper sequences given diverse sequence contexts. Identifying versatile or universal helper sequences can be helpful to aid in the detection of diverse sequences in cells.

One source of variable sequences could be genomic sequence. Genomic sequence can be digested with restriction enzymes to yield fragments of various sizes which can be obtained for cloning to create the expression libraries.

Tag sequences can either be chosen or designed to exhibit a certain amount of predicted or experimentally determined secondary structure, with the goal of optimally presenting the tag sequence for signaling probe binding. As such, tag sequences comprise at least a sequence against which at least one signaling probe is directed and tag sequences may in addition comprise additional sequence which is not chosen or designed to directly interact with the signaling probe. Nucleic acid folding prediction algorithms may be used to design potential tag sequences according to their structural adaptations. See for example, *Nucleic Acids Res.* 31: 3429-3431 (2003), hereby incorporated by reference. The nucleic acid folding prediction algorithms often predict a number of energetically most favorable structures of a given sequence. Alternatively, libraries of sequences representing variable nucleic acid sequences, for instance including but not limited to digested genomic DNA, can be assayed to determine or identify which sequences act to aid the detection of the tag sequences by signaling probes. This represents a functional approach to identification or isolation of tag sequences. This can be accomplished by creating expression libraries comprising at least a common sequence chosen or designed to be recognized by signaling probe, and at least a variable sequence. Such an expression library can be transfected into cells, the cells can then be exposed to signaling probe, and the most highly positive cells can be isolated by FACS. The variable sequences represented by these cells may then be isolated. For instance, the sequences may be amplified directly from the isolated cells by PCR techniques followed by cloning of amplified products. Alternatively, the isolated cells may be lysed to result in the release of the DNA constructs corresponding to the variable sequences expressed in the isolated cells, and these constructs or vectors may be isolated and propagated from the resulting material. For instance, in the case where the constructs are plasmid vectors, the lysed material may be used to transform competent bacterial cells, followed by isolation and amplification of the plasmid using bacterial hosts. For tag sequences incorporating multiple repeated sequence units, each of these units may not necessarily adopt the same structure due to potential interactions between the repeated units and/or other sequence present in the molecule incorporating the tag sequence. The structure of any given tag sequence could be influenced by its sequence context.

Figure 36:
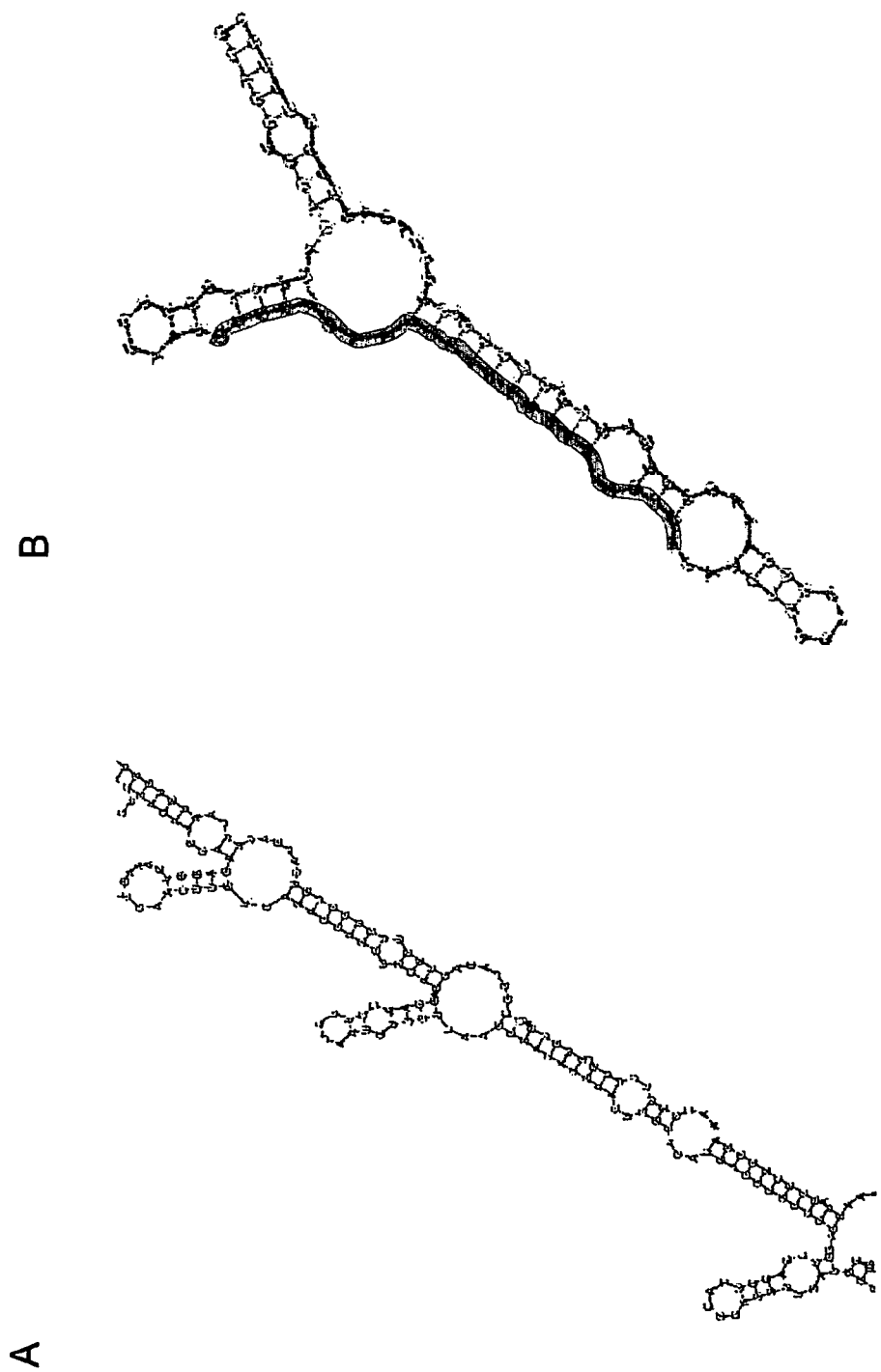

In one embodiment, the tag sequence is derived from reverse-vav RNA. In one embodiment, the tag sequence forms a three-arm junction structure (FIG. 36). In one embodiment, the tag sequence is 10-100, 80-100, 90-100, 80-120, 100-2 Kb, 2 Kb-15 kb nucleotides in length. In one embodiment, the target sequence is the region from all or part of the 3' side of the stem of the first stem-loop region, to the linkage between the first and second stem-loop region, to all or part of the 5' side of the stem of the second stem-loop region (FIG. 36).

Figure 37:
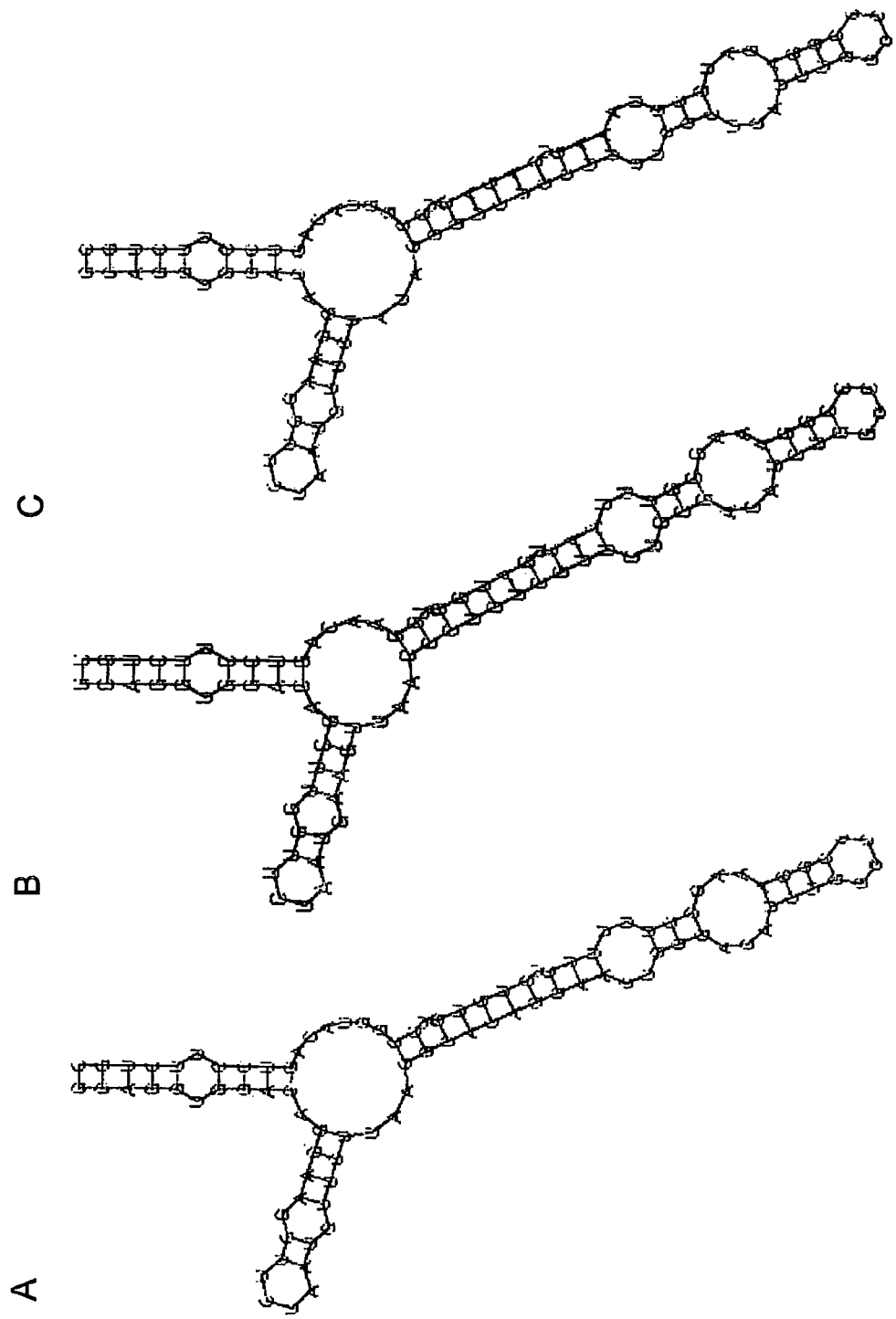

In one embodiment, the stem region comprises 8-9 basepairs, the first stem-loop region comprises 4-6 basepairs and the second stem-loop region comprises 13-17 basepairs (FIG. 37). In one embodiment, the stem regions of the three arms further comprise non-complementary regions. In one embodiment, the stem of the stem region and first-stem-loop region further comprise one mismatch region, the second stem-loop region further comprises 2-7 mismatch or bulge regions. In one embodiment, the linkage between the stem regions has a total of 8-12 nucleotides (FIG. 37). In one embodiment, the tag sequence comprises the structure or sequence according to FIG. 42 A, B or C. In another embodiment, the tag sequence has the energetically more favorable structures predicted from the sequence according to FIG. 42 A, B or C.

The present invention also provides a DNA construct comprising at least one DNA encoding at least one RNA of interest and a tag sequence as described above. The invention also provides vectors and cells comprising the DNA construct.

In a further embodiment, the cell line may be made to express at least a second RNA; the steps further including transfecting the cell line with a second DNA construct encoding the second RNA and a second tag sequence, and optionally, a second selectable marker, e.g., a drug resistance marker; optionally, selecting for cells transcribing the second marker; exposing the cells to a second signaling probe that produces a detectable signal upon hybridization with the second tag sequence, and isolating the cells that exhibit the signal of both or at least one of the first and the second tag sequence. In the case of two RNAs, the portion of the DNA sequence encoding the second tag sequence may also be in frame or out of frame with the portion of the DNA sequence encoding the protein-coding portion of the second RNA. The second RNA may be transfected either simultaneously or sequentially with the first. Should the method be performed simultaneously, and the same selectable marker, e.g., a drug resistance marker is used for both constructs, a higher level of drug or appropriate selective agent may be used to select for cells expressing both constructs. Furthermore, more than two RNAs may be provided in the cell line by repeating the aforementioned steps.

A plurality of cell lines may be generated by repeating the above steps in a simultaneous or sequential fashion using DNA constructs that form an expression library. In one embodiment, the expression library uses a single tag sequence, and cells are exposed to the same signaling probe which is complementary to the tag sequence. In another embodiment, different expression libraries can use different tag sequences. In one embodiment, each cell line expresses one RNA. In another embodiment, each cell line expresses more than one RNA. This can be achieved by transfecting the cell with multiple DNA constructs sequentially or simultaneously. The likelihood of obtaining a cell stably transfected with multiple DNA constructs may be increased by introducing a higher concentration of DNA constructs used for transfection. Alternatively, the starting cells may have already been transfected with a first DNA construct to obtain a cell with multiple DNA constructs. Also, multiple different expression libraries may be used to transfect cells. Each library may incorporate a distinct tag sequence that is detected using corresponding signaling probes. Each expression library may comprise a selectable marker, e.g., a drug resistance gene.

Isolated cells may be grown individually or pooled. Individually isolated or pooled cells may be grown to give rise to populations of cells. Cell lines may be generated by growing individually isolated cells. Individual or multiple cell lines may be grown separately or pooled. If a pool of cell lines is producing a desired activity, it can be further fractionated until the cell line or set of cell lines having this effect is identified. This may make it easier to maintain large numbers of cell lines without the requirements for maintaining each separately.

Yet another method is provided for generating a cell line that overexpresses an RNA comprising the steps of:
 a) introducing into cells a first DNA encoding said RNA and a first tag sequence; and at least a second DNA encoding said RNA and a second tag sequence, wherein the first and second tag sequences are different;
 b) exposing said cells to at least one signaling probe that produces a detectable signal upon hybridization with said first tag sequence, and to at least one signaling probe that produces a detectable signal upon hybridization with said second tag sequence; and
 c) isolating cells that exhibit the signal of at least one of said signaling probes.

This method may further comprise the step of growing the isolated cells to generate a cell line expressing or overexpressing the RNA. A plurality of cell lines may be generated if the DNA construct is integrated at different locations in the genome of the transfected cell. Unless genomic integration of a transfected construct is directed to a particular location with the genome, integration is through to occur randomly, so each positive cell may be different from another, and there would be multiple different cell lines all positive for the RNAs for which they are selected. Optionally, the DNA construct may further encode at least a selectable marker, e.g., a drug resistance marker, and the method may further comprise the step of selecting cells using the selectable marker, e.g., selecting for resistance to at least one drug to which said marker confers resistance after step a). Whenever cells are isolated, whether following transfection with one or more constructs or one or more expression libraries, the isolated cells may be grown separated from each other, or pooled.

In one embodiment, the cells express an antisense or siRNA or shRNA or protein. In addition, cells made to express a particular protein or proteins may be used as the starting point for creating cells expressing proteins and antisense RNA molecules. Of course, the cells expressing the antisense or siRNA or shRNA molecules may be used as the starting point for adding additional RNAs encoding additional proteins, using the methods herein. Simultaneous transfection of RNAs encoding proteins and antisense or siRNA or shRNA molecules, with corresponding signaling probes and, if desired, tag sequences, may also be performed. The various combinations of the aforementioned procedures is embraced herein.

Likewise, methods are provided for isolating cells expressing at least one RNA comprising the steps of:
 a) providing cells suspected of expressing said at least one RNA;
 b) exposing said cells to at least one signaling probe that produces a detectable signal upon hybridization with said at least one RNA;
 c) isolating said cells that produce the signal.

The method may also be used to identify cells also expressing a second RNA, using a second signaling probe which produces a detectable signal upon hybridization to its target RNA, cells having fluorescence of both or each of the first and second signaling probes are isolated. Simultaneous expression of more than two RNAs is also achievable. Whenever cells are isolated, whether following transfection with one or more constructs or one or more expression libraries, the isolated cells may be grown separated from each other, or pooled.

Another method is provided for isolating cells expressing at least one exogenous RNA and one endogenous RNA, comprising the steps of:
 a) introducing into cells DNA encoding said at least one exogenous RNA, wherein said cells potentially express at least one endogenous RNA;
 b) exposing said cells to at least a first signaling probe that produces a detectable signal upon hybridization to said at least one exogenous RNA;
 c) exposing said cells to at least a second signaling probe that produces a detectable signal upon hybridization to said at least one endogenous RNA, wherein said second signaling probe produces a different signal than that of the first signaling probe; and
 d) isolating said cells that produce at least one of said signals upon hybridization of said signaling probes to their respective RNAs.

The above two methods may further comprise the step of generating a cell line or a plurality of cell lines expressing said at least one exogenous RNA and at least one endogenous RNA by growing said isolated cells.

These methods are useful for an RNA that expresses a protein, e.g., a cell surface-localized protein, intracellular protein, secreted protein or other protein. These methods do not require the use of probes for the proteins themselves, which may be more difficult or will affect the cell such that further experiments cannot be performed. More than one RNA encoding a protein can be identified using a plurality of signaling probes, up to the number simultaneously detectable by the technology used for isolation. Optionally, the DNA construct may further encode at least a selectable marker, e.g., a drug resistance marker, and the method may further comprise the step of selecting cells using the selectable marker, e.g., by selecting cells that are resistant to at least one drug to which said marker confers resistance after step a). Isolated cells may be grown separately or pooled. Whenever cells are isolated, whether following transfection with one or more constructs or one or more expression libraries, the isolated cells may be grown separated from each other, or pooled.

For the above methods, in one embodiment, the cells are implantable in an animal. In one embodiment, the signaling probe is a fluorogenic probe, and the cells that express said RNA fluoresce. Isolating said cells that fluoresce may be carried out using fluorescence activated cell sorter technology or any technology that can be used to isolate cells based on fluorescence. In one embodiment, two signaling probes are used to target the RNA or tag sequence. The fluorophore of the first probe may be the same or different from that of the second probe. In the case of two different fluorophores, they may have similar or different emission wavelengths. At present, FACS technology can allow the detection of up to seven different fluorophores during a sorting procedure. The above methods may be repeated simultaneously to obtain the expression of up to seven different proteins. If desired, a cell line expressing seven different proteins may then be used as the starting point for the introduction of more proteins following the procedure. As FACS technology advances, it will be able to resolve a greater number of signals, and one would be able to select for cells having a greater number of RNAs in one application of FACS.

Naturally, the aforementioned procedures may be used to quantify the level of at least one RNA transcript expression in a biological sample comprising the steps of:
  a) exposing the biological sample to a first signaling probe which produces a detectable signal upon hybridization with said RNA transcript;
  b) quantitating the level of the signal in the biological sample; and
  c) correlating the level of signal with said level of the at least one mRNA transcript.

The biological sample may be a cellular sample, a tissue sample or preparations derived thereof; these may be frozen and/or fixed, for example, with formaldehyde, glutaraldehyde, or any number of known cellular fixatives which do not interfere with the detection of RNA using signaling probes. Preparations of cellular samples include but are not limited to subcellular organelles or compartments, mitochondria, organelles of cells, subcellular fractions, plasma membrane of cells intracellular or extracellular material, membrane preparations, preparations of nucleic acid from any one or more of these, preparations of any virus or other virus or organism present in any one or more of these, or any combination of one or more of these.

For the embodiment of fluorogenic probes, the fluorescence may be quantitated by fluorescence microscopy or fluorescence-activated cell sorter technology. Additional RNA species may be quantitated (i.e., quantified) simultaneously using a second signaling probe which fluoresces upon hybridization to a second RNA transcript. The above method may be used simultaneously with assays that utilize a fluorogenic reporter for the detection of intracellular events, states or compositions. Such fluorescent assays include but are not limited to TUNEL, Apoptosis, necrosis, Ca2+/Ion flux, pH flux, immunofluorescence, organelle labeling, cell adhesion, cell cycle, DNA content, and assays used to detect interactions between: protein-protein, protein-DNA, protein-RNA. Reagents which may be fluorescently labeled for use in these assays include but are not limited to Proteins (labeled with fluorescent molecules or autofluorecent proteins); fluorescent metabolic indicators (C12 resazurin, CFSE for cell divisions); fluorescent substrates or by-products; fluorescently-labeled lectins; fluorescent chemicals; caged fluorescent compounds; fluorescent nucleic acid dyes; fluorescent polymers, lipids, amino acid residues and nucleotide/side analogues.

Introduction of antisense or siRNA molecules in cells is useful for functionally eliminating or reducing the levels of one or more proteins or RNAs from the cell. Following the above methods, a method is provided for isolating cells or generating cells functionally null or reduced for expression of at least one preselected protein or RNA comprising the steps of providing in said cells a plurality of antisense or siRNA to said preselected protein or RNA, each provided in accordance with the aforementioned methods, wherein said plurality of antisense or siRNA binds essentially all or a sufficient level of mRNA transcripts of said at least one preselected protein or RNA. The preselected protein may be an alternatively spliced form of a gene product.

Following similar lines, a method is provided for generating a transgenic animal that is a functionally null-expressing mutant of at least one preselected protein or RNA, or that expresses said at least one preselected protein or RNA at reduced levels, comprising carrying out the steps described hereinabove utilizing embryonic stem cells, and using said viable embryonic stem cells to produce said transgenic animal.

Likewise, a method is provided for isolating cells or generating a cell line which is functionally null or reduced for expressing at least one protein or RNA and overexpresses at least one other protein or RNA, comprising carrying out the methods herein on the same cells. In similar fashion, a method is provided for generating a cell line expressing a lethal antisense or siRNA under control of a inducible promoter, or a sequence which has some other binding or functional activity that results in the modulation of transcription levels. This can be achieved by carrying out the method herein, wherein the transfection step is performed in the presence of a minimal amount of an inducer or compound.

Therefore, the present invention provides a method for isolating cells that overexpress at least a first protein and which are functionally null expressing or reduced in expression for at least a second protein, comprising the steps of:
  a) introducing into cells at least a first DNA encoding at least one RNA that encodes said at least first protein, and at least a first tag sequence; and at least a second DNA encoding said at least one RNA and at least a second tag sequence, wherein said first and second tag sequences are different;
  b) introducing into cells at least one DNA encoding at least one antisense RNA or siRNA that binds to or interferes with the mRNA transcript of said at least second protein;
  c) exposing said cells to at least a first signaling probe that produces a detectable signal upon hybridization with said at least first tag sequence, and to at least a second signaling probe that produces a detectable signal upon hybridization with said at least second tag sequence;
  d) exposing said cells to at least one signaling probe that produces a detectable signal upon hybridization to said at least one antisense RNA or siRNA; and
  e) isolating cells that produce at least one of said signals upon hybridization of said signaling probes to their respective RNAs.

In yet another embodiment, the present invention provides a method of identifying a compound that modulates transcription of at least one preselected RNA, comprising the steps of:
  a) adding individual or a set of compound to cells;
  b) exposing said cells to at least one signaling probe which produces a detectable signal upon hybridization with said at least one preselected RNA;
  c) quantitating the level of the signal in said cells;
  d) identifying cells that have an increase or decrease in signal compared to the signal of cells with no compound added; and optionally
  e) identifying compounds that modulate transcription of said at least one preselected RNA.

In one embodiment, said preselected RNA is encoded by the genome of the cell. In one embodiment, said preselected RNA is encoded by a DNA construct that is transfected into the cells prior to step a). In one embodiment, the transfected cells are exposed to a signaling probe designed to recognize said RNA and the cells express said RNA. In one embodiment, the DNA construct comprises a promoter or operator and encodes a repressor, enhancer, or a sequence that modulates transcription. In one embodiment, the preselected RNA is linked to a tag sequence, and the signaling probe produces a detectable signal upon hybridization with the tag sequence.

In another embodiment, the present invention provides a method of identifying an RNA sequence that modulates transcription of at least one preselected RNA, comprising the steps of:
  a) introducing into cells at least a construct encoding a test RNA sequence that potentially modulates transcription of said at least one preselected RNA;

b) exposing said cells to at least one signaling probe which produces a detectable signal upon hybridization with said at least one preselected RNA;

c) quantitating the level of the signal in said cells;

d) selecting cells that have an increase or decrease in signal compared to the signal of cells with no test RNA sequence; and optionally e) identifying a test RNA sequence that modulates transcription of said at least one preselected RNA.

These cells can be isolated and grown to give rise to cell lines. They may be grown separately or pooled. The modulation of transcription can be downstream up or down regulation of the preselected RNA. In one embodiment, said preselected RNA is encoded by the genome. Said preselected RNA is encoded by a DNA construct that is transfected into the cells prior to step a). In one embodiment, the transfected cells are exposed to a signaling probe designed to recognize said RNA and the cells express said RNA. In one embodiment, the preselected RNA is linked to a tag sequence, and the signaling probe produces a detectable signal upon hybridization with the tag sequence. In one embodiment, an expression library of RNA sequences is used to identify the RNA sequences that modulate transcription. In one embodiment, the test RNA sequence is linked to a tag sequence. Step e) is facilitated by exposing the cells following step a) to at least a signaling probe that produces a detectable signal upon hybridization to said RNA sequences or tag sequences, followed by step b). The signals produced by the signaling probes directed to the test RNA sequence or tag sequence thereof may be different from the signaling probe directed to the preselected RNA, and therefore the cells may be exposed to different signaling probes simultaneously.

A method is also provided herein for identifying genetic recombinational events in living cells comprising the steps of:

a) exposing a cell to a signaling probe that produces a detectable signal upon hybridization with an RNA sequence selected from the group consisting of that transcribed from a recombined sequence and that transcribed from the non-recombined sequence; and b) detecting said cells expressing said RNA sequence.

The detecting and/or sorting of the cells may be performed by FACS or fluorescence microscope.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention. Methods and materials similar or equivalent to those described herein can also be used in the practice or testing of the present invention.

17. Identification of Reagents or Compounds to Introduce or Improve the Introduction of Signaling Probes into Cells or to Enhance the Detection of Targets Reagents that can be used to introduce signaling probes into cells can be identified by testing various chemicals including but not limited to proteins, lipids, polymers, extracts or compounds or mixtures of these. The chemicals may be in gas, liquid or solid form. This can be done by mixing the chemicals with signaling probe in various ratios ranging from 1:1,000,000,000 to 1,000,000,000:1 in various solvents including but not limited to organic and aqueous solvents, buffered solutions or media or any combination of these, where the mixture is incubated for various time periods ranging from 1 minute to 48 hours and where the incubation is performed under various temperature conditions ranging from below 0 to above 100 degrees Celsius and with various degrees of agitation or mixing from none to gently shaking or rocking to vortexing or constant pipetting and where the incubation is carried out in light or dark or under various other environmental conditions. Next, the mixtures would be applied to cells and probe delivery would be assayed using fluorescence microscopy, fluorescence plate reader technology or by FACS or other fluorescence detection method. This may be done for instance in 96, 384 or 1536 well plates or on beads compatible with subsequent high throughput analysis. Note that when using beads, the beads may be analyzed or isolated using FACS and if they are additionally coded isolated beads can be used to determine the identity of the mixtures with which they were treated.

The cells used may be living or fixed and may be presented attached to a solid surface including but not limited to tissue culture plates or beads or they may be in suspension. The cells may be washed using a variety of buffers or solutions prior to addition of the mixtures. Once the reagents have been applied to the cells the reaction may be incubated for various periods of time with variable degrees of agitation of mixing in light or dark or under various other environmental conditions and at various temperatures, all as described above, and where these parameters may be limited for instance if cell viability is to be maintained. Following the incubation, the cells may be analyzed directly or washed as described above prior to analysis.

The above methods may be carried out using a signaling probe or a constitutively active probe (for instance in the case of fluorogenic probes, a probe lacking a quencher may be used). Also, each of the mixtures to be tested may be tested using more than one cell sample. For instance, a mixture may be tested using both cells known to comprise the target of the signaling probe used as well as control cells. The multiple cell types may be presented mixed or separately. Preferred mixtures would be those that result in increased signal to noise, for instance those that result in increased signal in cells comprising the target compared to control cells.

Similarly, essentially the same methods could be performed except where the cells are added to the mixtures. For instance, the mixtures to be tested could first be applied to test chambers for instance to wells of 96, 384 or 1536 well plates or beads, and the cells could be applied next. Cells may be added directly to the plated mixtures or they may added once the mixtures have been processed, for instance by drying, heating or evaporation.

In a related manner, compounds can be tested for their ability to enhance the detection of targets in cells using signaling probes. In this case, signaling probes would first be introduced into cells where the cells could include both cells that are known to comprise the target and control cells. Next, chemicals as described above and using variable conditions and parameters as described above could be assayed for their ability to improve signal. Note that the chemicals used in this case would not be mixed with signaling probes. Preferred chemicals would be those detected or identified to increase signal to noise ratios, for instance those that result in increased signal in cells comprising target compared to control cells. Chemicals identified using this approach may act by a number of mechanisms including but not limited to increasing the delivery of signaling probe into the cell cytoplasm, influencing the folding or structure of the target such that its detection by probe is improved (for instance by causing improved accessibility of the target) or by reducing non-specific background signal (for instance by reducing the amount of signaling probe attached to the outside surface of cells).

Chemicals that act to increase signal to noise ratios that can be used to introduce signaling probes into cells or that can be used to enhance the detection of target may also be determined by using test and control signaling probes each applied to cells known to comprise target and analyzing the chemicals for increased signal when using test signaling probe compared to control signaling probe.

Example 1

General Protocol. Starting Material: Signaling probes may be introduced into cells which are not expressing any RNAs from the DNA construct, or they may be used to detect RNA messages encoded from the DNA construct. The method of introduction of the signaling probes into either of these two types of cells is identical. The protocol below only requires that the cells to be analyzed are separable from each other and are amenable to FACS analysis.
1) As described more thoroughly in the description of the invention, signaling probes can be used in conjunction with FACS to sort out cells of a tissue based on expression or lack of expression within cells of specific RNAs. To this end, cells are first separated from each other by standard and well established methods such as homogenization and further chemical treatment. Appropriate signaling probes may then be introduced into such cells according to the protocol below.
2) Second, one may use signaling probes to select for cells expressing particular RNAs encoded by the DNA construct that have been transfected into a population of cells. To this end, one first transfects into a culture of cells a DNA construct or DNA constructs encoding the desired RNAs. Signaling probes may then be generated to recognize these RNAs, as described in more detail in the description of the invention. Transfection of the DNA construct into cells can be accomplished through a vast variety of methods including but not limited to using either ones own reagents or kits obtained from biotechnical firms (Qiagen, Promega, Gene Therapy Systems, Invitrogen, Stratagene, etc.), following the manufacturers' instructions. The DNA constructs are chosen such that each confers resistance to an antibiotic. Following the transfection of these DNA constructs into cells and a brief period for the recovery of the cells (usually 24 hours), the cells are subjected to the appropriate antibiotics such that only those cells to which the DNA constructs have conferred antibiotic resistance will survive. This generally takes three to four days and sometimes longer, depending both on the cell type and the antibiotic used.

The result is that a pool of cells remain and all of these would be resistant to antibiotics, but only a small fraction of which express the RNAs of interest. To select for the cells expressing the desired RNAs, the protocol below may be followed.

Example 2

Selection of Cells Using Signaling Probes

1) Transfect signaling probes into cells: signaling probes must be designed such that they will recognize the desired RNA either by hybridizing to a sequence endogenous in the RNA or by hybridizing to a tag that is added to the native RNA sequence. The design of signaling probes is elaborated upon in the description of the invention.
Transfection may be carried out by a vast variety of methods, similar to the transfection of the DNA constructs into cells. The method employed should be chosen based on the cell type being used as some cells respond better to some transfection methods over other methods. Transfection should be performed according to the instructions of the manufacturer of the transfection reagent used and may need to be optimized. Optimization may include treatment with chemicals to enhance delivery of transfected material into the cell or cell cytoplasm.

Transfection of signaling probes into cells may be carried out either on cells in suspension or on cells growing on solid surfaces, depending on the cells and transfection reagent used.
2) Following the transfection of fluorogenic probes into cells, the cells may then be subjected to FACS analysis. FACS can be used to sort out cells positive for any one or more of the fluorogenic probes used. It can also be used to sort out cells based on the intensity of the fluorogenic probes' signal, thereby allowing the researcher to select cells which express RNAs at varying levels.

Example 3

Generation of Cell Lines Expressing One or More RNAs

Following FACS selection, the positive-scoring cells can be maintained in appropriate medium as described in more detail in the description of the invention. These cells would give rise to cell lines expressing the RNAs of interest.

Concentration of the signaling probe: The concentration of signaling probe to be used depends on several factors. For instance, one must consider the abundance within cells of the RNA to be detected and the accessibility of this RNA to the signaling probe. For instance, if the RNA to be detected is present in very low amounts or if it is found in a portion of the RNA which is not readily accessible based on the three-dimensional folding of the RNA or due to protein binding to the RNA, then more signaling probe should be used here then in cases where the RNA to be detected is in high abundance and where the site recognized by the signaling probe is fully accessible. The exact amount of signaling probe to be used will have to be determined empirically for each application.

This can be accomplished by introducing different amounts of signaling probes into different groups of cells and selecting the condition where background fluorescence is low and where signal is high (the condition where not all but some of the cells score positive for the signaling probe).

Example 4

Exposing Cells to Signaling Probes

Cells attached, partially attached to, or settled on surfaces, or in solution may be exposed to FPs using a variety of methods to introduce molecules into cells, including but not limited to methods known in the art such as microinjection, mechanical shearing forces such as vortexing or mixing, passing through needles, or cell loading techniques including scraping, permeabilization using reagents such as certain antibiotics or detergents or a combination of reagents or solvents, or through use of a variety of transfection reagents of varying chemical properties (for instance liposomal based, chemical, or protein based), or through a combination of any one or more of these methods.

A more detailed sample protocol describing the use of lipid based transfection reagents is outlined below:

1. Preparation of Cells

Cells were plated into tissue culture wells either prior to (cell plating method 1) or on the same day as their exposure to (cell plating method 2) FPs, or cells were transferred to microcentrifuge tubes on the same day as their exposure to FPs (cell plating method 3).

All three preparative methods were used successfully. Cell plating method 1 allows sufficient time for the cells to attach to the surface of the culture well, while cell plating method 2 allows cells settled on the plate or attached to varying degrees to be processed depending on how much time is allowed to pass before cells are further processed, and cell plating method 3 allows for cells to be processed directly after they have been transferred to the tubes without allowing any time for them to settle or attach to any surface, although processing may also be carried out after a given amount of time has allowed to pass.

The cells were rinsed once or more with buffer such as serum-free media or PBS, although other buffers may be used. Generally, buffers included $MgCl_2$ at varying millimolar concentrations. The rinsing step may be omitted depending on the method of exposure.

2. Preparation of FP Reagents and Exposure to Cells

FPs were prepared for addition to cell preparations using commercially available transfection reagents and following protocols as described by the manufacturers. Manufacturers' protocols instruct that multiple parameters need to be empirically determined for multiple variables including which cell types are used, at what confluency or concentration cells should be processed, which specific molecules are to be introduced, in which proportion and absolute amounts various reagents are to be combined, and for what durations various steps are to be carried out or incubated, which steps may be omitted, and other variables. In the manufacturer's protocol, while certain ranges are provided, the protocols also suggest that these may have to be exceeded or other parameters may have to be optimized for successful use of their reagent. In general, the exposure of cells to FPs was carried out using parameters for these conditions which were within the ranges suggested as preliminary ranges by the manufacturers' protocols.

In general, FPs would be added to a tube containing serum-free media and the transfection reagent would be added to a second tube also containing serum free media using volumes and concentrations suggested by the manufacturer. The contents of each tube would be mixed, combined, and incubated for a length of time all as indicated by the manufacturers' protocols. Next, the FP would be applied to the preparations of cells, and the cells would be assayed following various incubation periods.

The protocol for exposing the FPs to cells in FIG. 32 is as follows:

Cells were plated a day before exposure to FPs, at approximately $1\times10^5$ cells/ml and at 0.5 ml per well of a 24-well plate. Cells used were cells transfected with and drug selected for an expression construct encoding r-vav.

FP reagents were prepared by incubating 0.625 to 2.5 ul of a 20 uM stock of FP in 50 ul to 200 ul of serum-free media containing from 1 to 4 mM $MgCl_2$ in one tube, and 0.625 to 2.5 ul of TfX50 (Promega) in an equal volume of serum-free media having the same concentration of $MgCl_2$ in a second tube. The contents of each tube would be mixed and then combined and incubated for 15 to 45 minutes at room temperature.

Cells were rinsed one or more times with serum-free media supplemented to the same concentration of $MgCl_2$ used above. The preparation of FP would be applied to the cells and extra serum-free media plus $MgCl_2$ may optionally be added depending on the volume of FP preparation added such that the cells are covered.

Cells were incubated for 3 to 5 hours in a tissue culture incubator and then assayed, and optionally DMSO may be added prior to observation. DMSO may aid in the delivery of the signaling probe into cells or in the folding or presentation of the target to be detected. Other solvents or chemicals may also be used with the aim of increasing delivery of the signaling probe into the cell or cell cytoplasm, or with the aim of improving detection of target by the signaling probe. Solvents and chemicals may be tested for their desirability or suitability by determining whether they result in increased delivery efficiency or increased signal to noise for the detection of target in cells expressing target compared to cells not expressing target, where both cell types are exposed to signaling probe.

The protocol for FIG. 34 was carried out essentially as described for FIG. 32 except FP16 was added to cells that were either transfected or untransfected and drug selected for an expression construct encoding an RNA comprising the target sequence 6CA4.

The protocol for exposing the FPs to cells in FIGS. 33 (A,B,C) are as follows:

Approximately 50 to 100 ul of cells plated at approximately $2.5\times10^5$ cell/ml in PBS supplemented with 4 mM $MgCl_2$ (PBS+4) was plated in wells of a 96-well plate, and the cells were exposed to FPs after sufficient time had passed for them to settle on the plate surface but before they had spread.

FP reagents were prepared by mixing 2.5 ul of a 20 uM stock of FP in 100 ul of PBS+4 in one tube and 7 ul of Lipofectamine (InVitrogen) was added to 100 ul of PBS+4 in a second tube. The contents of each tube were mixed and the solutions were incubated for 30 minutes at room temperature before they were combined, mixed and incubated for an additional 15 minutes at room temperature. 50 ul of the FP preparation was added to each well. A rinse of the cells with serum-free media or other buffer is optional. Cells were assayed following incubation in a tissue culture incubator for 2 to 3 hours and then assayed.

The protocol for exposing the FPs to cells in FIGS. 33 (D, E) were essentially the same as for FIG. 32 except 4 ul of Plus Reagent (InVitrogen) was added to the tube containing the FP.

Example 5

Analyzing and Isolating Cells Via FACS

Cells were exposed to FPs as described above and then processed to detach them from surfaces if they were attached and separate them from each other (for instance by using trypsin, although other enzymatic or non-enzymatic procedures may be used) and then they would be applied to FACS.

Following exposure to FPs, the FP containing solution would be removed from the cells and trypsin would be applied directly to the cells. Rinsing of the cells prior to this step using a variety of buffers or reagents may be used, including reagents designed to remove any FP reagent or other reagent which may have associated with cell surfaces during the exposure of the cells to FPs. The cells would be resuspended in buffer (for instance media containing serum and magnesium), and the cells would be further dispersed for instance by pipetting.

The cells were then analyzed by FACS according to standard FACS methods. For analysis of the cells, by comparing the fluorescence intensities of control cells and cells potentially expressing target sequences for the presence of these sequences using FPs, one can determine the background fluorescence of cells having undergone this procedure to determine if the cells potentially expressing targeted sequences show any changed fluorescence. Cells can be isolated either individually or in batch based on this information. For instance, existing technology enables the direct isolation of desired cells into unique wells of 96-well plates, or multiple desired cells may be obtained.

By increasing or decreasing the threshold of fluorescence intensity in FACS, cells exhibiting different levels of fluorescence signal may be isolated. One may wish to either set the threshold very high to have the high assurance that the cells are indeed positive or one may set a lower threshold if the purity of positive cells in the population that is obtained is not critical, for instance in the case where one would simply like to enrich the isolated cells for positive cells.

Example 6

Determining the Stability of Expression

One can monitor the expression levels of one or more genes in cells over time. For instance, given a cell line derived from cells isolated as positive for expression of a sequence using a FP designed to recognize the sequence, one can expose the cells and control cells to the FP and determine the ratio of fluorescence intensities of the two cell types for the signal emitted by the FP. This procedure can be repeated over time and changes in the ratio will reflect changes in relative levels of expression for the sequence being detected by the FP. This procedure may be carried out using multiple FPs.

Example 7

Design of Tag Sequence

The sequence for tag1 was used to generate two additional different sequences such that each of the sequences could be recognized by a unique signaling probe, with the intention of generating sequences having the same or similar predicted structure particularly with respect to the regions of the structure most directly involved in binding the signaling probe such that the target sequence of the signaling probe would be similarly presented for binding. For each of the two different tag sequences (tag2 and 3) that were generated, the targeted sequence within the original sequence for tag1 was first changed, and compensatory changes were made to some additional bases predicted to interact with the changed sequences in an effort to preserve the interactions at these same positions (FIGS. 43 and 44). The predicted structure of the new sequence was obtained and if it did not closely match the predicted structure of tag1, then the structure was used to predict which additional changes would be necessary. This was an iterative process performed until novel sequences having predicted structures similar to that of tag1 were obtained. Changes made to these sequences include base substitutions, deletions and additions.

Example 8

Exposing Signaling Probes at Elevated Temperatures

FP17 is predicted to form a 7 base pair mutually complementary region adjacent to the interactive pair. Elevated temperatures was required for FP17 to give a stronger fluorescence signal when it was incubated in the presence of target oligo compared to control oligo. For instance, by briefly placing them in hot water of 90 to 95° C. The tubes used here contained 16 ul total consisting of 5 ul of a 20 uM FP stock, 1.5 ul 25 mM MgCl$_2$, 8 ul 20 uM oligo, and 1.5 ul of water, having a final magnesium concentration of approximately 2.34 mM. The target oligo used was TO-FP1 and the control oligo used was TO-FP18 as described above.

Example 9

Chemically Modified Signaling Probes

Fifteen different chemically modified probes based on the FP1 probe sequence were synthesized. All of these probes have the same sequence and are directed against the same target sequence. The probes were introduced into 293T cells. These cells express a tag sequence that includes the target sequence of FP 1. FACS was used to analyze the fluorescence from these cells. The fifteen different probes are described below (SEQ ID NOS: 6-8, 2 and 10-20 are disclosed respectively in order of appearance). The results of the FACS analysis are shown in FIGS. 46-60. The results show that all fifteen of the probes are able to detect cells expressing the target sequence. All of the probes were identical with respect to concentration, method of delivery, fluorophore, quencher and sequence except for the chemical modification.

| Probe | Modification | Sequence | Comments |
|---|---|---|---|
| Mcon 1 | 2-Amino-dA and 5-Methyl-dC | GCCAGTCCCAGTTCCTGTGCCTTAAGAACCTCGC | C = 5-Methyl dC<br>A = 2-Amino dA |
| Mcon 2 | 2'-5' linked oligonucleotides | GCCAGTCCCAGTTCCTGTGCCTTAAGAACCTCGC | Bold = 2'-5' linked |
| Mcon 3 | Cytosine Arabanoside (Ara-C) | GCCAGTCCCAGTTCCTGTGCCTTAAGAACCTCGC | Bold = Ara-C |
| Mcon 4 | Spacer Phosphoramidite 9 | GCCAGSTCCCAGTTCCTGTGCCTTAAGAACSCTCGC | S = Spacer Phosphoramidite 9 |
| Mcon 5 | 2'-deoxy-2'-fluoro-RNA (2'-F-RNA) | GCCAGucccAGuuccuGuGccuuAAGAAcCTCGC | Underline = phosphorothioate linkage<br>Lowercase = 2'-F-RNA |
| Mcon 6 | 2'-deoxy-2'-fluoro-RNA (2'-F-RNA) | GCCAGuCCcAGuTCcTGuGCcTuAAGAAcCTCGC | Underline = phosphorothioate linkage<br>Lowercase = 2'-F-RNA |

-continued

| Probe | Modification | Sequence | Comments |
|---|---|---|---|
| Mcon 7 | 2-amino-A | GCCAGTCCCAGTTCCTGTGCCTTAAGAACCTCGC | A = 2-amino-A |
| Mcon 8 | 2'-O-methyl-5-Methyl-C (2'-OMe-5-Me-C) | GCCAGTCCCAGTTCCTGTGCCTTAAGAACCTCGC | C = 2'-OMe-5-Me-C |
| Mcon 9 | Locked Nucleic Acid (LNA) | GCCAGTCCCAGTTCCTGTGCCTTAAGAACCTCGC | Bold = LNA |
| Mcon 10 | Locked Nucleic Acid (LNA) | GCCAGTCCCAGTTCCTGTGCCTTAAGAACCTCGC | Bold = LNA |
| Mcon 11 | Phosphorothioate linkages | GCCAG<u>TCCC</u>AGTTCCTGTGCCTT<u>AAGAAC</u>CTCGC | Underline = phosphorothioate linkage |
| Mcon 12 | Phosphorothioate linkages | GCCAG<u>T</u>CCC<u>A</u>GTTC<u>C</u>TGTGCCT<u>T</u>AAG<u>A</u>ACCTCGC | Underline = phosphorothioate linkage |
| Mcon 13 | 2'-O-methyl-RNA (2'-OMe-RNA) | GCCAG*TCCCAGTTCCTGTGCCTTAAGAAC*CTCGC | Bold Italics = 2-O-methyl-RNA |
| Mcon 14 | 2'-O-methyl-RNA (2'-OMe-RNA) | GCCAG*TCCCAGTTCCTGT*G*CCTTAAGA*ACCTCGC | Bold Italics = 2-O-methyl-RNA |
| Mcon 15 | C-5 propynyl Pyrimidine Analogues | GCCAGu cccAGuuccuGuGccuuAAGAAcCTCGC | Lowercase = C5-propyne analog |

Note:
all probes have a 5' Cy5 and a 3' BHQ-3

What is claimed is:

1. A method of isolating a plurality of cells, wherein a subset of the cells expresses an RNA that is not expressed by another subset of the cells, comprising the steps of:
  introducing into cells a plurality of DNAs encoding a plurality of different RNAs, wherein each DNA further encodes a nucleic acid tag sequence, and wherein at least a subset of the plurality of DNAs encodes the same nucleic acid tag sequence;
  exposing the cells to a signaling probe that produces a detectable signal upon hybridization to said same nucleic acid tag sequence; and
  isolating, in a single application, the cells that exhibit at least one selected level of fluorescence at a selected wavelength.

2. The method of claim 1, wherein the plurality of different RNAs forms an expression library.

3. The method of claim 1, further comprising the step of culturing the isolated cells.

4. The method of claim 1, wherein said plurality of DNAs encodes at least one antisense RNA, shRNA, or siRNA.

5. The method of claim 1, further comprising separately growing individually isolated cells to generate a plurality of separate cell lines.

6. The method of claim 1, further comprising pooling the isolated cells.

7. The method of claim 6, further comprising growing the pooled cells.

8. The method of claim 1, wherein the plurality of different RNAs are selected from the group consisting of RNAs in the same or a related biological pathway, RNAs that act upstream or downstream of each other, RNAs that have a modulating, activating or repressing function to each other, RNAs that are dependent on each other for function or activity, RNAs that are components of the same complex, and RNAs that encode proteins selected from the group consisting of proteins in the same or a related biological pathway, proteins that act upstream or downstream of each other, proteins that have a modulating, activating or repressing function to each other, proteins that are dependent on each other for function or activity, proteins that are components of the same complex, and proteins from the same protein family.

9. The method of claim 1, wherein the nucleic acid tag sequence comprises multiple target sequences, wherein one signaling probe hybridizes to each target sequence.

10. The method of claim 1, wherein the DNA encodes multiple nucleic acid tag sequences.

11. The method of claim 1, wherein the DNA encoding said nucleic acid tag sequence is:
  (a) in frame with the DNA encoding said RNA; or
  (b) out of frame with the DNA encoding said RNA.

12. The method of claim 1, wherein the DNA further encodes a selection marker, and wherein the method further comprises the step of selecting the cells utilizing the selection marker after introducing the DNA into the cells but prior to exposing said cells to the signaling probe.

13. The method of claim 1, wherein said DNA is operably linked to a conditional promoter.

14. The method of claim 13, wherein the RNA encoded by the DNA, or a protein encoded by the RNA, is damaging to the cell when expressed.

15. The method of claim 1, wherein each DNA of said plurality of DNAs further comprises a second DNA sequence encoding a second RNA, wherein said second DNA sequence is under the control of a conditional promoter.

16. The method of claim 15, wherein said plurality of DNAs encodes a plurality of variable test RNAs, and wherein said method further comprises the steps of:
  assaying the isolated cells for the presence of the second RNA; and
  identifying the test RNA that activates the conditional promoter in cells that express the second RNA.

17. The method of claim 15, wherein the second RNA, or a protein encoded by the second RNA, is lethal or damaging to the cell when expressed.

18. A method of isolating cells each expressing RNAs from two or more RNA expression libraries, comprising the steps of:
  introducing into cells a plurality of DNAs encoding a first RNA expression library, wherein each DNA further encodes a first nucleic acid tag sequence, and wherein at least a subset of the plurality of DNAs encodes the same first nucleic acid tag sequence;
  introducing into the cells a plurality of DNAs encoding a second RNA expression library, wherein each DNA further encodes a second nucleic acid tag sequence, and wherein at least a subset of the plurality of DNAs encodes the same second nucleic acid tag sequence;
  exposing the cells to a first signaling probe that produces a detectable signal upon hybridization to said first nucleic acid tag sequence;
  exposing the cells to a second signaling probe that produces a detectable signal upon hybridization to said second nucleic acid tag sequence; and
  isolating, in a single application, the cells that exhibit at least one selected level of fluorescence at a selected wavelength for each of the first and second signaling probes.

* * * * *

SEQUENCE LISTING

<160> NUMBER OF SEQ ID NOS: 71

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gttcttaagg cacaggaact ggga                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcccagttcc tgtgccttaa gaac                                           24

<210> SEQ ID NO 3
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tttctctgtg atccggtaca gtccttctgc gcaggtggac aggaaggttc taatgttctt    60
aaggcacagg aactgggaca tctgggcccg gaaagccttt ttctctgtga tccggtacag   120
tccttctgcg caggtggaca ggaaggttct aatgttctt                          159

<210> SEQ ID NO 4

```
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
tttaactgat ggatggaaca gtccttctgc gcaggtggac agcttggttc taatgaagtt      60
aaccctgtcg ttctgcgaca tctgggcccg gaaagcgttt aactgatgga tggaacagtc     120
cttctgcgca ggtggacagc ttggttctaa tgaagtt                              157

<210> SEQ ID NO 5
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gtaaagtcag acatccggta cagtccttct gcgcaggtgg acaggaaggt tctaatgttc      60
tatagggtct gcttgtcgct catctgggcc cggagatgcg taaagtcaga catccggtac     120
agtccttctg cgcaggtgga caggaaggtt ctaatgttct at                        162

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: 5-methyl dC
<220> FEATURE:
<221> NAME/KEY: modified_base
<222> LOCATION: (10)
<223> OTHER INFORMATION: 2-amino dA
<220> FEATURE:
<221> NAME/KEY: modified_base
<222> LOCATION: (14)..(15)
<223> OTHER INFORMATION: 5-methyl dC
<220> FEATURE:
<221> NAME/KEY: modified_base
<222> LOCATION: (20)..(21)
<223> OTHER INFORMATION: 5-methyl dC
<220> FEATURE:
<221> NAME/KEY: modified_base
<222> LOCATION: (24)
<223> OTHER INFORMATION: 2-amino dA
<220> FEATURE:
<221> NAME/KEY: modified_base
<222> LOCATION: (27)..(28)
<223> OTHER INFORMATION: 2-amino dA
<220> FEATURE:
<221> NAME/KEY: modified_base
<222> LOCATION: (29)
<223> OTHER INFORMATION: 5-methyl dC

<400> SEQUENCE: 6
gccagtccca gttcctgtgc cttaagaacc tcgc                                 34

<210> SEQ ID NO 7
<211> LENGTH: 34
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 2'-5' linked
<220> FEATURE:
<221> NAME/KEY: modified_base
<222> LOCATION: (8)
<223> OTHER INFORMATION: 2'-5' linked
<220> FEATURE:
<221> NAME/KEY: modified_base
<222> LOCATION: (10)
<223> OTHER INFORMATION: 2'-5' linked
<220> FEATURE:
<221> NAME/KEY: modified_base
<222> LOCATION: (14)
<223> OTHER INFORMATION: 2'-5' linked
<220> FEATURE:
<221> NAME/KEY: modified_base
<222> LOCATION: (18)
<223> OTHER INFORMATION: 2'-5' linked
<220> FEATURE:
<221> NAME/KEY: modified_base
<222> LOCATION: (22)
<223> OTHER INFORMATION: 2'-5' linked
<220> FEATURE:
<221> NAME/KEY: modified_base
<222> LOCATION: (26)
<223> OTHER INFORMATION: 2'-5' linked
<220> FEATURE:
<221> NAME/KEY: modified_base
<222> LOCATION: (29)
<223> OTHER INFORMATION: 2'-5' linked

<400> SEQUENCE: 7
gccagtccca gttcctgtgc cttaagaacc tcgc                              34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: Ara-C
<220> FEATURE:
<221> NAME/KEY: modified_base
<222> LOCATION: (14)..(15)
<223> OTHER INFORMATION: Ara-C
<220> FEATURE:
<221> NAME/KEY: modified_base
<222> LOCATION: (20)..(21)
<223> OTHER INFORMATION: Ara-C
<220> FEATURE:
<221> NAME/KEY: modified_base
<222> LOCATION: (29)
<223> OTHER INFORMATION: Ara-C

<400> SEQUENCE: 8
gccagtccca gttcctgtgc cttaagaacc tcgc                              34

<210> SEQ ID NO 9
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```
gcaggtggac aggaaggttc taatgttcta tagggtctgc ttgtcgctca tctgggcccg        60
gagatgcgta aagtcagaca tccggtacag tccttctgc        99

<210> SEQ ID NO 10
<211> LENGTH: 34
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(29)
<223> OTHER INFORMATION: phosphorothioate linkage
<220> FEATURE:
<221> NAME/KEY: modified_base
<222> LOCATION: (6)..(9)
<223> OTHER INFORMATION: 2'-F-RNA
<220> FEATURE:
<221> NAME/KEY: modified_base
<222> LOCATION: (12)..(16)
<223> OTHER INFORMATION: 2'-F-RNA
<220> FEATURE:
<221> NAME/KEY: modified_base
<222> LOCATION: (18)
<223> OTHER INFORMATION: 2'-F-RNA
<220> FEATURE:
<221> NAME/KEY: modified_base
<222> LOCATION: (20)..(23)
<223> OTHER INFORMATION: 2'-F-RNA
<220> FEATURE:
<221> NAME/KEY: modified_base
<222> LOCATION: (29)
<223> OTHER INFORMATION: 2'-F-RNA

<400> SEQUENCE: 10
gccaguccca guccugugc cuuaagaacc tcgc        34

<210> SEQ ID NO 11
<211> LENGTH: 34
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(29)
<223> OTHER INFORMATION: phosphorothioate linkage
<220> FEATURE:
<221> NAME/KEY: modified_base
<222> LOCATION: (6)
<223> OTHER INFORMATION: 2'-F-RNA
<220> FEATURE:
<221> NAME/KEY: modified_base
<222> LOCATION: (9)
<223> OTHER INFORMATION: 2'-F-RNA
<220> FEATURE:
<221> NAME/KEY: modified_base
<222> LOCATION: (12)
<223> OTHER INFORMATION: 2'-F-RNA
<220> FEATURE:
<221> NAME/KEY: modified_base
<222> LOCATION: (15)
<223> OTHER INFORMATION: 2'-F-RNA
<220> FEATURE:
<221> NAME/KEY: modified_base
<222> LOCATION: (18)
<223> OTHER INFORMATION: 2'-F-RNA

```
<220> FEATURE:
<221> NAME/KEY: modified_base
<222> LOCATION: (21)
<223> OTHER INFORMATION: 2'-F-RNA
<220> FEATURE:
<221> NAME/KEY: modified_base
<222> LOCATION: (23)
<223> OTHER INFORMATION: 2'-F-RNA
<220> FEATURE:
<221> NAME/KEY: modified_base
<222> LOCATION: (29)
<223> OTHER INFORMATION: 2'-F-RNA

<400> SEQUENCE: 11
gccaguccca gutcctgugc ctuaagaacc tcgc                                34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 2-amino-A
<220> FEATURE:
<221> NAME/KEY: modified_base
<222> LOCATION: (24)..(25)
<223> OTHER INFORMATION: 2-amino-A
<220> FEATURE:
<221> NAME/KEY: modified_base
<222> LOCATION: (27)..(28)
<223> OTHER INFORMATION: 2-amino-A

<400> SEQUENCE: 12
gccagtccca gttcctgtgc cttaagaacc tcgc                                34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: 2'-OMe-5-Me-C
<220> FEATURE:
<221> NAME/KEY: modified_base
<222> LOCATION: (14)..(15)
<223> OTHER INFORMATION: 2'-OMe-5-Me-C
<220> FEATURE:
<221> NAME/KEY: modified_base
<222> LOCATION: (20)..(21)
<223> OTHER INFORMATION: 2'-OMe-5-Me-C
<220> FEATURE:
<221> NAME/KEY: modified_base
<222> LOCATION: (29)
<223> OTHER INFORMATION: 2'-OMe-5-Me-C

<400> SEQUENCE: 13
gccagtccca gttcctgtgc cttaagaacc tcgc                                34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)
<223> OTHER INFORMATION: LNA
<220> FEATURE:
<221> NAME/KEY: modified_base
<222> LOCATION: (4)
<223> OTHER INFORMATION: LNA
<220> FEATURE:
<221> NAME/KEY: modified_base
<222> LOCATION: (6)
<223> OTHER INFORMATION: LNA
<220> FEATURE:
<221> NAME/KEY: modified_base
<222> LOCATION: (10)
<223> OTHER INFORMATION: LNA
<220> FEATURE:
<221> NAME/KEY: modified_base
<222> LOCATION: (15)
<223> OTHER INFORMATION: LNA
<220> FEATURE:
<221> NAME/KEY: modified_base
<222> LOCATION: (17)
<223> OTHER INFORMATION: LNA
<220> FEATURE:
<221> NAME/KEY: modified_base
<222> LOCATION: (22)
<223> OTHER INFORMATION: LNA
<220> FEATURE:
<221> NAME/KEY: modified_base
<222> LOCATION: (25)
<223> OTHER INFORMATION: LNA
<220> FEATURE:
<221> NAME/KEY: modified_base
<222> LOCATION: (28)
<223> OTHER INFORMATION: LNA
<220> FEATURE:
<221> NAME/KEY: modified_base
<222> LOCATION: (33)
<223> OTHER INFORMATION: LNA

<400> SEQUENCE: 14
gccagtccca gttcctgtgc cttaagaacc tcgc                               34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: LNA
<220> FEATURE:
<221> NAME/KEY: modified_base
<222> LOCATION: (10)
<223> OTHER INFORMATION: LNA
<220> FEATURE:
<221> NAME/KEY: modified_base
<222> LOCATION: (13)
<223> OTHER INFORMATION: LNA
<220> FEATURE:
<221> NAME/KEY: modified_base
<222> LOCATION: (17)
<223> OTHER INFORMATION: LNA
<220> FEATURE:
<221> NAME/KEY: modified_base
<222> LOCATION: (22)
<223> OTHER INFORMATION: LNA
<220> FEATURE:
<221> NAME/KEY: modified_base
<222> LOCATION: (25)
<223> OTHER INFORMATION: LNA
<220> FEATURE:
<221> NAME/KEY: modified_base
```

```
<222> LOCATION: (28)
<223> OTHER INFORMATION: LNA

<400> SEQUENCE: 15
gccagtccca gttcctgtgc cttaagaacc tcgc                                34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(29)
<223> OTHER INFORMATION: phosphorothioate linkage

<400> SEQUENCE: 16
gccagtccca gttcctgtgc cttaagaacc tcgc                                34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: phosphorothioate linkage
<220> FEATURE:
<221> NAME/KEY: modified_base
<222> LOCATION: (10)
<223> OTHER INFORMATION: phosphorothioate linkage
<220> FEATURE:
<221> NAME/KEY: modified_base
<222> LOCATION: (14)
<223> OTHER INFORMATION: phosphorothioate linkage
<220> FEATURE:
<221> NAME/KEY: modified_base
<222> LOCATION: (19)
<223> OTHER INFORMATION: phosphorothioate linkage
<220> FEATURE:
<221> NAME/KEY: modified_base
<222> LOCATION: (23)
<223> OTHER INFORMATION: phosphorothioate linkage
<220> FEATURE:
<221> NAME/KEY: modified_base
<222> LOCATION: (27)
<223> OTHER INFORMATION: phosphorothioate linkage

<400> SEQUENCE: 17
gccagtccca gttcctgtgc cttaagaacc tcgc                                34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(29)
<223> OTHER INFORMATION: 2-O-Methyl-RNA

<400> SEQUENCE: 18
gccagtccca gttcctgtgc cttaagaacc tcgc                                34
```

```
<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 2-O-Methyl-RNA
<220> FEATURE:
<221> NAME/KEY: modified_base
<222> LOCATION: (10)
<223> OTHER INFORMATION: 2-O-Methyl-RNA
<220> FEATURE:
<221> NAME/KEY: modified_base
<222> LOCATION: (14)
<223> OTHER INFORMATION: 2-O-Methyl-RNA
<220> FEATURE:
<221> NAME/KEY: modified_base
<222> LOCATION: (19)
<223> OTHER INFORMATION: 2-O-Methyl-RNA
<220> FEATURE:
<221> NAME/KEY: modified_base
<222> LOCATION: (23)
<223> OTHER INFORMATION: 2-O-Methyl-RNA
<220> FEATURE:
<221> NAME/KEY: modified_base
<222> LOCATION: (27)
<223> OTHER INFORMATION: 2-O-Methyl-RNA

<400> SEQUENCE: 19
gccagtccca gttcctgtgc cttaagaacc tcgc                              34

<210> SEQ ID NO 20
<211> LENGTH: 34
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(9)
<223> OTHER INFORMATION: C5-propyne analog
<220> FEATURE:
<221> NAME/KEY: modified_base
<222> LOCATION: (12)..(16)
<223> OTHER INFORMATION: C5-propyne analog
<220> FEATURE:
<221> NAME/KEY: modified_base
<222> LOCATION: (18)
<223> OTHER INFORMATION: C5-propyne analog
<220> FEATURE:
<221> NAME/KEY: modified_base
<222> LOCATION: (20)..(23)
<223> OTHER INFORMATION: C5-propyne analog
<220> FEATURE:
<221> NAME/KEY: modified_base
<222> LOCATION: (29)
<223> OTHER INFORMATION: C5-propyne analog

<400> SEQUENCE: 20
gccaguccca guuccugugc cuuaagaacc tcgc                              34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 21
gcgagtccca gttcctgtgc cttaagaacc tcgc                                34

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcgcagaacg acagggttaa cttc                                          24

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgagtcgca gaacgacagg gttaacttcc tcgc                               34

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agcgacaagc agaccctata gaac                                          24

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgagagcga caagcagacc ctatagaacc tcgc                               34

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctgcagcgac aagcagaccc tatagaacgg g                                  31

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaatcccag ttcctgtgcc ttaagaactt cc                                    32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaatcgcag aacgacaggg ttaacttctt cc                                    32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggaaagcgac aagcagaccc tatagaactt cc                                    32

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcccagttcc tgtgccttaa gaacattag                                        29

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tcccagttcc tgtgccttaa gaacattagt                                       30

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgagtccca gttcctgtgc cttaagaaca ttagtctcgc                            40

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggaatcccag ttcctgtgcc ttaagaacat tagtttcc          38

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgattccca gttcctgtgc cttaagaaca tcac             34

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggactcccag ttcctgtgcc ttaagaacgt cc               32

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggtcccagt tcctgtgcct taagaacccc                  30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcgtcccagt tcctgtgcct taagaaccgc                  30

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atcgatgtag cttatggatc ttagc                       25

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
gcgagatcga tctagcttat ggatcttagc ctcgc                                    35
```

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
ctaatcgtaa ttcgtaagcc tggaa                                               25
```

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gcgagctaat cgtaattcgt aagcctggaa ctcgc                                    35
```

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gttgtgtggt tggttggtgt gttg                                                24
```

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gcgaggttgt gtggttggtt ggtgtgttgc tcgc                                     34
```

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
tcccagttcc tgtgccttaa gaac                                                24
```

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcgagagtcc cagttcctgt gccttaagaa cctctcgc          38

<210> SEQ ID NO 46
<211> LENGTH: 2771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

| | |
|---|---|
| accttgccaa aatcctgcac atcgaagagg tcaaaggctt cgaagagctc gctccgcttg | 60 |
| aggccgaact tctcacagca ggtggacagg aaggttctaa tgttcttaag gcacaggaac | 120 |
| tgggacatct gggggcgcag gttgacctca cgcaggttga tggcatgggg tagcaggttg | 180 |
| ttaagcagct gacacagaag gacaccatcc cggagggcct gggccagttc acacacctga | 240 |
| gccccatccc aggtcacgcg gtggctgggc ggcagcaccc ggcactggat gagccagtgg | 300 |
| gtgcattggc gccacagctc catggctacc gccggtgggg aagggcatga tcccccctgtt | 360 |
| ctgggcgatc ggggtccagg acagagcaga cagggtgtag atgcctccac cgtgtcgtcg | 420 |
| atctggtcgg acaggccact gtagatgtct tcatcaccta cactctcctc tcatgaggt | 480 |
| cctcatagat ctcgtcgcct tccgcctcct cattctccac gcagtcatac aggtcctcat | 540 |
| cctctcccgc aggcagcagc agcgcttgtc atactctgtc atcttgggcg gcatggacac | 600 |
| gggctccgag cgcgcagggg cttcaagaaa tgctgctgga tggagcccag cgtgtcagtg | 660 |
| tacttctcct ccgtctgctg gatgtatgaa cacgaagcag gtcctcaatg ttgataaaga | 720 |
| tgatctcaat gtcttgaggt tcaggaacc gttgatgaag acctggtaga gattggctgc | 780 |
| gccaggggtg cccagggctt ccttcatctc ctttaggaag tgaccaggtg tttgctggct | 840 |
| gactccacct ggctgcagta gcggccatag acgaggaacc tctccttgta tttccgttgt | 900 |
| tggctctctg agaacattcc tccagcttca tctgcacgtc ctcccgggct gcggccacac | 960 |
| ggtctggaga aggaggtgat atttgagaac tcgctgcata ggcaccatca gcaggtcccg | 1020 |
| cagggtgaac ctccccctcat ggcatccagg gccagccgca ggttctcctt ctccatcgcc | 1080 |
| tcctgcgtgt gtttcaccag ctcagctgga aattggtgat ctgtcgcagt gtctcgttgt | 1140 |
| ctcgcttgac ctcgttcacg cactgagcca ggtgatcttg agttccccgt cgatcttggg | 1200 |
| ccggccatag tgagccagag actggtccag gttctcaatg gactacagat gagtagagct | 1260 |
| ttgtcgagca ggaaggcata cctgtccatc ttggagcgcc gttccaccga ggtgagtcat | 1320 |
| cccgaacctg gaagctgtgc aggtttacaa agtccttgag gtcataggag tctcccctgc | 1380 |
| gctgccctgg gcaccttggt cctcgatcag gaggaacatg tggctccact tcttgttgtc | 1440 |
| tcggtctcct gaatggagat ggccatctca aactgctcca tccacttctt cttcaattct | 1500 |
| cttgtcttga agaacagctc atagatgtgg tctcctcaaa ggagaacatc tggaagtcat | 1560 |
| gcccgttggc ggtggcattc tccggataga tgttgcccgg caccgatggc agcggtagcc | 1620 |
| ctgatagaag gtacctctaa gcagcatctg acaggccttg cagtagttcc tgggaaatct | 1680 |
| tgcccatgtc ggccacatgg agggaccctc cccagacact ccttgtgtgc agatccatct | 1740 |
| tgggcagacc cagctcattc ctctttttgt cctgagccct gcgatgtagt ttgtccttct | 1800 |
| tcaagggttg agccgtagaa agggtccaat ggctccaggg ggtggaggaa gcccgtagta | 1860 |
| ttcctgaaac acctagtaga tgtatttctg ccctcccacc agttctgttc agcctcagcc | 1920 |
| ttcgtgagct ccacaatgtc tccacagaca ggtcctgagg agggcatgg acatagggct | 1980 |

```
tcaccctgtt acaaggaaac cagccaattt catcccgtcc gagcggttgg ccaggatgct    2040
ctctgcccct gcccgctcca tggggcctgc gtaccagaga tgacctcgac gttatattta    2100
atgctgatgg caaattctgc tgcatccttc accctctgcc gcaccaagaa agtagccccc    2160
ggaaagcctt tttctctgtg atccggtaca gtccttctgc tgtcatgatt ttaatgtgct    2220
tgacaaggtg gtgtccagag acttgaagca atcctttaga gagttctgct ggtaaaactc    2280
caccagctcc gtacaaaata ctttgtgctt cccactgctg gcctgctgat ggttctcttt    2340
tcaggctcct tgaaggggaa ctgatgtcac cctccttgag cgacagctct gatcggtctc    2400
gggcgcagaa gtcatagcgg gctttggctg tgcccagcca accggccat agatctcccc     2460 tcgccaccag ccttgctgtc ccttcttgtt aaggatcttg atgcgtctct ctgccaaggc    2520
accagggctc agcagtattc agaataatct tcctccacgt agttggcagg gaaacccgcc    2580
gggagctgtc acagcccctg ctccgctgc ctgcccacgc cgggctcaga gcctggagtt     2640
tctcatgtca gggcacatcc cgggagcacc gccagctgga cgctgcgctc ctccagtcca    2700
tcccaaagtc tcccttgag ccccgtctgc ttgagggac ccaagaggaa atcggggtgt      2760
tataaattaa c                                                         2771

<210> SEQ ID NO 47
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcaggtggac aggaaggttc taatgttctt aaggcacagg aactgggaca tctgggcccg    60
gaaagccttt ttctctgtga tccggtacag tccttctgc                           99

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcgaggttct taaggcacag gaactgggac tcgc                                34

<210> SEQ ID NO 49
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcaggtggac aggaaggttc taatgttctt aaggcacagg aactgggaca tctgggcccg    60
gaaagccttt ttctctgtga tccggtacag tccttctgc                           99

<210> SEQ ID NO 50
<211> LENGTH: 97
<212> TYPE: DNA
<213> ORGANISM: Artificial Sequence
<220> FEATURE:
<223> OTHER INFORMATION: Description of Combined DNA/RNA Molecule:
      Synthetic polynucleotide
```

```
<220> FEATURE:
<223> OTHER INFORMATION: Description of Artificial Sequence: Synthetic
      oligonucleotide

<400> SEQUENCE: 50
gcaggtggac agcttggttc taatgaagtt aaccctgtcg ttctgcgaca tctgggcccg      60
gaaagcgttt aacugatgga uggaacagtc cttctgc                              97

<210> SEQ ID NO 51
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcaggtggac aggaaggttc taatgttcta tagggtctgc ttgtcgctca tctgggcccg      60
gagatgcgta aagtcagaca tccggtacag tccttctgc                            99

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gaagttaacc ctgtcgttct gcga                                            24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gttctatagg gtctgcttgt cgct                                            24

<210> SEQ ID NO 54
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcaggtggac aggaaggttc taatgttctt aaggcacagg aactgggaca tctgggcccg      60
gaaagccttt ttctctgtga tccggtacag tccttctgc                            99

<210> SEQ ID NO 55
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcaggtggac agcttggttc taatgaagtt aaccctgtcg ttctgcgaca tctgggcccg      60
```

```
gaaagcgttt aactgacaga tggggtacag tccttctgc                    99
```

<210> SEQ ID NO 56
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
gcaggtggac agcttggttc taatgaagtt aaccctgtcg ttctgcgaca tctgggcccg    60
gaaagcgttt aacgatgggg tacagtcctt ctgc                              94
```

<210> SEQ ID NO 57
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
gcaggtggac agcttggttc taatgaagtt aaccctgtcg ttctgcgaca tctgggcccg    60
gaaagcgttt aactgatggg gtacagtcct tctgc                             95
```

<210> SEQ ID NO 58
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

```
gcaggtggac agcttggttc taatgaagtt aaccctgtcg ttctgcgaca tctgggcccg    60
gaaagcgttt aactgatgga tggtacagtc cttctgc                           97
```

<210> SEQ ID NO 59
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
gcaggtggac agcttggttc taatgaagtt aaccctgtcg ttctgcgaca tctgggcccg    60
gaaagcgttt aactgatgga tggtacagtc cttctgc                           97
```

<210> SEQ ID NO 60
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gcaggtggac aggaaggttc taatgttcta tagggtctgc ttgtcgctca tctgggcccg    60
gaaagccttt aagtcagaca tccggtacag tccttctgc                         99
```

<210> SEQ ID NO 61

```
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcaggtggac aggaaggttc taatgttcta tagggtctgc ttgtcgctca tctgggcccg      60
gaaagcctta aagtcagaca tccggtacag tccttctgc                            99

<210> SEQ ID NO 62
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcaggtggac aggaaggttc taatgttcta tagggtctgc ttgtcgctca tctgggcccg      60
gaaagcgtta aagtcagaca tccggtacag tccttctgc                            99

<210> SEQ ID NO 63
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gcaggtggac aggaaggttc taatgttcta tagggtctgc ttgtcgctca tctgggcccg      60
gaaagcgtta aagtcagaca tccggtacag tccttctgc                            99

<210> SEQ ID NO 64
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcaggtggac aggaaggttc taatgttcta tagggtctgc ttgtcgctca tctgggcccg      60
gaaagcgtaa agtcagacat ccggtacagt ccttctgc                             98

<210> SEQ ID NO 65
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gcagguggac aggaagguuc uaauguucuu aaggcacagg aacugggaca ucugggcccg      60
gaaagccuuu uucucuguga uccgguacag uccuucugc                            99

<210> SEQ ID NO 66
<211> LENGTH: 97
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 66
gcagguggac agcuuggunc uaaugaaguu aacccugucg uucugcgaca ucugggcccg      60
gaaagcguuu aacugaugga uggaacaguc cuucugc                              97

<210> SEQ ID NO 67
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcagguggac aggaagguuc uauguucua uagggucugc uugucgcuca ucugggcccg      60
gagaugcgua aagucagaca uccgguacag uccuucugc                            99

<210> SEQ ID NO 68
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gcagguggac aggaagguuc uauguucuu aaggcacagg aacugggaca ucugggcccg      60
gaaagccuuu uucucuguga uccgguacag uccuucugc                            99

<210> SEQ ID NO 69
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cugcacaucg aagaggucaa ag                                              22

<210> SEQ ID NO 70
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cgaacuucuc acagcaggug gacaggaagg uucuaauguu cuuaaggcac aggaacuggg      60
acaucugggg gcgcagguug accucacgca gguugaugg                            99

<210> SEQ ID NO 71
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 71
aaguagcccc cggaaagccu uuuucucugu gauccgguac aguccuucug cugucaugau        60
uuuaaugugc u                                                            71
```